US010351639B2

(12) United States Patent
Mertens et al.

(10) Patent No.: US 10,351,639 B2
(45) Date of Patent: Jul. 16, 2019

(54) ORGANOSILICA MATERIALS FOR USE AS ADSORBENTS FOR OXYGENATE REMOVAL

(71) Applicant: EXXONMOBIL CHEMICAL PATENTS INC., Baytown, TX (US)

(72) Inventors: Machteld M. W. Mertens, Boortmeerbeek (BE); Jo Ann M. Canich, Houston, TX (US); Suzzy C. H. Ho, Princeton, NJ (US); Quanchang Li, Dayton, NJ (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 15/526,521

(22) PCT Filed: Dec. 11, 2015

(86) PCT No.: PCT/US2015/065351
§ 371 (c)(1),
(2) Date: May 12, 2017

(87) PCT Pub. No.: WO2016/094848
PCT Pub. Date: Jun. 16, 2016

(65) Prior Publication Data
US 2017/0313791 A1 Nov. 2, 2017

Related U.S. Application Data

(60) Provisional application No. 62/091,071, filed on Dec. 12, 2014, provisional application No. 62/091,077, filed on Dec. 12, 2014.

(51) Int. Cl.
*C08F 6/00* (2006.01)
*B01D 15/00* (2006.01)
*B01D 15/08* (2006.01)

(52) U.S. Cl.
CPC ............. *C08F 6/005* (2013.01); *B01D 15/08* (2013.01)

(58) Field of Classification Search
CPC .................................. B01D 15/08; C08G 77/04
See application file for complete search history.

(56) References Cited

U.S. PATENT DOCUMENTS

| | | |
|---|---|---|
| 2,653,959 A | 9/1953 | Moore et al. |
| 2,943,105 A | 6/1960 | Caruthers |
| 3,178,392 A | 4/1965 | Kriner |
| 3,489,808 A | 1/1970 | Eberly |
| 3,931,350 A | 1/1976 | Sparks |
| 4,218,308 A | 8/1980 | Itoh et al. |
| 4,337,156 A | 6/1982 | DeRosset |
| 4,530,914 A | 7/1985 | Ewen et al. |
| 4,542,199 A | 9/1985 | Kaminsky et al. |
| 4,808,561 A | 2/1989 | Welborn, Jr. |
| 4,871,705 A | 10/1989 | Hoel |
| 4,933,403 A | 6/1990 | Kaminsky et al. |
| 4,937,299 A | 6/1990 | Ewen et al. |
| 5,017,714 A | 5/1991 | Welborn, Jr. |
| 5,026,798 A | 6/1991 | Canich |
| 5,057,475 A | 10/1991 | Canich et al. |
| 5,096,867 A | 3/1992 | Canich |
| 5,120,867 A | 6/1992 | Welborn, Jr. |
| 5,245,107 A | 9/1993 | Yon et al. |
| 5,264,405 A | 11/1993 | Canich |
| 5,278,119 A | 1/1994 | Turner et al. |
| 5,304,614 A | 4/1994 | Winter et al. |
| 5,324,800 A | 6/1994 | Welborn, Jr. et al. |
| 5,350,723 A | 9/1994 | Neithamer et al. |
| 5,365,003 A | 11/1994 | Chang et al. |
| 5,391,790 A | 2/1995 | Rohrmann et al. |
| 5,630,937 A | 5/1997 | Betz et al. |
| 5,719,322 A | 2/1998 | Lansbarkis et al. |
| 6,051,631 A | 4/2000 | Hottovy |
| 6,111,162 A | 8/2000 | Rossini et al. |

(Continued)

FOREIGN PATENT DOCUMENTS

| | | |
|---|---|---|
| CN | 101804335 A | 8/2010 |
| CN | 101980013 A | 2/2011 |

(Continued)

OTHER PUBLICATIONS

Landskron, K.;Hatton, B.D.; Perovic, D.D.; Ozin, G.A. Science Oct. 10, 2003, vol. 302, 266-269. (Year: 2003).*
Van Der Voort et al., "Periodic Mesoporous Organosilicas: from simple to complex bridges; a comprehensive overview of functions, morphologies and applications", Chemical Society Reviews, 2013, pp. 3913-3955, vol. 42, Royal Society of Chemistry.
Fujita et al., "Self-Organization of Organosilica solids with Molecular-Scale and Mesoscale Periodicities", Chemistry of Materials, Feb. 1, 2008, pp. 891-908, vol. 20, No. 3, ACS Publications.
PCT/US2015/065351 International Search Report and Written Opinion dated May 2, 2016.

(Continued)

*Primary Examiner* — Rip A Lee
(74) *Attorney, Agent, or Firm* — Lisa K. Holthus; Amanda K. Norwood

(57) ABSTRACT

This invention relates in certain aspects to a process for removing oxygenates from a stream, preferably a hydrocarbon stream comprising contacting an organosilica material with the hydrocarbon steam, where the organosilica material is a polymer of at least one monomer of Formula $[Z^1OZ^2SiCH_2]_3$, wherein $Z^1$ represents a hydrogen atom, a $C_1$-$C_4$ alkyl group, or a bond to a silicon atom of another monomer and $Z^2$ represents a hydroxyl group, a $C_1$-$C_4$ alkoxy group, a $C_1$-$C_6$ alkyl group or an oxygen atom bonded to a silicon atom of another monomer.

25 Claims, 5 Drawing Sheets

(56) References Cited

U.S. PATENT DOCUMENTS

| | | | |
|---|---|---|---|
| 6,118,037 | A | 9/2000 | Piccoli et al. |
| 6,632,766 | B2 | 10/2003 | Kanazirev |
| 6,790,344 | B1 | 9/2004 | Min et al. |
| 6,987,152 | B1 | 1/2006 | Eisinger et al. |
| 7,102,044 | B1 | 9/2006 | Kulprathipanja et al. |
| 7,141,630 | B2 | 11/2006 | Vizzini et al. |
| 7,141,632 | B2 | 11/2006 | Vaughan et al. |
| 7,300,905 | B2 | 11/2007 | Keefer et al. |
| 7,326,821 | B2 | 2/2008 | Risch et al. |
| 7,368,618 | B2 | 5/2008 | Kulprathipanja et al. |
| 7,497,965 | B2 | 3/2009 | Wariishi et al. |
| 7,538,065 | B2 | 5/2009 | McCarthy et al. |
| 7,576,248 | B2 | 8/2009 | Kulprathipanja et al. |
| 7,682,502 | B2 | 3/2010 | McCarthy et al. |
| 7,705,062 | B2 | 4/2010 | Markowitz et al. |
| 7,754,330 | B2 | 7/2010 | Hamada et al. |
| 7,767,620 | B2 | 8/2010 | Whitnall et al. |
| 7,947,799 | B2* | 5/2011 | Landskron ............ B01J 29/0308 528/35 |
| 8,110,692 | B2 | 2/2012 | Bellussi et al. |
| 8,211,498 | B2 | 7/2012 | Ku et al. |
| 8,277,600 | B2 | 10/2012 | Hamada et al. |
| 8,277,661 | B2 | 10/2012 | Sah et al. |
| 8,425,762 | B2 | 4/2013 | McCarthy et al. |
| 8,441,006 | B2 | 5/2013 | Michalak et al. |
| 8,470,074 | B2 | 6/2013 | Baugh et al. |
| 8,545,694 | B2 | 10/2013 | McCarthy et al. |
| 8,562,856 | B2 | 10/2013 | Giannantonio et al. |
| 8,568,520 | B2 | 10/2013 | Ohashi et al. |
| 8,598,070 | B1 | 12/2013 | Baugh et al. |
| 8,598,071 | B1 | 12/2013 | Baugh et al. |
| 8,809,561 | B2 | 8/2014 | Bellussi et al. |
| 9,034,079 | B2 | 5/2015 | Deckman et al. |
| 9,181,282 | B2 | 11/2015 | Ide et al. |
| 9,382,344 | B2 | 7/2016 | Ho et al. |
| 2002/0147377 | A1 | 10/2002 | Kanazirev |
| 2003/0188991 | A1 | 10/2003 | Shan et al. |
| 2004/0072972 | A1 | 4/2004 | Vizzini et al. |
| 2004/0254416 | A1* | 12/2004 | Risch ................... C07C 7/12 585/824 |
| 2005/0054885 | A1 | 3/2005 | Reyes et al. |
| 2005/0093189 | A1 | 5/2005 | Vo |
| 2006/0058565 | A1 | 3/2006 | De Wild |
| 2006/0070917 | A1 | 4/2006 | McCarthy et al. |
| 2007/0003492 | A1 | 1/2007 | Kitahata et al. |
| 2007/0034992 | A1 | 2/2007 | Wariishi et al. |
| 2007/0054136 | A1 | 3/2007 | Takahashi et al. |
| 2007/0112242 | A1 | 5/2007 | Edmiston |
| 2007/0173401 | A1 | 7/2007 | Landskron et al. |
| 2009/0130412 | A1 | 5/2009 | Hatton et al. |
| 2009/0215612 | A1 | 8/2009 | McCarthy et al. |
| 2009/0294922 | A1 | 12/2009 | Hamada et al. |
| 2010/0059181 | A1* | 3/2010 | Lee ................... H01J 37/32623 156/345.51 |
| 2010/0155302 | A1 | 6/2010 | Kaminsky et al. |
| 2010/0197989 | A1 | 8/2010 | Ducreux et al. |
| 2010/0233482 | A1 | 9/2010 | Hamada et al. |
| 2011/0079145 | A1 | 4/2011 | Dolan et al. |
| 2011/0139685 | A1 | 6/2011 | McCarthy et al. |
| 2011/0190115 | A1 | 8/2011 | Ciriminna et al. |
| 2012/0059181 | A1* | 3/2012 | Bellussi ................ C01B 37/00 556/10 |
| 2012/0160742 | A1 | 6/2012 | Sohn et al. |
| 2013/0075876 | A1 | 3/2013 | Goethals et al. |
| 2013/0078172 | A1 | 3/2013 | Bingbing et al. |
| 2013/0249049 | A1 | 9/2013 | Michalak et al. |
| 2014/0004358 | A1 | 1/2014 | Blackwell et al. |
| 2014/0186246 | A1 | 7/2014 | Calabro et al. |
| 2014/0208753 | A1 | 7/2014 | Liu et al. |
| 2015/0011787 | A1 | 1/2015 | Bellussi et al. |
| 2016/0167015 | A1* | 6/2016 | Podsiadlo ................ C08F 2/10 208/290 |
| 2016/0167016 | A1 | 6/2016 | Li et al. |
| 2016/0167032 | A1 | 6/2016 | Podsiadlo et al. |
| 2016/0168171 | A1 | 6/2016 | Li et al. |
| 2016/0168172 | A1 | 6/2016 | Li et al. |
| 2016/0168173 | A1 | 6/2016 | Li et al. |
| 2016/0168174 | A1 | 6/2016 | Li et al. |
| 2016/0168333 | A1* | 6/2016 | Podsiadlo ................ C08F 2/10 208/310 R |
| 2016/0168484 | A1 | 6/2016 | Weigel et al. |
| 2016/0168485 | A1 | 6/2016 | Li et al. |
| 2016/0229959 | A1 | 8/2016 | Li et al. |
| 2017/0306068 | A1 | 10/2017 | Holtcamp et al. |
| 2017/0320971 | A1 | 11/2017 | Holtcamp et al. |
| 2017/0320977 | A1 | 11/2017 | Holtcamp et al. |
| 2017/0327604 | A1 | 11/2017 | Holtcamp et al. |
| 2017/0354961 | A1 | 12/2017 | Podsiadlo et al. |
| 2017/0355822 | A1 | 12/2017 | Calabro et al. |
| 2017/0355823 | A1 | 12/2017 | Peterson et al. |
| 2018/0142066 | A1 | 5/2018 | Falkowski et al. |

FOREIGN PATENT DOCUMENTS

| | | |
|---|---|---|
| CN | 102052713 A | 5/2011 |
| CN | 102643429 A | 8/2012 |
| CN | 103495340 A | 1/2014 |
| CN | 103613975 A | 3/2014 |
| CN | 104117343 A | 10/2014 |
| CN | 103157362 A | 6/2016 |
| EP | 1995214 A2 | 11/2008 |
| JP | H10151343 A | 6/1998 |
| JP | H11295284 A | 10/1999 |
| JP | 2003167233 A | 6/2003 |
| JP | 2006083311 A | 3/2006 |
| JP | 2006095512 A | 4/2006 |
| JP | 2007070520 A | 3/2007 |
| JP | 2007238761 A | 9/2007 |
| JP | 2008045060 A | 2/2008 |
| JP | 2008062138 A | 3/2008 |
| JP | 2010100492 A | 5/2010 |
| JP | 2011025201 A | 2/2011 |
| JP | 2012149138 A | 8/2012 |
| JP | 2014057941 A | 4/2014 |
| JP | 5544672 B1 | 7/2014 |
| RU | 2291878 C1 | 1/2007 |
| WO | 9319103 A1 | 9/1993 |
| WO | 9610537 A1 | 4/1996 |
| WO | 03020671 A1 | 3/2003 |
| WO | 2004033507 A1 | 4/2004 |
| WO | 2006032140 A1 | 3/2006 |
| WO | 2007081212 A1 | 7/2007 |
| WO | 2011145933 A1 | 11/2011 |
| WO | 2013093022 A1 | 6/2013 |
| WO | 2014040512 A1 | 1/2014 |
| WO | 2014090757 A1 | 6/2014 |
| WO | 2014209813 A1 | 12/2014 |
| WO | 2015100198 A1 | 7/2015 |
| WO | 2016094784 A1 | 6/2016 |
| WO | 2016094803 A1 | 6/2016 |

OTHER PUBLICATIONS

Topchiev et al., "Preparation of hexa alkoxy derivatives of cyclotrimethylenesilane", Doklady Akademii Nauk SSSR, 1955, pp. 95-96. vol. 103.

Kriner, "The preparation of cyclic siliconmethylene compounds", Journal of Organic Chemistry, Jun. 1964, pp. 1601-1606, vol. 29.

Kuivila et al., "Trimethylsilyl-substituted norbornenes, norbornanes, and nortricyclene", Journal of Organic Chemistry, Oct. 1964, pp. 2845-2851, vol. 29.

Vidal-Madjar et al., "Fast Analysis of Geometrical Isomers of Complex Compounds by Gas-Solid Chromatography", Gas Chromatography, Sep. 28, 1970-Oct. 2, 1970, pp. 381-386.

Inagaki et al., "Novel Mesoporous Materials with a Uniform Distribution of Organic Groups and Inorganic Oxide in Their Frameworks", Journal of the American Chemical Society, Oct. 4, 1999, pp. 9611-9614, vol. 121.

Melde et al., "Mesoporous Sieves with Unified Hybrid Inorganic/Organic Frameworks", Chemistry of Materials, Oct. 9, 1999, pp. 3302-3308, vol. 11.

(56) References Cited

OTHER PUBLICATIONS

Grudzien et al., "Cage-like ordered mesoporous organosilicas with isocyanurate bridging groups: Synthesis, template removal and structural properties", Microporous and Mesoporous Materials, pp. 68-77, vol. 118, No. 1-3, 2008.
Walcarius et al., "Mesoporous organosilica adsorbents: nanoengineered materials for removal of organic and inorganic pollutants", Journal of Materials Chemistry, Jan. 1, 2010, pp. 4478-4511, vol. 20, No. 22.
"Vidal et al., ""Adsorption of polycyclic aromatic hydrocarbons from aqueous solutions by modified periodic mesoporous organosilica""", Journal of Colloid and Interface Science, Feb. 3, 2011, pp. 466-473, vol. 357, No. 2."
Grudzien et al., "Cage-like mesoporous organosilicas with isocyanurate bridging groups synthesized by soft templating with poly(ethylene oxide)-poly(butylene oxide)-poly(ethylene oxide) block copolymer", Journal of Colloid and Interface Science, May 1, 2009, pp. 354-362, vol. 333, No. 1, Elsevier.
Grudzien et al., "Periodic Mesoporous Organosilicas with Im3m Symmetry and Large Isocyanurate Bridging Groups", The Journal of Physical Chemistry B, Feb. 1, 2006, pp. 2972-2975, vol. 110, No. 7, ACS Publications.
Olkhovyk et al., "Periodic Mesoporous Organosilica with Large Heterocyclic Bridging Groups", Journal of American Chemical Society, Jan. 1, 2005, pp. 60-61, vol. 127, No. 1, ACS Publications.
"Poli et al., ""Different Routes for Preparing Mesoporous Organosilicas Containing the Troger's Base and Their Textural and Catalytic Implications""", The Journal of Physical Chemistry C, Apr. 21, 2011, pp. 7573-7585, vol. 115, No. 15, ACS Publications."
PCT/US2015/065208 International Search Report and Written Opinion dated May 17, 2016.
PCT/US2015/065200 Partial International Search Report and Written Opinion dated May 23, 2016.
"Diaz et al., ""Hybrid organic-inorganic catalytic porous materials synthesized at neutral pH in absence of structural directing agents""", Journal of Materials Chemistry, Jan. 1, 2009, pp. 5970-5979, vol. 19, No. 33, Royal Society of Chemistry."
Reale et al., "A fluoride-catalyzed sol-gel route to catalytically active non-ordered mesoporous silica materials in the absence of surfactants", Journal of Materials Chemistry, Jan. 1, 2005, pp. 1742-1754, vol. 15, No. 17, Royal Society of Chemistry.
PCT/US2015/065200 Partial International Search Report and Written Opinion dated Jul. 18, 2016.
Goethals et al., "Ultra-low-k cyclic carbon-bridged PMO films with a high chemical resistance", Journal of Materials chemistry, Feb. 21, 2012, pp. 8281-8286, vol. 22.
PCT/US2015/065258 Partial International Search Report and Written Opinion dated Mar. 16, 2016.
PCT/US2015/065194 International Search Report and Written Opinion dated Mar. 29, 2016.
PCT/US2015/065191 International Search Report and Written Opinion dated Mar. 29, 2016.
PCT/US2015/065306 International Search Report and Written Opinion dated Mar. 29, 2016.
PCT/US2015/065219 International Search Report and Written Opinion dated Apr. 5, 2016.
PCT/US2015/065283 International Search Report and Written Opinion dated Apr. 6, 2016.
PCT/US2015/065199 International Search Report and Written Opinion dated Apr. 8, 2016.
PCT/US2015/065204 International Search Report and Written Opinion dated Apr. 8, 2016.
PCT/US2015/065225 International Search Report and Written Opinion dated Apr. 8, 2016.
Harlick et al., "Applications of Pore-Expanded Mesoporous Silica. 5. Triamine Grafted Material with Exceptional CO2 Dynamic and Equilibrium Adsorption Performance", Industrial & Engineering Chemistry Research, Dec. 20, 2006, pp. 446-458 vol. 46.
Niemeyer et al., "Effects of CO2 Sorption on the Rotational Reorientation Dynamics of a Model Solute Dissolved in Molten Poly(dimethylsiloxane)", Macromolecules, Jan. 13, 1998, pp. 77-85, vol. 31.
Eliseeva et al., "Antifoaming additive for alkaline absorption solutions for removal of carbon dioxide from synthesis gas", Khimicheskaya Promyshlennost, 1999, pp. 632-633, vol. 10.
Brondani et al., "Polyfunctional carbosilanes and organosilicon compounds. Synthesis via Grignard reactions", Tetrahedron Letters, 1993, pp. 2111-2114, vol. 34.
Gilman et al., "Reactions of triphenylsilyllithium with some dichloropropenes", Journal of Organometallic Chemistry, Apr. 13, 2001, pp. 293-303, vol. 2.
Goethals, et al., "A new procedure to seal the pores of mesoporous low-k films with precondensed organosilica oligomers", Chemical Communications, 2012, pp. 2797-2799, vol. 48, No. 22, Royal Society of Chemistry.
Goethals et al., "Sealed ultra low-k organosilica films with improved electrical, mechanical and chemical properties", Journal of Materials Chemistry C, 2013, vol. 1, No. 25, Royal Society of Chemistry.
Goethals et al., "Hydrophobic high quality ring PMOs with an extremely high stability", Journal of Materials Chemistry, 2010, pp. 1709-1716, vol. 20, No. 9, Royal Society of Chemistry.
Landskron et al., "Periodic Mesoporous Organosilicas: Self-Assembly from Bridged Cyclic Silsesquioxane Precursors", Angewandte Chemie, International Edition, 2005, pp. 2107-2109, vol. 44, No. 14, Wiley-VCH Verlag GmbH & Co. KgaA.
Landskron et al., "Periodic Mesoporous Organosilicas Containing Interconnected [Si(CH2)]3 Rings", Science, Oct. 10, 2003, pp. 266-269, vol. 302.
Bahuleyan et al., "One-pot synthesis of spherical periodic mesoporous organosilica supported catalyst bearing Ni(II) α-diimine complexes for ethylene polymerization", Catalysis Communications, 2009, pp. 252-256, vol. 11.

* cited by examiner

ORGANOSILICA MATERIALS FOR USE AS ADSORBENTS FOR OXYGENATE REMOVAL

PRIORITY

This application is a National Stage Application of International Application No. PCT/US2015/065351, filed Dec. 11, 2015 and claims the benefit of and priority to U.S. Provisional Application No. 62/091,071 filed on Dec. 12, 2014 and U.S. Provisional Application No. 62/091,077 filed on Dec. 12, 2014. The entire disclosures of each of the above applications are fully incorporated herein by reference.

This application is related to U.S. Ser. No. 14/311,171, filed Jun. 20, 2014, which claims the benefit of priority to U.S. Provisional Application No. 61/838,919, filed Jun. 25, 2013, the disclosures of which are fully incorporated herein by reference.

FIELD OF THE INVENTION

The present disclosure relates to processes for reducing certain oxygenate contaminates in a process stream of a polymerization reactor, and in particular, to reducing $C_1$ to $C_{40}$ oxygenates in a recycle stream of an olefin polymerization reactor where diene monomers are present by using an organosilica material as an adsorbent.

BACKGROUND OF THE INVENTION

This section provides background information related to the present disclosure which is not necessarily prior art.

Certain polymerization processes, especially olefin polymerization processes, are sensitive to poisons that can reduce the catalyst activity. There are commercially available adsorbents that can be used to treat the various streams of materials going into the polymerization reactor. For example, WO 2004/033507 discloses that dual adsorbents can be used to remove impurities from a cycle stream in a polymerization process. However, in conjunction with the inventive activities, it has been surprisingly found that certain non-conjugated diene monomers may react with components of the polymerization reactor to form undesirable oxygenates. It would be desirable to reduce or eliminate such oxygenates that otherwise poison the catalyst.

Porous inorganic solids have found great utility as catalysts and separation media for industrial application. In particular, mesoporous materials, such as silicas and aluminas, having a periodic arrangement of mesopores are attractive materials for use in adsorption, separation and catalytic processes due to their uniform and tunable pores, high surface areas and large pore volumes. The pore structure of such mesoporous materials is large enough to adsorb large molecules and the pore wall structure can be as thin as about 1 nm. Further, such mesoporous materials are known to have large specific surface areas (e.g., 1000 $m^2/g$) and large pore volumes (e.g., 1 cc/g). For these reasons, such mesoporous materials enable reactive catalysts, adsorbents composed of a functional organic compound, and other molecules to rapidly diffuse into the pores and therefore, can be advantageous over zeolites, which have smaller pore sizes. Consequently, such mesoporous materials can be useful not only for catalysis of high-speed catalytic reactions, but also as large capacity adsorbents.

Mesoporous organosilica (MOS) supports are conventionally formed by the self-assembly of the silsequioxane precursor in the presence of a structure directing agent, porogen and/or framework element. The precursor is hydrolysable and condenses around the structure directing agent. For example, Landskron, K., et al. report the self-assembly of 1,3,5-tris[diethoxysila]cylcohexane [$(EtO)_2SiCH_2]_3$ in the presence of a base and the structure directing agent, cetyltrimethylammonium bromide. Landskron, K., et al., Science, 302:266-269 (2003).

US2012/0059181 reports the preparation of a crystalline hybrid organic-inorganic silicate formed from 1,1,3,3,5,5 hexaethoxy-1,3,5 trisilyl cyclohexane in the presence of $NaAlO_2$ and base. US2007/003492 reports preparation of a composition formed from 1,1,3,3,5,5 hexaethoxy-1,3,5 trisilyl cyclohexane in the presence of propylene glycol monomethyl ether. U.S. Pat. No. 7,947,799 discloses high organic group content-periodic mesoporous organosilicas having [ER]$_n$ rings interconnected by E' atoms, where n is greater than 1, and E and E' are inorganic elements. Voort V. et al., report in Periodic Mesoporous Organosilicas: From Simple to Complex Bridges; A Comprehensive Overview of Functions, Morphologies and Applications various periodic mesoporous organosilicas and mentions, at paragraph 4.1.3, bridges of Ni(II) alpha-diimine complexes showed high activity in the ethylene polymerization at a wider range of temperatures than the homogeneous complexes (see Chem. Soc. Rev., 2013, 42, 3913).

However, the use of a structure directing agent, such as a surfactant, in the preparation of an organosilica material, such as a MOS, requires a more complicated, energy intensive process that limits the ability to scale-up the process for industrial applications. Furthermore, introduction of additional agents or processing steps to remove structure directing agents from MOS can introduce additional reactive and undesirable compositions into the system, potentially leading to additional species or catalyst poisoning. Therefore, there is a need to provide an organosilica materials having desirable pore size, pore volume and surface area, which can be prepared in the absence of a structure directing agent, a porogen and/or a framework element (aside from C, O, Si and hydrogen). Such materials will be described further herein. For more information, see also, U.S. Provisional Application No. 62/091,071 filed on Dec. 12, 2014 and U.S. Provisional Application No. 62/091,077 filed on Dec. 12, 2014, the disclosures of which were fully incorporated herein by reference above.

SUMMARY OF THE INVENTION

This invention relates in certain aspects to a process for removing oxygenates from a stream, preferably a hydrocarbon stream comprising contacting an organosilica material with the hydrocarbon steam, where the organosilica material is a polymer of at least one monomer of Formula $[Z^1OZ^2SiCH_2]_3$, wherein $Z^1$ represents a hydrogen atom, a $C_1$-$C_4$ alkyl group, or a bond to a silicon atom of another monomer and $Z^2$ represents a hydroxyl group, a $C_1$-$C_4$ alkoxy group, a $C_1$-$C_6$ alkyl group or an oxygen atom bonded to a silicon atom of another monomer.

This disclosure further relates to a process for polymerization comprising providing a recycle stream, wherein the recycle stream comprises one or more one or more $C_1$ to $C_{40}$ oxygenates (and optionally one or more $C_6$ to $C_{12}$ conjugated or non-conjugated diene monomers); contacting at least a portion of the recycle stream with an adsorbent bed to produce a treated recycle stream, where the adsorbent bed comprises adsorbent comprising an organosilica material to remove excess quenching agent and/or $C_1$ to $C_{40}$ oxygenates; contacting the treated recycle stream with polymerization catalyst to produce a polyolefin product stream; quenching the polyolefin product stream with a quenching agent selected from water and/or a $C_1$ to $C_8$ alcohol; and separating the quenched polyolefin stream into a polyolefin product and the recycle stream.

BRIEF DESCRIPTION OF THE FIGURES

Corresponding reference numerals indicate corresponding parts throughout the several views of the drawings.

DETAILED DESCRIPTION

Figure 1:
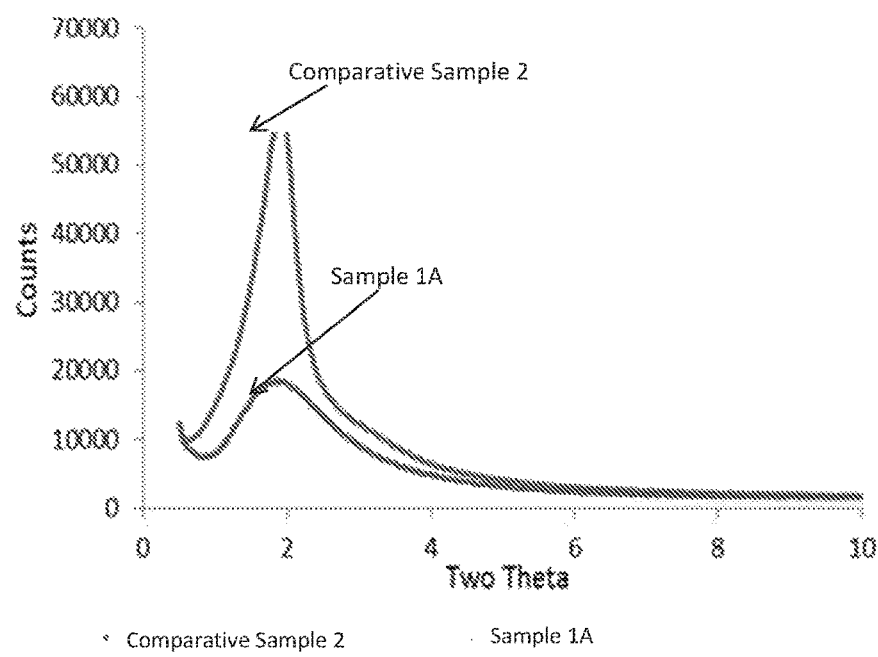
FIG. 1 illustrates an X-Ray Diffraction (XRD) spectrum for Sample 1A and Comparative Sample 2.

In certain aspects, the present disclosure is directed to the reduction or elimination of oxygenates and or catalyst poisons from a stream, preferably a hydrocarbon stream, preferably a recycle stream, entering a polyolefin polymerization reactor.

In particular, in the production of polymers that include conjugated or non-conjugated diene monomers, such as ethylidene norbornene, it has been discovered that during the quenching of the reaction product and subsequent removal of quenching agent, such as water, with molecular sieves, that undesirable organic oxygenates ("oxygenates," including aldehydes, carboxylates, alcohols, ketones, esters, and ethers) are formed that later find their way into the polymerization reactor in the recycle stream and reduce the catalyst activity. In accordance with certain aspects of the present disclosure, the inventors have found that certain organosilica materials, such as certain mesoporous organosilica material, or alternatively a combination of adsorbents comprising select organosilica materials, preferably solid adsorbents, remove the quenching agent as well as the higher molecular weight oxygenates from the recycle stream entering the reactor.

I. DEFINITIONS

For purposes of this invention and the claims hereto, the numbering scheme for the Periodic Table Groups is according to the IUPAC Periodic Table of Elements.

The terms "substituent," "radical," "group," and "moiety" may be used interchangeably.

The term "$C_n$" means hydrocarbon(s) having n carbon atom(s) per molecule, wherein n is a positive integer.

The term "hydrocarbon" means a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different values of n.

The term "alkyl" refers to a saturated hydrocarbon radical having from 1 to 12 carbon atoms (i.e., $C_1$-$C_{12}$ alkyl), particularly from 1 to 8 carbon atoms (i.e., $C_1$-$C_8$ alkyl), particularly from 1 to 6 carbon atoms (i.e., $C_1$-$C_6$ alkyl), and particularly from 1 to 4 carbon atoms (i.e., $C_1$-$C_4$ alkyl). Examples of alkyl groups include, but are not limited to, methyl, ethyl, propyl, butyl, pentyl, hexyl, heptyl, octyl, decyl, and so forth. The alkyl group may be linear, branched or cyclic. "Alkyl" is intended to embrace all structural isomeric forms of an alkyl group. For example, as used herein, propyl encompasses both n-propyl and isopropyl; butyl encompasses n-butyl, sec-butyl, isobutyl and tert-butyl and so forth. As used herein, "$C_1$ alkyl" refers to methyl ($-CH_3$), "$C_2$ alkyl" refers to ethyl ($-CH_2CH_3$), "$C_3$ alkyl" refers to propyl ($-CH_2CH_2CH_3$) and "$C_4$ alkyl" refers to butyl (e.g., $-CH_2CH_2CH_2CH_3$, $-(CH_3)CHCH_2CH_3$, $-CH_2CH(CH_3)_2$, etc.). Further, as used herein, "Me" refers to methyl, and "Et" refers to ethyl, "i-Pr" refers to isopropyl, "t-Bu" refers to tert-butyl, and "Np" refers to neopentyl.

The term "alkylene" refers to a divalent alkyl moiety containing 1 to 12 carbon atoms (i.e., $C_1$-$C_{12}$ alkylene) in length and meaning the alkylene moiety is attached to the rest of the molecule at both ends of the alkyl unit. For example, alkylenes include, but are not limited to, $-CH_2-$, $-CH_2CH_2-$, $-CH(CH_3)CH_2-$, $-CH_2CH_2CH_2-$, etc. The alkylene group may be linear or branched.

The term "nitrogen-containing alkyl" refers to an alkyl group as defined herein wherein one or more carbon atoms in the alkyl group is substituted with a nitrogen atom or a nitrogen-containing cyclic hydrocarbon having from 2 to 10 carbon atoms (i.e., a nitrogen-containing cyclic $C_2$-$C_{10}$ hydrocarbon), particularly having from 2 to 5 carbon atoms (i.e., a nitrogen-containing cyclic $C_2$-$C_5$ hydrocarbon), and particularly having from 2 to 5 carbon atoms (i.e., a nitrogen-containing cyclic $C_2$-$C_5$ hydrocarbon). The nitrogen-containing cyclic hydrocarbon may have one or more nitrogen atoms. The nitrogen atom(s) may optionally be substituted with one or two $C_1$-$C_6$ alkyl groups. The nitrogen-containing alkyl can have from 1 to 12 carbon atoms (i.e., $C_1$-$C_{12}$ nitrogen-containing alkyl), particularly from 1 to 10 carbon atoms (i.e., $C_1$-$C_{10}$ nitrogen-containing alkyl), particularly from 2 to 10 carbon atoms (i.e., $C_2$-$C_{10}$ nitrogen-containing alkyl), particularly from 3 to 10 carbon atoms (i.e., $C_3$-$C_{10}$ nitrogen-containing alkyl), and particularly from 3 to 8 carbon atoms (i.e., $C_1$-$C_{10}$ nitrogen-containing alkyl). Examples of nitrogen-containing alkyls include, but are not limited to,

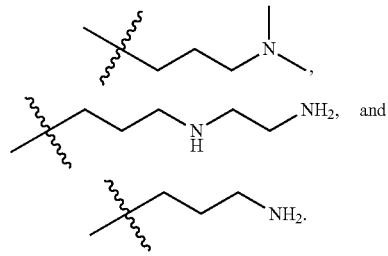

The term "nitrogen-containing alkylene" refers to an alkylene group as defined herein wherein one or more carbon atoms in the alkyl group is substituted with a nitrogen atom. The nitrogen atom(s) may optionally be substituted with one or two $C_1$-$C_6$ alkyl groups. The nitrogen-containing alkylene can have from 1 to 12 carbon atoms (i.e., $C_1$-$C_{12}$ nitrogen-containing alkylene), particularly from 2 to 10 carbon atoms (i.e., $C_2$-$C_{10}$ nitrogen-containing alkylene), particularly from 3 to 10 carbon atoms (i.e., $C_3$-$C_{10}$ nitrogen-containing alkylene), particularly from 4 to 10 carbon atoms (i.e., $C_4$-$C_{10}$ nitrogen-containing alkylene), and particularly from 3 to 8 carbon atoms (i.e., $C_3$-$C_8$ nitrogen-containing alkyl). Examples of nitrogen-containing alkylenes include, but are not limited to,

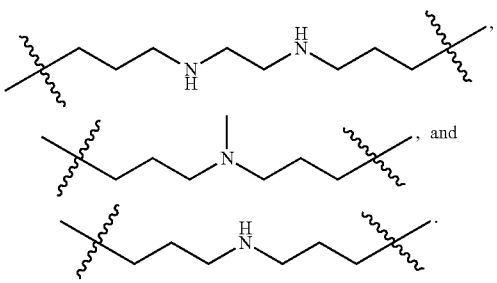

The term "alkenyl" refers to an unsaturated hydrocarbon radical having from 2 to 12 carbon atoms (i.e., $C_2$-$C_{12}$ alkenyl), particularly from 2 to 8 carbon atoms (i.e., $C_2$-$C_8$ alkenyl), particularly from 2 to 6 carbon atoms (i.e., $C_2$-$C_6$ alkenyl), and having one or more (e.g., 2, 3, etc.) carbon-carbon double bonds. The alkenyl group may be linear, branched or cyclic. Examples of alkenyls include, but are not limited to ethenyl (vinyl), 2-propenyl, 3-propenyl, 1,4-pentadienyl, 1,4-butadienyl, 1-butenyl, 2-butenyl and 3-butenyl. "Alkenyl" is intended to embrace all structural isomeric forms of an alkenyl. For example, butenyl encompasses 1,4-butadienyl, 1-butenyl, 2-butenyl and 3-butenyl, etc.

The term "alkenylene" refers to a divalent alkenyl moiety containing 2 to about 12 carbon atoms (i.e., $C_2$-$C_{12}$ alkenylene) in length and meaning that the alkylene moiety is attached to the rest of the molecule at both ends of the alkyl unit. For example, alkenylenes include, but are not limited to, —CH=CH—, —CH=CHCH$_2$—, —CH=CH—CH—, —CH$_2$CH$_2$CH=CHCH$_2$—, etc. The alkenylene group may be linear or branched.

The term "alkynyl" refers to an unsaturated hydrocarbon radical having from 2 to 12 carbon atoms (i.e., $C_2$-$C_{12}$ alkynyl), particularly from 2 to 8 carbon atoms (i.e., $C_2$-$C_8$ alkynyl), particularly from 2 to 6 carbon atoms (i.e., $C_2$-$C_6$ alkynyl), and having one or more (e.g., 2, 3, etc.) carbon-carbon triple bonds. The alkynyl group may be linear, branched or cyclic. Examples of alkynyls include, but are not limited to ethynyl, 1-propynyl, 2-butynyl, and 1,3-butadiynyl. "Alkynyl" is intended to embrace all structural isomeric forms of an alkynyl. For example, butynyl encompasses 2-butynyl, and 1,3-butadiynyl and propynyl encompasses 1-propynyl and 2-propynyl (propargyl).

The term "alkynylene" refers to a divalent alkynyl moiety containing 2 to about 12 carbon atoms (i.e., $C_2$-$C_{12}$ alkenylene) in length and meaning that the alkylene moiety is attached to the rest of the molecule at both ends of the alkyl unit. For example, alkenylenes include, but are not limited to, —C≡C—, —C≡CCH$_2$—, —C≡CCH$_2$C≡C—, —CH$_2$CH$_2$C≡CCH$_2$—, etc. The alkynylene group may be linear or branched.

The term "alkoxy" refers to —O— alkyl containing from 1 to about 10 carbon atoms. The alkoxy may be straight-chain or branched-chain. Non-limiting examples include methoxy, ethoxy, propoxy, butoxy, isobutoxy, tert-butoxy, pentoxy, and hexoxy. "$C_1$ alkoxy" refers to methoxy, "$C_2$ alkoxy" refers to ethoxy, "$C_3$ alkoxy" refers to propoxy and "$C_4$ alkoxy" refers to butoxy. Further, as used herein, "OMe" refers to methoxy and "OEt" refers to ethoxy.

The term "aromatic" refers to unsaturated cyclic hydrocarbons having a delocalized conjugated π system and having from 5 to 20 carbon atoms (aromatic $C_5$-$C_{20}$ hydrocarbon), particularly from 5 to 12 carbon atoms (aromatic $C_5$-$C_{12}$ hydrocarbon), and particularly from 5 to 10 carbon atoms (aromatic $C_5$-$C_{12}$ hydrocarbon). Exemplary aromatics include, but are not limited to benzene, toluene, xylenes, mesitylene, ethylbenzenes, cumene, naphthalene, methylnaphthalene, dimethylnaphthalenes, ethylnaphthalenes, acenaphthalene, anthracene, phenanthrene, tetraphene, naphthacene, benzanthracenes, fluoranthrene, pyrene, chrysene, triphenylene, and the like, and combinations thereof. Additionally, the aromatic may comprise one or more heteroatoms. Examples of heteroatoms include, but are not limited to, nitrogen, oxygen, and/or sulfur. Aromatics with one or more heteroatom include, but are not limited to furan, benzofuran, thiophene, benzothiophene, oxazole, thiazole and the like, and combinations thereof. The aromatic may comprise monocyclic, bicyclic, tricyclic, and/or polycyclic rings (in some embodiments, at least monocyclic rings, only monocyclic and bicyclic rings, or only monocyclic rings) and may be fused rings.

The term "aryl" refers to any monocyclic or polycyclic cyclized carbon radical containing 6 to 14 carbon ring atoms, wherein at least one ring is an aromatic hydrocarbon. Examples of aryls include, but are not limited to phenyl, naphthyl, pyridinyl, and indolyl.

The term "aralkyl" refers to an alkyl group substituted with an aryl group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of aralkyl groups include, but are not limited to phenymethyl, phenylethyl, and naphthylmethyl. The aralkyl may comprise one or more heteroatoms and be referred to as a "heteroaralkyl." Examples of heteroatoms include, but are not limited to, nitrogen (i.e., nitrogen-containing heteroaralkyl), oxygen (i.e., oxygen-containing heteroaralkyl), and/or sulfur (i.e., sulfur-containing heteroaralkyl). Examples of heteroaralkyl groups include, but are not limited to, pyridinylethyl, indolylmethyl, furylethyl, and quinolinylpropyl.

The term "heterocyclo" refers to fully saturated, partially saturated or unsaturated or polycyclic cyclized carbon radical containing from 4 to 20 carbon ring atoms and containing one or more heteroatoms atoms. Examples of heteroatoms include, but are not limited to, nitrogen (i.e., nitrogen-containing heterocyclo), oxygen (i.e., oxygen-containing heterocyclo), and/or sulfur (i.e., sulfur-containing heterocyclo). Examples of heterocyclo groups include, but are not limited to, thienyl, furyl, pyrrolyl, piperazinyl, pyridyl, benzoxazolyl, quinolinyl, imidazolyl, pyrrolidinyl, and piperidinyl.

The term "heterocycloalkyl" refers to an alkyl group substituted with heterocyclo group. The alkyl group may be a $C_1$-$C_{10}$ alkyl group, particularly a $C_1$-$C_6$, particularly a $C_1$-$C_4$ alkyl group, and particularly a $C_1$-$C_3$ alkyl group. Examples of heterocycloalkyl groups include, but are not limited to thienylmethyl, furylethyl, pyrrolylmethyl, piperazinylethyl, pyridylmethyl, benzoxazolylethyl, quinolinylpropyl, and imidazolylpropyl.

The term "hydroxyl" refers to an —OH group.

The term "oxygenate" refers to a saturated, unsaturated, or polycyclic cyclized hydrocarbon radical containing from 1 to 40 carbon atoms and further containing one or more oxygen heteroatoms.

The term, "aluminum alkyl adducts" refers to the reaction product of aluminum alkyls and/or alumoxanes with quenching agents, such as water and/or methanol.

The term "adsorption" includes physisorption, chemisorption, and condensation onto a solid material and combinations thereof.

The term "adsorbent bed" refers to a collection of materials, solid, liquid, pre-product, or other physical form for adsorbing one or more constituents from a material stream.

The term "mesoporous" refers to solid materials having pores that have a diameter within the range of from about 2 nm to about 50 nm.

The term "organosilica" refers to an organosiloxane compound that comprises one or more organic groups bound to two or more Si atoms.

The term "silanol" refers to a Si—OH group and the term "silanol content" refers to the percent of the Si—OH groups in a compound and can be calculated by standard methods, such as NMR.

The terms "structure directing agent," "SDA," and/or "porogen" refer to one or more compounds added to the synthesis media to aid in and/or guide the polymerization and/or polycondensing and/or organization of the building blocks that form the organosilica material framework. Further, a "porogen" is understood to be a compound capable of forming voids or pores in the resultant organosilica material framework. As used herein, the term "structure directing agent" encompasses and is synonymous and interchangeable with the terms "templating agent" and "template."

This invention relates to a process for removing oxygenates from a stream (preferably, a hydrocarbon stream, preferably a recycle stream), comprising contacting an organosilica material with the stream (preferably a hydrocarbon steam, preferably a $C_1$ to $C_{100}$ hydrocarbon, alternatively a $C_2$ to $C_{20}$ olefin monomer stream, preferably one or more of ethylene, propylene, butene, pentene, hexene, heptene, octene, nonene, decene, undecene, dodecene and isomers thereof, alternatively a $C_4$ to $C_{20}$ diolefin monomer stream, preferably one or more of butadiene, pentadiene, hexadiene, heptadiene, octadiene, nonadiene, decadiene and isomers thereof, alternatively a combination of any of olefin monomer and/or diene monomer and/or hydrocarbon stream. The organosilica material may be a polymer of at least one monomer of Formula $[Z^1OZ^2SiCH_2]_3$, wherein $Z^1$ represents a hydrogen atom, a $C_1$-$C_4$ alkyl group, or a bond to a silicon atom of another monomer and $Z^2$ represents a hydroxyl group, a $C_1$-$C_4$ alkoxy group, a $C_1$-$C_6$ alkyl group or an oxygen atom bonded to a silicon atom of another monomer.

This invention further relates to a process for polymerization comprising providing a recycle stream, wherein the recycle stream comprises one or more one or more $C_1$ to $C_{40}$ oxygenates (and optionally one or more $C_6$ to $C_{12}$ conjugated or non-conjugated diene monomers); contacting at least a portion of the recycle stream with an adsorbent bed to produce a treated recycle stream, where the adsorbent bed comprises adsorbent comprising an organosilica material to remove excess quenching agent and/or $C_1$ to $C_{40}$ oxygenates; contacting the treated recycle stream with polymerization catalyst to produce a polyolefin product stream; quenching the polyolefin product stream with a quenching agent selected from water and/or a $C_1$ to $C_8$ alcohol; and separating the quenched polyolefin stream into a polyolefin product and the recycle stream. The organosilica material may be a polymer of at least one monomer of Formula $[Z^1OZ^2SiCH_2]_3$, wherein $Z^1$ represents a hydrogen atom, a $C_1$-$C_4$ alkyl group, or a bond to a silicon atom of another monomer and $Z^2$ represents a hydroxyl group, a $C_1$-$C_4$ alkoxy group, a $C_1$-$C_6$ alkyl group or an oxygen atom bonded to a silicon atom of another monomer. In embodiments where the quenching agent comprises water, desirable adsorbents for removing water from the recycle stream include molecular sieves which comprise zeolitic materials, and desirable adsorbents for removing the oxygenates, especially $C_8$ to $C_{20}$ oxygenates, include one or more of a hybrid zeolitic material in alumina, a high purity silica, or another alumina adsorbent in addition to the organosilica material.

Preferably the adsorbent bed comprises at least two adsorbents, at least one of which is an organosilica material, to remove excess quenching agent and/or $C_1$ to $C_{40}$ oxygenates.

II. PURIFICATION OF POLYMERIZATION PROCESS STREAMS

Described herein is a process for polymerization comprising providing a reactor effluent, such as a polyolefin product stream, that is "washed" or "quenched" with a quenching agent selected from water, a $C_1$-$C_8$ alcohol (preferably methanol, ethanol, propanol, and/or octanol), and mixtures thereof, to produce a quenched polyolefin stream, which is then separated into a polyolefin product and a recycle stream. At least a portion of the recycle stream, preferably all of the recycle stream, that contains quenching agent, unreacted monomers, such as one or more $C_6$-$C_{12}$ diene monomers (conjugated or non-conjugated), and one or more $C_1$-$C_{40}$ oxygenates, or $C_4$-$C_{30}$ oxygenates, is contacted with an adsorbent bed to produce a treated recycle stream, which is then contacted with polymerization catalyst to produce a polyolefin product stream, where the cycle can then be repeated. Desirably, the adsorbent bed comprises organosilica material, preferably the adsorbent bed comprises at least two adsorbents, at least one of which is an organosilica material to remove excess quenching agent and/or $C_1$-$C_{40}$ oxygenates, or $C_4$-$C_{30}$ oxygenates, or $C_5$-$C_{20}$ oxygenates, or $C_9$-$C_{18}$ oxygenates.

The oxygenate in the recycle stream may derive from many sources. As a particular example of a source, the oxygenate in the recycle stream is the reaction product of a $C_6$-$C_{12}$ conjugated or non-conjugated diene monomer, the quenching agent, and an aluminum alkyl adduct from the polymerization reaction. For example, the combination of an acidic environment and the dienes and water will generate oxygenates, in particular, $C_5$-$C_{20}$ oxygenates, or $C_9$-$C_{18}$ oxygenates. The oxygenates, in some aspects, may also derive from the reaction of the $C_6$-$C_{12}$ conjugated or non-conjugated diene monomer with the adsorbent, such as a zeolitic material, used to remove the quenching agent from the recycle stream. For example, the $C_6$-$C_{12}$ conjugated or non-conjugated diene monomer may react with the acidic environment of the binder in the adsorbent, such as a zeolitic material, to form oxygenates.

The oxygenate in the recycle stream may depend on the type of quenching agent and the diene being used. For example, the recycle stream may comprise a $C_{m+n}$ oxygenate, where m is the number of carbon atoms from the quenching agent and n is the number of carbon atoms in the conjugated diene monomer, the dimer of the conjugated monomer, and oligomers of either with ethylene and/or propylene. Therefore, m is 0 if the quenching agent is water and when the quenching agent is a $C_{1-8}$ alcohol, m is an integer from 1 to 8 corresponding to the number of carbons in the alcohol used (e.g., if methanol is used m=1, if propanol is used m=3, if octanol is used m=8). Therefore, when the diene is ethylidene norbornene, n is typically equal to 9 or 18. Thus, when the diene is ethylidene norbornene or an ENB-isomer and water is used as the quenching agent, the recycle stream may comprise $C_9$ and/or $C_{18}$ oxygenates. Alternatively, when the diene is ethylidene norbornene or an ENB-isomer and methanol is used as the quenching agent, the recycle stream may comprise $C_{10}$ and/or $C_{19}$ oxygenates. Likewise, if the diene is ethylidene norbornene or an ENB-isomer and propanol is used as the quenching agent, the recycle stream may comprise $C_{12}$ and/or $C_{21}$ oxygenates.

The "quenching" step preferably takes place in a vessel or reactor separate from the adsorbent bed. This process is well known in the art and refers to the contacting of the quenching agent with the reactor effluent, wherein both the quenching agent and reactor effluent can be in the liquid state, the vapor state, or where one may be a liquid and the other a vapor. This process is used to control temperature of the effluent as well as stop the polymerization process, and may further include separating out the various components in the reactor effluent. Desirably, the polymer is separated out from the polyolefin product stream, leaving the recycle stream that is contacted with the at least two adsorbents in order to remove the residual quenching agent and oxygenates. A high pressure separator may be used before this step to remove a portion of the quenching agent and oxygenates, leaving the adsorbent bed to remove the remainder of the quenching agent and oxygenates.

The adsorbent bed is used to contact the reactant or recycle stream of materials that will include the undesirable oxygenate(s). Preferably, the adsorbent bed includes organosilica material that is stationary or otherwise fixed in the bed. Preferably, the adsorbent bed includes at least two, preferably two or three, adsorbents that are stationary or otherwise fixed in the bed. Thus, in various aspects, the adsorbent bed includes organosilica material and one or more additional adsorbents. The adsorbents may be in the form of particles, which may be ground to a desired particle size. The adsorbents may be spherical or cylindrical particles. The adsorbents may have an average particle size of from greater than or equal to about 0.001 mm (1 micrometer) to less than or equal to about 6 mm, optionally within the range of from about 0.01 mm (10 micrometers) or about 0.05 mm (50 micrometers) or about 0.1 mm (100 micrometers) or about 0.5 mm (500 micrometers) or about 1 mm or about 2 mm to about 2.5 mm or about 3 mm or about 4 mm or about 5 mm or about 6 mm, where desirable ranges may include ranges from any lower limit to any upper limit. The phrase "at least two adsorbents" means that there are two or more, preferably two or three, adsorbents that are distinct from one another in size and/or chemical composition and their ability and capacity to adsorb quenching agent, oxygenates, or even the desirable monomers used in the polymerization process. Desirably, the adsorbents will preferentially adsorb the oxygenates and quenching agent and allow the monomers to pass through the bed without being retained in or transformed over the bed.

Figure 6:
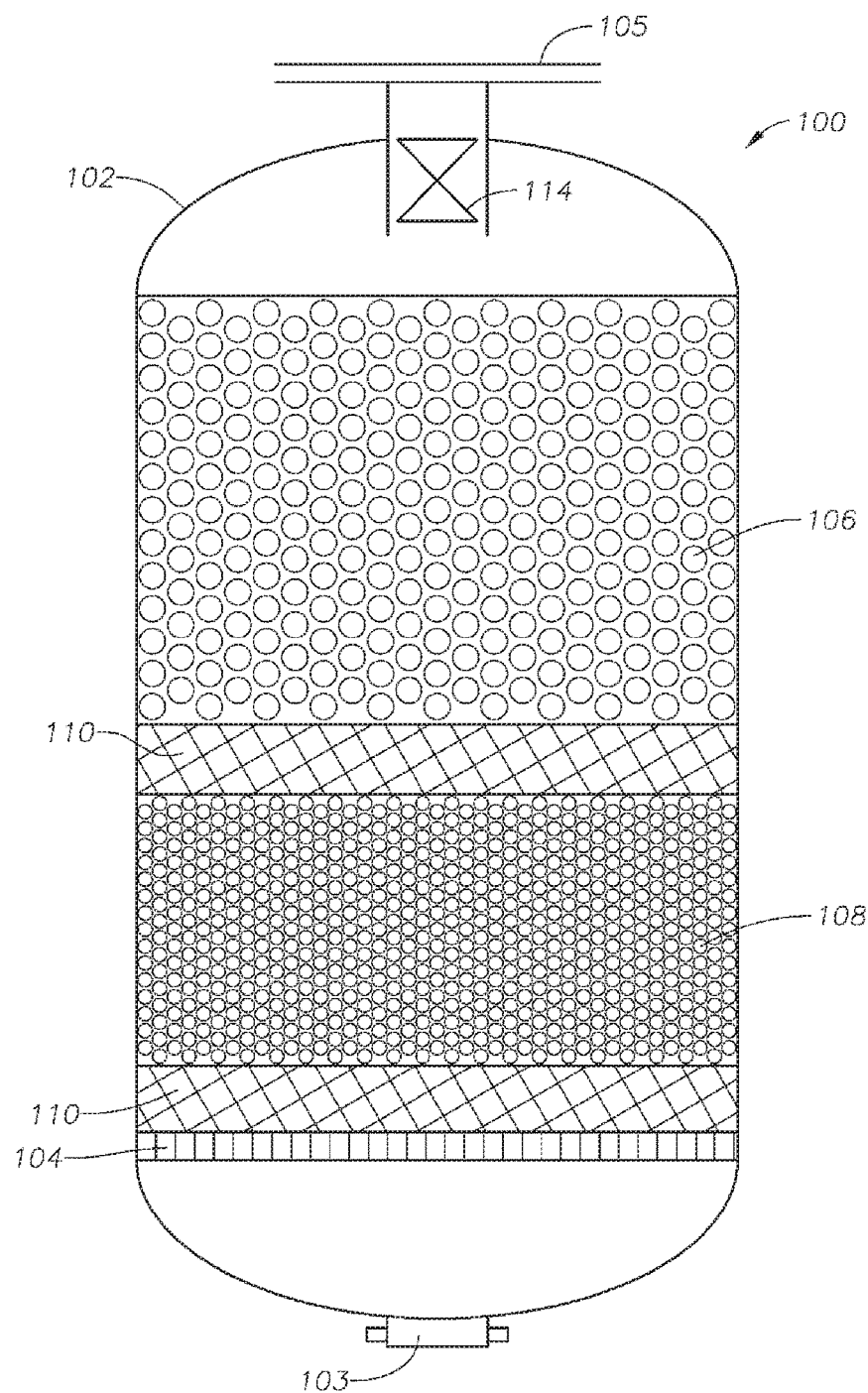
FIG. 6 is a cutaway schematic of an example adsorbent bed.

An example of how an adsorbent bed may be housed and situated is represented in FIG. 6. Preferably, the recycle stream flows through conduit (105) that passes through the bed (100) does so on a continuous basis, or batchwise, meaning that a volume of recycle stream may enter the bed and stay for some time in contact with the bed before then being flushed out. The bed may contain the two, or three, or more adsorbents intimately mixed together or in separate zones. For example, the bed may contain two adsorbents (106) and (108) arranged in separate zones as illustrated in FIG. 6. Even further, the two, three, or more adsorbents may be separated from one another by glass, ceramic or metal "frits" or screens (110), but otherwise be in liquid communication with one another, meaning that the recycle stream, which may include not only the oxygenates and quenching agent but unreacted monomers from the polymerization process and diluent, such as hexane and/or propane, that may be used during polymerization, can flow continuously from one zone of adsorbent to another. A porous tray (104) may be used to support the adsorbent bed (100) containing adsorbents (106) and (108) or other additional zones, so the diluent carrying the unreacted monomers, oxygenates, water and residual catalyst and activator materials (e.g., aluminum alkyl adducts described below) are carried intermittently or continuously from conduit (105), through port valve (114) into the bed (100) through adsorbent (106), past screen (110), then through the second adsorbent (108), then through the second screen (110) and out the bed (100) through port (103). The port valve (114) can control the flow of recycle stream into and through the adsorbent bed (100), and port (103) could also be fitted with a valve, and the flow can be either gravity driven or driven by internally generated pressure. Either or both of valves (103) and/or (114) could be fitted with filters to capture any solids. Most preferably, adsorbent (108) is the adsorbent primarily for removing one or more oxygenates, and the adsorbent (106) is the adsorbent primarily for removing quenching agent from the recycle stream. Stated another way, the first zone to be contacted by recycle stream is preferably the adsorbent primarily for removing quenching agent, such as water, preferably molecular sieve and/or alumina, and the second zone to be contacted by recycle stream is preferably the adsorbent for removing the oxygenates, preferably the hybrid adsorbent. Conceivably, the flow of the recycle stream could go in the opposite direction, that is, from port (103) to port (114), in which case it is preferable if adsorbent (108) is the adsorbent primarily for quenching agent, and the adsorbent (106) is the adsorbent primarily for oxygenates.

The "residence time" of the recycle stream containing the oxygenates and water will depend on the dimensions of the bed, as contained in the vessel or drier column, as well as the particle sizes of the adsorbents, and the flow rate through the bed. The bulk density of the adsorbent is one factor, which in some embodiments may be from greater than or equal to about 0.05 g/ml to less than less or equal to about 1.2 g/ml and optionally within the range from about 0.08 g/ml or about 0.9 g/mol or about 0.1 g/mol or about 0.2 g/mol about 0.30 g/ml or about 0.40 g/ml or about 0.50 g/ml or about 0.60 g/ml or about 0.70 g/ml to about 1.0 g/ml or about 1.1 g/ml, where desirable ranges may include ranges from any lower limit to any upper limit. The bulk density may be different for each adsorbent also, for instance, the bulk density of the zeolitic molecular sieve may be within a range from greater than or equal to about 0.70 g/ml to less than or equal to about 1.0 g/ml. A bulk density of optional additional hybrid zeolite in alumina may be from greater than or equal to 0.8 g/ml to less than or equal to about 1.2 g/ml. The bulk density of the organosilica may be from greater than or equal to about 0.05 g/ml to less than less or equal to about 1.0 g/ml, optionally within the range from about 0.08 g/ml or about 0.9 g/mol or 0.1 g/ml or about 0.2 g/ml or about 0.3 g/ml or about 0.4 g/ml or about 0.5 g/ml or about 0.6 g/ml to about 0.7 g/ml to about 0.8 g/ml or about 0.9 g/ml or about 1.0 g/ml. In any case, the recycle stream preferably has a residence time, or time it takes the bulk solution (diluent) to flow through the at least two adsorbents, within the range of from 5 or 8 minutes to 12 or 15 or 20 minutes, where desirable ranges may include ranges from any lower limit to any upper limit; or, alternatively, the residence time for the recycle stream with each of the adsorbents, individually, is within the range of from 4 or 6 minutes to 10 or 14 or 18 minutes, where desirable ranges may include ranges from any lower limit to any upper limit, when the adsorbents are separated from one another. Based on the flow rate of the diluent in the recycle stream, which typically comprises from 80 to 90 or 95 or 98 wt % diluent, the residence time will be within the range from 0.1 or 1 or 5 or 10 kg diluent/hour to 30 or 40 or 50 kg/hour through the bed, where desirable ranges may include ranges from any lower limit to any upper limit.

Referring again to FIG. 6, the adsorbent bed (100) is preferably housed in a non-reactive vessel (102), preferably stainless steel, within the polymerization system in which it is associated with and has an port valve (114) for the recycle stream flowing through conduit (105) and port (103) for the stream exiting that has had the oxygenates and quenching agent partially or completely removed. The vessel may also have ports and ports for diluent used to regenerate the adsorbent, and the vessel may be heated, such that it heats the adsorbent contained therein. Thus, preferably, the adsorbent bed is regenerated by heating the adsorbent bed to a temperature in the range of from greater than or equal to about 150° C. or about 180° C. to less than or equal to about 250° C. or about 290° C. or about 400° C., where desirable ranges may include ranges from any lower limit to any upper limit. The organosilica material is stable up to about 400° C. in oxygen and about 600° C. in a nitrogen atmosphere. However, where the adsorbent bed includes multiple distinct adsorbents in addition to the organosilica material, the upper temperature limits during regeneration may be restricted to the upper temperatures that such additional adsorbent materials remain stable an upper temperature limit. This may be accomplished by subjecting the adsorbent bed to a hot diluent wash, or such a wash may take place in addition to heating the bed. Further the regeneration process may comprise, additionally or in lieu of other processes, sparging the adsorbent bed with hot nitrogen.

As mentioned, it has been found that detrimental catalyst poisons are particularly formed when non-conjugated diene monomers come into contact with quenching agents and the aluminum alkyl adducts often found in polymerization product streams. The aluminum alkyls may be present as scavengers in the polymerization reactor and/or as activators, as are alumoxanes, which are well known in the art.

Methods of combining olefins and other monomers with polymerization catalysts are well known in the art, and the present invention is not limited to any particular type of polymerization process. Conjugated or non-conjugated diene monomers, however, may be present in the inventive process, either alone or with other monomers, most preferably non-conjugated dienes. Typically, non-conjugated diene monomers are selected from the group consisting of $C_6$ to $C_{12}$ non-conjugated diene monomers, which are selected from the group consisting of: 2-methyl-1,4-pentadiene, 3-methyl-1,4-pentadiene, 1,4-hexadiene, 1,5-hexadiene, 2-methyl-1,5-hexadiene 3-methyl-1,4-hexadiene, 4-methyl-1,4-hexadiene, 5-methyl-1,4-hexadiene, 1,5-heptadiene, 1,6-heptadiene, norbornadiene, 3,3-dimethyl-1,3-hexadiene, 4-ethyl-1,4-hexadiene, 5-methyl-1,4-heptadiene, 6-methyl-1,4-heptadiene, 1-vinylcyclohexene, 5-methylene-2-norbornene, 1,6-octadiene, 1,7-octadiene, 1,9-octadiene, 1,7-nondiene, 1,8-nonadiene, 5-vinyl-2-norbornene, 5-ethylidene-2-norbornene, 5-ethyl-1,4-heptadiene, 5-ethyl-1,5-heptadiene, 4-methyl-1,4-octadiene, 5-methyl-1,4-octadiene, 5-methyl-1,5-octadiene, 6-methyl-1,5-octadiene, 6-methyl-1,6-octadiene, 7-methyl-1,6-octadiene, 1,8-decadiene, 1,9-decadiene, 1,4-divinylcyclohexane, 1,3-divinylcyclohexane, dicyclopentadiene, 3,7-dimethyl-1,6-octadiene, 5,7-dimethyl-1,6-octadiene, 4-ethyl-1,4-octadiene, 5-ethyl-1,4-octadiene, 5-ethyl-1,5-octadiene, 6-ethyl-1,5-octadiene, 6-ethyl-1,6-octadiene, 4-methyl-1,4-nonadiene, 5-methyl-1,4-nonadiene, 5-methyl-1,5-nonadiene, 6-methyl-1,5-nonadiene, 6-methyl-1,6-nonadiene, 7-methyl-1,6-nonadiene, 7-methyl-1,7-nonadiene, 5-allyl-2-norbornene, 1,10-undecadiene, 6-propyl-1,6-octadiene, 4-ethyl-1,4-nonadiene, 5-ethyl-1,4-nonadiene, 5-ethyl-1,5-nonadiene, 6-ethyl-1,5-nonadiene, 6-ethyl-1,6-nonadiene, 7-ethyl-1,6-nonadiene, 5-methyl-1,4-decadiene, 5-methyl-1,5-decadiene, 6-methyl-1,5-decadiene, 6-methyl-1,6-decadiene, 7-methyl-1,6-decadiene, 7-methyl-1,7-decadiene, 8-methyl-1,7-decadiene, 8-methyl-1,8-decadiene, 9-methyl-1,8-decadiene, 1,11-dodecadiene, 6-butyl-1,6-octadiene, 5-ethyl-1,4-decadiene, 5-ethyl-1,5-decadiene, 6-ethyl-1,5-decadiene, 6-ethyl-1,6-decadiene, 7-ethyl-1,6-decadiene, 7-ethyl-1,7-decadiene, 8-ethyl-1,7-decadiene, 8-ethyl-1,8-decadiene, 6-methyl-1,6-undecadiene, 8-methyl-1,6-undecadiene, and combinations thereof.

More preferably, the $C_6$ to $C_{12}$ non-conjugated diene monomers are selected from the group consisting of: 2-methyl-1,4-pentadiene, 3-methyl-1,4-pentadiene, 1,4-hexadiene, 1,5-hexadiene, 2-methyl-1,5-hexadiene, 1,6-heptadiene, norbornadiene, 1,7-octadiene, 1-vinylcyclohexene, 1,8-nonadiene, 5-vinyl-2-norbornene, 5-ethylidene-2-norbornene, 1,9-decadiene, 3,7-dimethyl-1,6-octadiene, 5,7-dimethyl-1,6-octadiene, 1,10-undecadiene, 1,11-dodecadiene, 5-methylene-2-norbornene, 5-allyl-2-norbornene, 5-vinyl-2-norbornene, 5-ethylidene-2-norbornene, dicyclopentadiene, and combinations thereof. Most preferably, the non-conjugated diene is 5-ethylidene-2-norbornene. In any case, one or more of ethylene or $C_3$ to $C_{12}$ alpha-olefin monomers may also be contacted with the polymerization catalyst and non-conjugated diene monomer.

Catalysts useful herein are described in WO 93/19103 and U.S. Pat. Nos. 5,096,867 and 5,264,405; 4,530,914; 4,542,199; 4,769,910; 4,808,561; 4,871,705; 4,933,403; 4,937,299; 5,017,714; 5,026,798; 5,057,475; 5,120,867; 5,278,119; 5,304,614; 5,324,800; 5,350,723; 5,391,790; and 7,141,632, each fully incorporated herein by reference.

As mentioned, the inventive adsorbent bed preferably comprises at least two adsorbents to remove quenching agent and/or $C_1$ to $C_{40}$ oxygenates. Preferably, at least one adsorbent is provided to remove at least the quenching agent, such as water, and at least one other adsorbent is provided to remove C1 to C40 oxygenates, or $C_8$ to $C_{40}$ oxygenates, or $C_{12}$ to $C_{30}$ oxygenates. The adsorbent for removing the quenching agent, such as water, may also remove $C_1$ to $C_8$ or $C_9$ oxygenates, understanding that there may be an overlap in what the various adsorbents will retain.

Referring to FIG. 6, one adsorbent can be the adsorbent (106), and the other could be adsorbent (108), where the recycle stream contacts each in turn. Alternatively, the adsorbents (106) and (108) can be mixed together where the recycle stream contacts both simultaneously. However, given that one adsorbent may require changing out sooner than the other, it is often advantageous to have them in separate zones as illustrated in FIG. 6. The most desirable adsorbents are those that adsorb the least amount of unreacted monomer materials from the reactor and adsorb the greatest amount of oxygenates and quenching agent, such as water. Most preferably, the adsorbents should remove water, $C_9$ oxygenates, and $C_{18}$ oxygenates that tend to form in the presence of 5-ethylidene-2-norbornene.

Preferably, at least one adsorbent in the adsorbent bed is an organosilica material, while another adsorbent may be a zeolitic molecular sieve. Alternatively, the adsorbent bed includes an organosilica material combined with a hybrid zeolite in alumina, along with a zeolitic molecular sieve. While it is understood that many solid adsorbents will be a mixture/combination of the actual adsorbent, binder, and other materials, the "hybrid zeolite in alumina" adsorbent referred to herein is of a particular quality and description as described herein. The zeolitic molecular sieve is desirable for removing water and lower oxygenates (e.g., $C_1$ to $C_6$ oxygenates), while the organosilica material or the organosilica material combined with hybrid zeolite in alumina is desirable for removing higher oxygenates, such as $C_8$ to $C_{40}$ oxygenates, or $C_{12}$ to $C_{30}$ oxygenates, most preferably $C_{18}$ oxygenates.

The zeolitic molecular sieve may comprise material selected from the group consisting of zeolite X, zeolite Y, zeolite A, faujasite, mordenite, ferrierite, and mixtures thereof. Zeolitic molecular sieves for removing water are well known in the art and are available from, for example, BASF and other manufacturers. The zeolitic molecular sieves preferably have a pore size within the range of from greater than or equal to about 2 Å or about 4 Å to less than or equal to about 6 Å or about 8 Å or about 10 Å or about 12 Å, where desirable ranges may include ranges from any lower limit to any upper limit.

The "hybrid zeolite in alumina" is a zeolite that is in a matrix of alumina. The hybrid zeolite in alumina may have a surface area within the range of from greater than or equal to about 60 $m^2/g$ or about 80 $m^2/g$ to less than or equal to about 110 $m^2/g$ or about 120 $m^2/g$ or about 140 $m^2/g$, where desirable ranges may include ranges from any lower limit to any upper limit. The hybrid zeolite in alumina may have a pore volume within the range of from greater than or equal to about 0.30 ml/g or about 0.35 ml/g or about 0.40 ml/g to less than or equal to about 0.48 ml/g or about 0.50 ml/g or about 0.54 ml/g, where desirable ranges may include ranges from any lower limit to any upper limit. A commercial example of a useful hybrid zeolite in alumina is zeolite UOP AZ-300™ from UOP.

In some embodiments, at least one of the adsorbents is binderless. For example, the zeolitic molecular sieve may be binderless and/or the hybrid zeolite in alumina may be binderless. A binderless zeolite is a zeolite that contains less than about 10 wt % binder, or less than about 7 wt % binder, or less than about 5 wt % binder, or less than about 2 wt % binder, where the binder content of the zeolite is measured by X-ray diffraction. In some embodiments, the zeolite is substantially free of binder and contains less than about 2 wt % binder. Using a binderless zeolite can allow for the creation of less oxygenates in the recycle stream, as the unreacted conjugated or non-conjugated diene monomer in the recycle stream and quenching agents, can react with the binder in a zeolitic material to form oxygenates. Additionally, in addition to the benefit that substantially no oxygenates are generated by the (binder) in the zeolite body, using a binderless zeolite can provide increased capacity per weight of the material for removing water/quenching agent. An example of a binderless zeolite that may be used is Zeochem Purmol® 3ST and Zeochem Purmol® 3STH.

As noted above, the inventive adsorbent bed desirably may contain more than two adsorbents. In some embodiments the adsorbent bed may contain an alumina adsorbent in addition to the adsorbents described above. The alumina adsorbent may be selected from calcined alumina, low soda alumina, reactive alumina, tabular alumina, fused alumina, high purity alumina, transition metal substituted alumina, silica/alumina, and mixtures thereof. Alumina may be used along with molecular sieves, especially to adsorb water and/or $C_1$ to $C_6$ oxygenates, or could be used instead of molecular sieves. A commercial example of a useful alumina adsorbent is Selexsorb™ (BASF).

Another type of adsorbent material that may be present in the bed instead of the hybrid adsorbent, or in addition to such adsorbent, is a silica, a commercial example of which is Perlkat™ (BASF). The silica adsorbent may be selected from fused quartz, crystal silica, fumed silica, colloidal silica, silica gel, aerogel, transition metal substituted silica, high purity silica, and mixtures thereof.

At least one of the adsorbents, preferably the silica, alumina, silica-alumina, or zeolitic adsorbents is a solid and has a surface area within the range of from greater than or equal to about 50 $m^2/g$ or about 80 $m^2/g$ or about 120 $m^2/g$ or about 150 $m^2/g$ or about 200 $m^2/g$ or about 250 $m^2/g$ or about 300 $m^2/g$ or about 350 $m^2/g$ to less than or equal to about 400 $m^2/g$ or about 500 $m^2/g$ or about 600 $m^2/g$ or about 800 $m^2/g$ or about 1000 $m^2/g$, where desirable ranges may include ranges from any lower limit to any upper limit. For example, a zeolitic adsorbent that contains binder (e.g., from 2-10 wt % zeolite with the remainder being binder, based on the weight of the zeolitic adsorbent) and has a surface area of from about 250 to about 600 $m^2/g$, or from about 300 to about 500 $m^2/g$, or from about 350 to about 450 $m^2/g$, may be used. For example, a binderless zeolitic adsorbent (e.g., less than 10 wt % binder, or less than 5 wt % binder, or less than 2 wt % binder, based on the weight of the zeolitic adsorbent) and has a surface area of from about 80 to about 400 $m^2/g$, or from about 100 to about 350 $m^2/g$, or from about 120 to about 300 $m^2/g$, may be used.

At least one of the adsorbents may be a solid and have an average pore volume within the range of from greater than or equal to about 0.2 ml/g or about 0.4 ml/g or about 0.6 ml/g to less than or equal to about 0.88 ml/g or about 1.0 ml/g or about 1.4 or about 1.6 ml/g or about 2.0 ml/g, where desirable ranges may include ranges from any lower limit to any upper limit. Desirable alumina or silica molecular sieves such as these may have a pore size within the range of from about 12 Å or about 20 Å or about 30 Å to about 40 Å or about 50 Å or about 60 Å or about 80 Å, where desirable ranges may include ranges from any lower limit to any upper limit.

III. ORGANOSILICA MATERIALS

In certain aspects, the invention relates to organosilica materials used as adsorbents. The organosilica materials may be a polymer formed of at least one monomer, as will be described further below. In certain variations, the organosilica material may be a polymer formed of multiple distinct monomers.

A. Monomers of Formula (I)

In a first embodiment, the organosilica material may be a polymer of at least one monomer of Formula $[Z^1OZ^2SiCH_2]_3$ (I), where $Z^1$ represents a hydrogen atom, a $C_1$-$C_4$ alkyl group, or a bond to a silicon atom of another monomer and $Z^2$ represents a hydroxyl group, a $C_1$-$C_4$ alkoxy group, a $C_1$-$C_6$ alkyl group, or an oxygen atom bonded to a silicon atom of another monomer.

As used herein, and unless otherwise specified, "a bond to a silicon atom of another monomer" means the bond can advantageously displace a moiety (particularly an oxygen-containing moiety such as a hydroxyl, an alkoxy or the like), if present, on a silicon atom of another monomer so there may be a bond directly to the silicon atom of the another monomer thereby connecting the two monomers, e.g., via a Si—O—Si linkage. As used herein, and unless otherwise specified, "an oxygen atom bonded to a silicon atom of another monomer" means that the oxygen atom can advantageously displace a moiety (particularly an oxygen-containing moiety such as a hydroxyl), if present, on a silicon atom of the another monomer so the oxygen atom may be bonded directly to the silicon atom of the another monomer thereby connecting the two monomers, e.g., via a Si—O—Si linkage. For clarity, in the aforementioned bonding scenarios, the "another monomer" can be a monomer of the same type or a monomer of a different type.

In various embodiments, each $Z^1$ can be a $C_1$-$C_4$ alkyl group, a $C_1$-$C_3$ alkyl group, a $C_1$-$C_2$ alkyl group, or methyl.

Each $Z^2$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group, a $C_1$-$C_4$ alkoxy group, a $C_1$-$C_3$ alkoxy group, a $C_1$-$C_2$ alkoxy group, methyl or methoxy, preferably each $Z^2$ can be a hydroxyl group, a $C_1$-$C_2$ alkyl group (methyl or ethyl), a $C_1$-$C_2$ alkoxy group (methoxy or ethoxy), or an oxygen atom bonded to a silicon atom of another monomer.

Each $Z^1$ can be a hydrogen atom, a $C_1$-$C_2$ alkyl group, or a bond to a silicon atom of another monomer and $Z^2$ can be a hydroxyl group, a $C_1$-$C_2$ alkyl group, a $C_1$-$C_2$ alkoxy group, or an oxygen atom bonded to a silicon atom of another monomer; or each $Z^1$ can be a hydrogen atom or a bond to a silicon atom of another monomer and each $Z^2$ can be a hydroxyl group, a $C_1$-$C_2$ alkyl group, or an oxygen atom bonded to a silicon atom of another monomer; or each $Z^1$ can be a hydrogen atom or a bond to a silicon atom of another monomer and each $Z^2$ can be a hydroxyl group, or an oxygen atom bonded to a silicon atom of another monomer; or each $Z^1$ can be a hydrogen atom, ethyl or a bond to a silicon atom of another monomer and each $Z^2$ can be a hydroxyl group, ethoxy, or an oxygen atom bonded to a silicon atom of another monomer; or each $Z^1$ can be a hydrogen atom, ethyl or a bond to a silicon atom of another monomer and each $Z^2$ can be methyl.

The organosilica material may be a polymer of at least one monomer of Formula (I) and also further comprises at least one additional monomer of Formula (I). For example, the polymer may comprise a first monomer of Formula (I), as well as a second distinct monomer of Formula (I).

The polymer may comprise a first monomer of Formula (I), wherein each $Z^1$ can be a hydrogen atom, ethyl or a bond to a silicon atom of another monomer and each $Z^2$ can be a hydroxyl group, ethoxy, or an oxygen atom bonded to a silicon atom of another monomer; and second distinct monomer of Formula (I), wherein each $Z^1$ can be a hydrogen atom, ethyl or a bond to a silicon atom of another monomer and each $Z^2$ can be methyl.

B. Monomers of Formula (II)

The organosilica material may be a polymer formed of multiple distinct monomers, including a monomer of Formula I in combination with one or more additional monomers.

In a second embodiment, the organosilica material may be a polymer of at least one monomer of Formula (I) and a monomer of Formula $Z^3OZ^4Z^5Z^6Si$ (II), where $Z^3$ independently represents a hydrogen atom or a $C_1$-$C_4$ alkyl group (preferably methyl, ethyl, propyl, or butyl), a $C_1$-$C_4$ alkoxy group (preferably methoxy, ethoxy, proposy or butoxy), a nitrogen-containing $C_1$-$C_{10}$ alkyl group, a nitrogen-containing heteroaralkyl group, and a nitrogen-containing optionally substituted heterocycloalkyl group, and an oxygen atom bonded to a silicon atom of another monomer.

Each $Z^3$ can be a $C_1$-$C_3$ alkyl group, a $C_1$-$C_2$ alkyl group (preferably ethyl, methyl, propyl, butyl) or a bond to a silicon atom of another monomer, and/or each $Z^4$, $Z^5$ and $Z^6$ each independently can be a hydroxyl group. Alternately each $Z^3$ can be a hydrogen atom, a $C_1$-$C_2$ alkyl group, or a bond to a silicon atom of another monomer and $Z^4$, $Z^5$ and $Z^6$ each independently can be a hydroxyl group or a $C_1$-$C_2$ alkyl group.

Preferably, each $Z^4$, $Z^5$ and $Z^6$ independently can be a $C_1$-$C_4$ alkyl group, a $C_1$-$C_3$ alkyl group, a $C_1$-$C_2$ alkyl group, or methyl, preferably a hydroxyl group, or a $C_1$-$C_2$ alkyl group, alternately each $Z^4$, $Z^5$ and $Z^6$ independently can be a $C_1$-$C_4$ alkoxy group, a $C_1$-$C_3$ alkoxy group, a $C_1$-$C_2$ alkoxy group, or methoxy, preferably each $Z^4$, $Z^5$ and $Z^6$ is independently can be selected from the group consisting of a hydroxyl group, a $C_1$-$C_2$ alkyl group and a $C_1$-$C_2$ alkoxy group.

Alternately, each $Z^3$ can be a hydrogen atom, a $C_1$-$C_2$ alkyl group, or a bond to a silicon atom of another monomer; and $Z^4$, $Z^5$ and $Z^6$ each independently can be selected from the group consisting of a hydroxyl group, a $C_1$-$C_2$ alkyl group and a $C_1$-$C_2$ alkoxy group.

Each $Z^4$, $Z^5$ and $Z^6$ each independently can be a nitrogen-containing $C_1$-$C_{10}$ alkyl group, a nitrogen-containing $C_1$-$C_9$ alkyl group, a nitrogen-containing $C_1$-$C_8$ alkyl group, a nitrogen-containing $C_1$-$C_7$ alkyl group, a nitrogen-containing $C_1$-$C_6$ alkyl group, a nitrogen-containing $C_1$-$C_5$ alkyl group, a nitrogen-containing $C_1$-$C_4$ alkyl group, a nitrogen-containing $C_1$-$C_3$ alkyl group, a nitrogen-containing $C_1$-$C_2$ alkyl group, or a methylamine. In particular, $Z^4$, $Z^5$ and $Z^6$ each independently can be a nitrogen-containing $C_2$-$C_{10}$ alkyl group, a nitrogen-containing $C_3$-$C_{10}$ alkyl group, a nitrogen-containing $C_3$-$C_9$ alkyl group, or a nitrogen-containing $C_3$-$C_8$ alkyl group. The aforementioned nitrogen-containing alkyl groups may have one or more nitrogen atoms (e.g., 2, 3, etc.). Examples of nitrogen-containing $C_1$-$C_{10}$ alkyl groups include, but are not limited to,

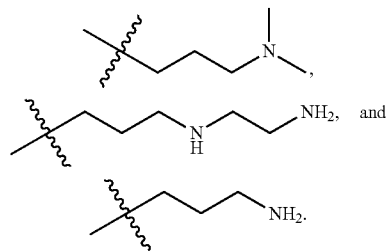

Each $Z^4$, $Z^5$ and $Z^6$ each independently can be selected from the group consisting of a hydroxyl group, a $C_1$-$C_2$ alkyl group, a $C_1$-$C_2$ alkoxy group and a nitrogen-containing $C_3$-$C_{10}$ alkyl group, a nitrogen-containing heteroaralkyl group. The nitrogen-containing heteroaralkyl group can be a nitrogen-containing $C_4$-$C_{12}$ heteroaralkyl group, a nitrogen-containing $C_4$-$C_{10}$ heteroaralkyl group, or a nitrogen-containing $C_4$-$C_8$ heteroaralkyl group. Examples of nitrogen-containing heteroaralkyl groups include but are not limited to pyridinylethyl, pyridinylpropyl, pyridinylmethyl, indolylmethyl, pyrazinylethyl, and pyrazinylpropyl. The aforementioned nitrogen-containing heteroaralkyl groups may have one or more nitrogen atoms (e.g., 2, 3, etc.), preferably $Z^4$, $Z^5$ and $Z^6$ each independently can be selected from the group consisting of a hydroxyl group, a $C_1$-$C_2$ alkyl group, a $C_1$-$C_2$ alkoxy group, nitrogen-containing $C_3$-$C_{10}$ alkyl group and a nitrogen-containing heteroaralkyl group.

Alternately, $Z^4$, $Z^5$ and $Z^6$ each independently can be a nitrogen-containing heterocycloalkyl group, wherein the heterocycloalkyl group may be optionally substituted with a $C_1$-$C_6$ alkyl group, particularly a $C_1$-$C_4$ alkyl group. The nitrogen-containing heterocycloalkyl group can be a nitrogen-containing $C_4$-$C_{12}$ heterocycloalkyl group, a nitrogen-containing $C_4$-$C_{10}$ heterocycloalkyl group, or a nitrogen-containing $C_4$-$C_8$ heterocycloalkyl group. Examples of nitrogen-containing heterocycloalkyl groups include but are not limited to piperazinylethyl, piperazinylpropyl, piperidinylethyl, piperidinylpropyl. The aforementioned nitrogen-containing heterocycloalkyl groups may have one or more nitrogen atoms (e.g., 2, 3, etc.).

In a particular embodiment, each $Z^3$ can be a hydrogen atom, ethyl or a bond to a silicon atom of another monomer; and $Z^4$, $Z^5$ and $Z^6$ each independently can be selected from the group consisting of a hydroxyl group, ethoxy, and an oxygen atom bonded to a silicon atom of another monomer.

In another particular embodiment, each $Z^3$ can be a hydrogen atom, ethyl or a bond to a silicon atom of another comonomer; $Z^4$ and $Z^5$ each independently can be selected from the group consisting of a hydroxyl group, ethoxy, and an oxygen atom bonded to a silicon atom of another monomer; and $Z^6$ can be methyl.

In another particular embodiment, each $Z^3$ can be a hydrogen atom, methyl or a bond to a silicon atom of another comonomer; $Z^4$ and $Z^5$ each independently can be selected from the group consisting of a hydroxyl group, methoxy, and an oxygen atom bonded to a silicon atom of another monomer; and $Z^6$ can be

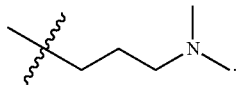 [SMILES: *CCCN(C)C]

In another particular embodiment, each $Z^3$ can be a hydrogen atom, ethyl or a bond to a silicon atom of another comonomer; $Z^4$ and $Z^5$ each independently can be selected from the group consisting of a hydroxyl group, ethoxy, and an oxygen atom bonded to a silicon atom of another monomer; and $Z^6$ can be

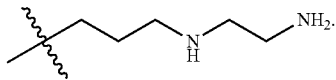 [SMILES: *CCCNCCN]

In another particular embodiment, each $Z^3$ can be a hydrogen atom, ethyl or a bond to a silicon atom of another comonomer; $Z^4$ and $Z^5$ each independently can be selected from the group consisting of a hydroxyl group, ethoxy, and an oxygen atom bonded to a silicon atom of another monomer; and $Z^6$ can be

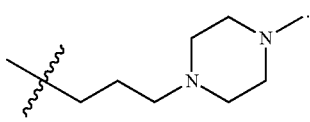 [SMILES: *CCCN1CCN(C)CC1]

In another particular embodiment, each $Z^3$ can be a hydrogen atom, ethyl or a bond to a silicon atom of another comonomer; $Z^4$ and $Z^5$ each independently can be selected from the group consisting of a hydroxyl group, ethoxy, and an oxygen atom bonded to a silicon atom of another monomer; and $Z^6$ can be

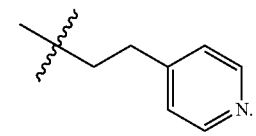 [SMILES: *CCc1ccncc1]

In another particular embodiment, each $Z^3$ can be a hydrogen atom, ethyl or a bond to a silicon atom of another comonomer; $Z^4$ and $Z^5$ each independently can be selected from the group consisting of a hydroxyl group, ethoxy, and an oxygen atom bonded to a silicon atom of another monomer; and $Z^6$ can be

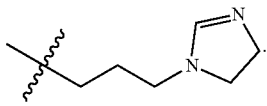

In another particular embodiment, each $Z^3$ can be a hydrogen atom, ethyl or a bond to a silicon atom of another comonomer; $Z^4$ and $Z^5$ each independently can be selected from the group consisting of a hydroxyl group, ethoxy, and an oxygen atom bonded to a silicon atom of another monomer; and $Z^6$ can be

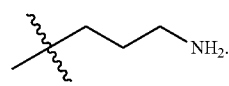

C. Monomers of Formula (III)

In a third embodiment, the organosilica material may be a polymer of at least one monomer of Formula (I) and a monomer having at least one unit of Formula:

$Z^7Z^8Z^9Si$—R—$SiZ^7Z^8Z^9$ (III), where each $Z^7$ independently represents a hydroxyl group, a $C_1$-$C_4$ alkoxy group, or an oxygen atom bonded to a silicon atom of another comonomer; each of $Z^8$ and $Z^9$ independently represent a hydroxyl group, a $C_1$-$C_4$ alkoxy group, a $C_1$-$C_4$ alkyl group, or an oxygen bonded to a silicon atom of another monomer; and R is selected from the group consisting of a $C_1$-$C_8$ alkylene group, a $C_2$-$C_8$ alkenylene group, a $C_2$-$C_8$ alkynylene group, a nitrogen-containing $C_2$-$C_{10}$ alkylene group, an optionally substituted $C_6$-$C_{20}$ aralkyl and an optionally substituted $C_4$-$C_{20}$ heterocycloalkyl group.

Each $Z^7$ can be a hydroxyl group or a $C_1$-$C_4$ alkoxy group, a $C_1$-$C_3$ alkoxy group, a $C_1$-$C_2$ alkoxy group, or methoxy, preferably a hydroxyl group, or a $C_1$-$C_2$ alkoxy group or oxygen atom bonded to a silicon atom of another comonomer.

Each $Z^8$ and $Z^9$ can independently be a hydroxyl group a $C_1$-$C_4$ alkoxy group, a $C_1$-$C_3$ alkoxy group, a $C_1$-$C_2$ alkoxy group, or methoxy, a $C_1$-$C_4$ alkyl group, a $C_1$-$C_3$ alkyl group, a $C_1$-$C_2$ alkyl group, or methyl. Alternately, each $Z^8$ and $Z^9$ independently can be an oxygen atom bonded to a silicon atom of another comonomer.

Each $Z^7$ can be a hydroxyl group, a $C_1$-$C_2$ alkoxy group, or an oxygen atom bonded to a silicon atom of another comonomer; and $Z^8$ and $Z^9$ each independently can be a hydroxyl group, a $C_1$-$C_2$ alkoxy group, a $C_1$-$C_2$ alkyl group, or an oxygen atom bonded to a silicon atom of another comonomer.

Alternately, when present with Formula (I), each $Z^7$ can be a hydroxyl group, ethoxy, methoxy or an oxygen atom bonded to a silicon atom of another comonomer; and each $Z^8$ and $Z^9$ independently can be a hydroxyl group, ethoxy, methyl, or an oxygen atom bonded to a silicon atom of another comonomer.

Alternately, $R^1$ can be a $C_1$-$C_8$ alkylene group, a $C_1$-$C_7$ alkylene group, a $C_1$-$C_6$ alkylene group, a $C_1$-$C_5$ alkylene group, a $C_1$-$C_4$ alkylene group, a $C_1$-$C_3$ alkylene group, a $C_1$-$C_2$ alkylene group, or —CH$_2$—.

Alternately, $R^1$ can be a nitrogen-containing $C_2$-$C_{10}$ alkylene group, a nitrogen-containing $C_3$-$C_{10}$ alkylene group, a nitrogen-containing $C_4$-$C_{10}$ alkylene group, a nitrogen-containing $C_4$-$C_9$ alkylene group, a nitrogen-containing $C_4$-$C_8$ alkylene group, or nitrogen containing $C_3$-$C_8$ alkylene group. The aforementioned nitrogen-containing alkylene groups may have one or more nitrogen atoms (e.g., 2, 3, etc.). Examples of nitrogen-containing alkylene groups include, but are not limited to,

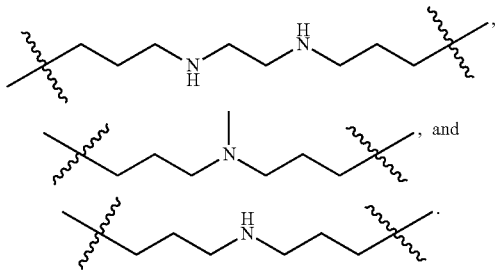

Each $Z^7$ can be a hydroxyl group, a $C_1$-$C_2$ alkoxy group, or an oxygen atom bonded to a silicon atom of another comonomer; each $Z^8$ and $Z^9$ independently can be a hydroxyl group, a $C_1$-$C_2$ alkoxy group, a $C_1$-$C_2$ alkyl group, or an oxygen atom bonded to a silicon atom of another comonomer; and $R^1$ can be selected from the group consisting of a $C_1$-$C_4$ alkylene group, a $C_2$-$C_4$ alkenylene group, a $C_2$-$C_4$ alkynylene group and a nitrogen-containing $C_4$-$C_{10}$ alkylene group.

Alternately, $R^1$ can be an optionally substituted $C_6$-$C_{20}$ aralkyl, an optionally substituted $C_6$-$C_{14}$ aralkyl, or an optionally substituted $C_6$-$C_{10}$ aralkyl. Examples of $C_6$-$C_{20}$ aralkyls include, but are not limited to, phenymethyl, phenylethyl, and naphthylmethyl. The aralkyl may be optionally substituted with a $C_1$-$C_6$ alkyl group, particularly a $C_1$-$C_4$ alkyl group.

Alternately, $R^1$ can be an optionally substituted $C_4$-$C_{20}$ heterocycloalkyl group, an optionally substituted $C_4$-$C_{16}$ heterocycloalkyl group, an optionally substituted $C_4$-$C_{12}$ heterocycloalkyl group, or an optionally substituted $C_4$-$C_{10}$ heterocycloalkyl group. Examples of $C_4$-$C_{20}$ heterocycloalkyl groups include, but are not limited to, thienylmethyl, furylethyl, pyrrolylmethyl, piperazinylethyl, pyridylmethyl, benzoxazolylethyl, quinolinylpropyl, and imidazolylpropyl. The heterocycloalkyl may be optionally substituted with a $C_1$-$C_6$ alkyl group, particularly a $C_1$-$C_4$ alkyl group.

Each $Z^7$ can be a hydroxyl group, ethoxy, methoxy or an oxygen atom bonded to a silicon atom of another comonomer; each $Z^8$ and $Z^9$ independently can be a hydroxyl group, ethoxy, methoxy, methyl, or an oxygen atom bonded to a silicon atom of another comonomer; and $R^1$ can be selected from the group consisting of —CH$_2$—, —CH$_2$CH$_2$—, —HC=CH—,

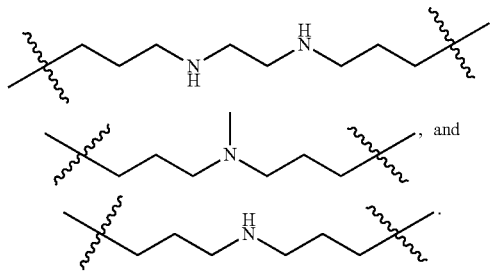

Each $Z^7$ can be a hydroxyl group, or an oxygen atom bonded to a silicon atom of another comonomer; each $Z^8$ and $Z^9$ independently can be a hydroxyl group, methyl, or an oxygen atom bonded to a silicon atom of another comonomer; and $R^1$ can be selected from the group consisting of —CH$_2$—, —CH$_2$CH$_2$—, —HC=CH—, In a particular embodiment, each $Z^7$ can be a hydroxyl group, ethoxy or an oxygen atom bonded to a silicon atom of another comonomer; each $Z^8$ can be a hydroxyl group, ethoxy, and an oxygen atom bonded to a silicon atom of another monomer; each $Z^9$ can be methyl; and $R^1$ can be —CH$_2$CH$_2$—. In another particular embodiment, each $Z^7$ can be a hydroxyl group, ethoxy or an oxygen atom bonded to a silicon atom of another comonomer; each $Z^8$ and $Z^9$ independently can be selected from the group consisting of a hydroxyl group, ethoxy, and an oxygen atom bonded to a silicon atom of another monomer; and $R^1$ can be —CH$_2$— or —HC=CH—. In another particular embodiment, each $Z^7$ can be a hydroxyl group, ethoxy or an oxygen atom bonded to a silicon atom of another comonomer; each $Z^8$ can be a hydroxyl group, ethoxy, and an oxygen atom bonded to a silicon atom of another monomer; each $Z^9$ can be methyl; and $R^1$ can be

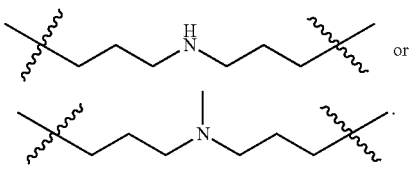

D. Monomers of Formula (IV)

In a fourth embodiment, the organosilica material support may be a polymer of at least one monomer of Formula (I) and a monomer having at least one trivalent metal oxide monomer of Formula $M^1(OZ^{10})_3$ (IV), where $M^1$ represents a Group 13 metal (preferably B, Al, Ga, In, or Tl, preferably B, Al or Ga, preferably Al) and $Z^{10}$ represents a hydrogen atom, a $C_1$-$C_6$ alkyl (preferably methyl, ethyl, propyl, butyl, pentyl or hexyl) or a bond to a silicon atom of another monomer.

Each $M^1$ can be B, Al, Ga, In Tl, or Uut. In particular, $M^1$ can be Al or B. Preferably $M^1$ can be Al or B and $Z^{10}$ can be a hydrogen atom, methyl, ethyl, propyl or butyl.

Each $Z^{10}$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group, or methyl. In particular, $Z^{10}$ can be methyl, ethyl, propyl or butyl.

Alternately, when present with Formula (I), each $Z^1$ and $Z^2$ each independently can be can be a hydrogen atom, a $C_1$-$C_2$ alkyl group (methyl or ethyl), or a bond to a silicon atom of another monomer; each $M^1$ can be Al or B; and each $Z^{10}$ can be a hydrogen atom, methyl, ethyl, propyl, butyl or a bond to a silicon atom of another monomer.

E. Monomers of Formula (V)

In a fifth embodiment, the organosilica material support may be a polymer of at least one monomer of Formula (I) and a monomer having at least one trivalent metal oxide monomer of Formula $(Z^{11}O)^2M^2$-O—$Si(OZ^{12})_3$ (V), wherein $M^2$ represents a Group 13 metal (preferably B, Al, Ga, In, or Tl, preferably B, Al or Ga, preferably Al) and $Z^{11}$ and $Z^{12}$ each independently represent a hydrogen atom, a $C_1$-$C_6$ alkyl group (such as methyl, ethyl, propyl, butyl, pentyl or hexyl) or a bond to a silicon atom of another monomer.

Each $M^2$ can be B, Al, Ga, In Tl, or Uut. In particular, each $M^2$ can be Al or B. Preferably each $M^2$ can be Al or B and each $Z^{11}$ and $Z^{12}$ are a hydrogen atom.

Each $Z^{11}$ and/or $Z^{12}$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group, or methyl. In particular, each $Z^{11}$ and/or $Z^{12}$ can be methyl, ethyl, propyl or butyl.

In a particular embodiment, each $M^2$ can be Al; and $Z^{11}$ and/or $Z^{12}$ each independently can be a hydrogen atom, methyl, ethyl, propyl, butyl, or a bond to a silicon atom of another monomer.

F. Monomers of Formula (VI)

In a sixth embodiment, the organosilica material may be a polymer of at least one cyclic polyurea monomer. The organosilica material may be a polymer formed of multiple distinct monomers, including a monomer of Formula I in combination with one or more cyclic polyurea monomers. A suitable cyclic polyurea monomer of Formula

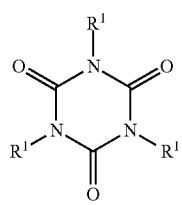

(VI)

where $R^1$ is a $Z^{13}OZ^{14}Z^{15}SiZ^{16}$ group, wherein each $Z^{13}$ represents a hydrogen atom, a $C_1$-$C_4$ alkyl group, or a bond to a silicon atom of another monomer unit; each $Z^{14}$ and $Z^{15}$ independently represents a hydroxyl group, a $C_1$-$C_4$ alkyl group, a $C_1$-$C_4$ alkoxy group or an oxygen atom bonded to a silicon atom of another monomer unit; and each $Z^{16}$ represents a $C_1$-$C_8$ alkylene group bonded to a nitrogen atom of the cyclic polyurea.

In certain other aspects, the organosilica material may be a polymer formed of monomers of Formula VI, with or without any other monomers, including those of Formula I.

In various embodiments, each $Z^{13}$ can be methyl, ethyl, propyl, or butyl, preferably methyl or ethyl. Each $Z^{14}$ and $Z^{15}$ independently can be a alkyl group, such as methyl, ethyl, propyl, or butyl, preferably methyl or ethyl. Each $Z^{14}$ and $Z^{15}$ independently can be a hydroxyl group, such as a $C_1$-$C_4$ alkoxy group, a $C_1$-$C_3$ alkoxy group, a $C_1$-$C_2$ alkoxy group or methoxy. Each $Z^{16}$ can be a $C_1$-$C_7$ alkylene group bonded to a nitrogen atom of the cyclic polyurea, a $C_1$-$C_7$ alkylene group bonded to a nitrogen atom of the cyclic polyurea, a $C_1$-$C_6$ alkylene group bonded to a nitrogen atom of the cyclic polyurea, a $C_1$-$C_4$ alkylene group bonded to a nitrogen atom of the cyclic polyurea, a $C_1$-$C_3$ alkylene group bonded to a nitrogen atom of the cyclic polyurea, a $C_1$-$C_2$ alkylene group bonded to a nitrogen atom of the cyclic polyurea, or —$CH_2$— bonded to a nitrogen atom of the cyclic polyurea. Each $Z^{13}$ can be a hydrogen atom, a $C_1$-$C_2$ alkyl group or a bond to a silicon atom of another monomer; each $Z^{14}$ and $Z^{15}$ independently can be a hydroxyl group, a $C_1$-$C_2$ alkyl group, a $C_1$-$C_2$ alkoxy group, or an oxygen atom bonded to a silicon atom of another monomer unit; and $Z^{16}$ can be a $C_1$-$C_4$ alkylene group bonded to a nitrogen atom of the cyclic polyurea. In a particular embodiment, each $Z^{13}$ can be a hydrogen atom, methyl, or a bond to a silicon atom of another monomer; each $Z^{14}$ and $Z^{15}$ independently can be a hydroxyl group, methoxy or an oxygen atom bonded to a silicon atom of another monomer unit; and each $Z^{16}$ can be —$CH_2CH_2CH_2$— bonded to a nitrogen atom of the cyclic polyurea.

G. Organosilica Material Characterization

In certain aspects, the invention relates to organosilica materials that may be a polymer formed from a reaction of any of the monomers of Formulas (I)-(VI), although in certain alternative variations, the organosilica materials are not limited to only these monomers. Furthermore, in certain embodiments, the organosilica material may be a polymer formed of multiple distinct monomers, including any combinations of monomers of Formula (I) with one or more monomers of Formulas (II)-(VI). As noted above, in certain alternative embodiments, the organosilica material may be a polymer formed of one or more monomers of Formula (VI), with or without other monomers of Formulas (I)-(V).

The inventive technology thus uses the monomer building blocks described above to form an organosilane having a high surface area and high porosity without use of any structure directing agent (SDA), porogen. However, in certain aspects, the pores in the organosilane materials of the invention are not arranged in an ordered structure as they would be if formed with a structure directing agent (SDA). Conventional periodic mesoporous organosilicas (PMO) materials have highly ordered pore structures that occur by use of SDAs (typically surfactants) during reaction formations. In contrast, in certain aspects, the organosilica materials of the present disclosure may be formed without use of any SDAs or porogens as a template, while still exhibiting relatively ordered pore structures and desirably high surface area and porosity levels.

In various aspects, the organosilica materials made by the methods described herein can be characterized as described in the following sections. Further description and characterization of suitable organosilica materials for use herein can be found in "CO-FILED CASES" which are defined to be: (1) U.S. Ser. No. 14/966,001 filed Dec. 11, 2015; 2) U.S. Ser. No. 14/965,992 filed Dec. 11, 2015; 3) U.S. Ser. No. 14/965,984 filed Dec. 11, 2015; 4) U.S. Ser. No. 14/966,383 filed Dec. 11, 2015; 5) U.S. Ser. No. 14/966,015 filed Dec. 11, 2015; and 6) U.S. Ser. No. 14/966,284 filed Dec. 11, 2015.

i. X-Ray Diffraction Peaks

The organosilica materials made by the methods described herein can exhibit powder X-ray diffraction patterns with one broad peak between about 1 and about 4 degrees 2θ, particularly one peak between about 1 and about 3 degrees 2θ, or particularly one peak between about 1 and about 2 degrees 2θ. Alternately, the organosilica materials can exhibit substantially no peaks in the range of about 0.5 to about 10 degrees 2θ (alternatively 12, 15 20, 2, 30 40, 50, 60 or 70 degrees 2θ), or in the range of about 2 to about 10 degrees 2θ (alternatively 12, 15 20, 2, 30 40, 50, 60 or 70 degrees 2θ), or in the range of about 3 to about 10 degrees 2θ (alternatively 12, 15 20, 2, 30 40, 50, 60 or 70 degrees 2θ).

ii. Silanol Content

The organosilica materials can have a silanol content that varies within wide limits, depending on the composition of the synthesis solution. The silanol content can conveniently be determined by solid state silicon NMR, more specifically by using solid state $^{29}$Si or $^1$H NMR. In various aspects, the organosilica material can have a silanol content of greater than about 5% (preferably greater than 10, 15, 20, 25, 30, 33, 35, 40, 41, 44, 45, 50, 55, 60, 5, 70, 75, 80 percent). In certain embodiments, the silanol content can be greater than about 30% or greater than about 41%. Alternately, the organosilica material may have a silanol content of about 5% to about 80%, or about 5% to about 50%, or about 5% to about 25%, or about 5% to about 10%, or about 10% to about 50%, or about 10% to about 20%, or about 20% to about 30%, or about 30% to about 50%.

iii. Pore Size

The organosilica materials described herein are advantageously in a mesoporous form. As indicated previously, the term mesoporous refers to solid materials having pores with a diameter within the range of from greater than or equal to about 2 nm to less than or equal to about 50 nm. The average pore diameter of the organosilica material can be determined, for example, using nitrogen adsorption-desorption isotherm techniques within the expertise of one of skill in the art, such as the BET (Brunauer Emmet Teller) method. Pore size can be measured by the Brunauer-Emmett-Teller (BET) method using adsorption-desorption of nitrogen (temperature of liquid nitrogen, 77 K) with a Micromeritics Tristar II 3020 instrument after degassing of the powders for 4 hrs. at 350° C. Typically, the samples are pre-treated with 120° C./vacuum/4 hours before the BET analysis is conducted. More information regarding the method can be found, for example, in S. Lowell et al., "Characterization of Porous Solids and Powders: Surface Area, Pore Size and Density," Springer (2004).

The organosilica material can have an average pore diameter of about 0.2 nm (alternately about 0.4 nm, about 0.5 nm, about 0.6 nm, about 0.8 nm, about 1.0 nm, about 1.5 nm, about 1.8 nm) to less than about 2.0 nm. Alternately, the organosilica material can have an average pore diameter of 0.2 nm to about 50 nm (preferably 0.2 to 40, 30, 25, 23, 20, 18, 15, 13, 11, 10, 9, 8.4, 8, 7.3, 7.0, 6.0, 5.0, 4.5, 4.1, 4.0, 3.5, 3.0, 2.5, 2.0, 1.5, or 1.0 nm) alternatively, about 1.0 nm to about 40 nm (preferably 1.0 nm to 35, 30, 25, 23, 20, 18, 15, 13, 11, 10, 9, 8.4, 8, 7.3, 7.0, 6.0, 5.0, 4.5, 4.1, 4.0, 3.5, 3.0, 2.5, 2.0, 1.5, or 1.0 nm). In particular, the organosilica material, preferably produced by the methods described herein or in the CO-FILED CASES, can advantageously have an average pore diameter in the mesopore range of 0.2 nm to about 50 nm, or about 1.0 nm to about 50 nm, or in the mesopore range of about 2.0 nm to about 50 nm, about 2.0 nm to about 40 nm, about 2.0 nm to about 30 nm, about 2.0 nm to about 20 nm, about 2.0 nm to about 10 nm, about 2.0 nm to about 5.0 nm, and about 2.0 nm to about 4.0 nm.

Using surfactant as a template to synthesize mesoporous materials can create highly ordered structure, e.g. well-defined cylindrical-like pore channels. In some circumstances, there may be no hysteresis loop observed from $N_2$ adsorption isotherm. In other circumstances, for instance where mesoporous materials can have less ordered pore structures, a hysteresis loop may be observed from $N_2$ adsorption isotherm experiments. In such circumstances, without being bound by theory, the hysteresis can result from the lack of regularity in the pore shapes/sizes and/or from bottleneck constrictions in such irregular pores.

iv. Surface Area

The surface area of the organosilica material can be determined, for example, using nitrogen adsorption-desorption isotherm techniques within the expertise of one of skill in the art, such as the BET (Brunauer Emmet Teller) method. This method may determine a total surface area, an external surface area, and a microporous surface area. As used herein, and unless otherwise specified, "total surface area" refers to the total surface area as determined by the BET method. As used herein, and unless otherwise specified, "microporous surface area" refers to microporous surface are as determined by the BET method. Surface area determined by the BET method uses adsorption-desorption of nitrogen (temperature of liquid nitrogen, 77 K) with a Micromeritics Tristar II 3020 instrument after degassing of the powders for 4 hrs. at 350° C. Typically, the samples are pre-treated with 120° C./vacuum/4 hours before the BET analysis is conducted. More information regarding the method can be found, for example, in S. Lowell et al., "Characterization of Porous Solids and Powders: Surface Area, Pore Size and Density," Springer (2004).

In various embodiments, the organosilica material can have a total (e.g., BET) surface area greater than or equal to 2 m$^2$/g to less than or equal to about 2,500 m$^2$/g, about 50 m$^2$/g to about 2,500 m$^2$/g, about 100 m$^2$/g to about 2,500 m$^2$/g, about 200 m$^2$/g to about 2,500 m$^2$/g, about 300 m$^2$/g to about 2,500 m$^2$/g, or about 400 m$^2$/g to about 2,500 m$^2$g.

The organosilica material obtainable by the methods described herein may be advantageously obtainable at variable aging times and temperatures as discussed above. At early aging times, the nitrogen adsorption isotherm exhibits complete reversibility, whereby the adsorption and desorption legs of the isotherm are on top of each other. At some intermediate aging time, a hysteresis appears as an offset in the adsorption and desorption legs. The size of this offset increases with increasing aging time to a point, after which it remains constant with increasing aging time.

v. Pore Volume

The pore volume of the organosilica material is determined by the Brunauer-Emmett-Teller (BET) method described above. In various embodiments, the organosilica material can have a pore volume of about 0.1 cm$^3$/g or more, about 0.5 cm$^3$/g or more, about 1.0 cm$^3$/g or more, about 2.0 cm$^3$/g or more, about 3.0 cm$^3$/g or more, about 4.0 cm$^3$/g or more, about 5.0 cm$^3$/g or more, or about 10.0 cm$^3$/g or more. Alternately, the organosilica material can have a pore volume of about 0.1 cm$^3$/g to about 10.0 cm$^3$/g, about 0.2 cm$^3$/g to about 7.0 cm$^3$/g, about 0.3 cm$^3$/g to about 5.0 cm$^3$/g, about 0.6 cm$^3$/g to about 1.0 cm$^3$/g, preferably from 0.1 cm$^3$/g to about 5.0 cm$^3$/g, particularly about 0.1 cm$^3$/g to about 3.0 cm$^3$/g, particularly about 0.2 cm$^3$/g to about 2.5 cm$^3$/g, or particularly about 0.2 cm$^3$/g to about 1.5 cm$^3$/g.

vi. Particle Size

Alternately, the organosilica material can have an average particle size in the range of from greater than or equal to about 5 μm to about 500 μm. Average particle size, also referred to as "particle size," or "particle diameter" is determined using a Mastersizer™ 3000 (range of 1 to 3500 μm) available from Malvern Instruments, Ltd. Worcestershire, England. Particle size distribution via laser sizing can also be a method of measuring ranges of average particles sizes and particle dispersion.

vii. Dried Particles

Alternately, the organosilica material support material may be dry, that is, free of absorbed water. Drying of the organosilica material can be effected by heating or calcining at a range of greater than or equal to about 100° C. to less than or equal to about 1000° C., preferably it is heated to at least 200° C., preferably from about 200° C. to about 850° C., and most preferably at about 600° C.; and for a time of about 1 minute to about 100 hours, from about 12 hours to about 72 hours, or from about 24 hours to about 60 hours. The calcined material preferably has at least some reactive oxygen containing groups, such as hydroxyl (OH) groups.

In another particular embodiment, an organosilica material as described herein i) has an X Ray Diffraction Spectrum exhibiting substantially no peaks above 4 degrees 2θ; and/or ii) is made using substantially no added structure directing agent or porogen.

IV. METHODS OF MAKING ORGANOSILICA MATERIALS

In another embodiment, methods of producing the organosilica material described herein are provided. The method comprises: (a) providing an aqueous mixture that contains essentially no structure directing agent and/or porogen; (b) adding at least one compound of Formula [R$^1$R$^2$SiCH$_2$]$_3$ (Ia) into the aqueous mixture to form a solution, wherein R$^1$ can be a C$_1$-C$_4$ alkoxy group and R$^2$ can be a C$_1$-C$_4$ alkoxy group or a C$_1$-C$_4$ alkyl group; (c) aging the solution to produce a pre-product (for example, a gel); and (d) drying the pre-product to obtain an organosilica material which is a polymer comprising at least one monomer of Formula (I) as described herein.

A. Aqueous Mixture

The organosilica materials described herein may be made using essentially no structure directing agent or porogen. Thus, the aqueous mixture contains essentially no added structure directing agent and/or no added porogen.

As used herein, "no added structure directing agent," and "no added porogen" means either (i) there is no component present in the synthesis of the organosilica material that aids in and/or guides the polymerization and/or polycondensing and/or organization of the building blocks that form the framework of the organosilica material; or (ii) such component is present in the synthesis of the organosilica material in a minor, or a non-substantial, or a negligible amount such that the component cannot be said to aid in and/or guide the polymerization and/or polycondensing and/or organization of the building blocks that form the framework of the organosilica material. Further, "no added structure directing agent" is synonymous with "no added template" and "no added templating agent."

i. Structure Directing Agent

Examples of a structure directing agent can include, but are not limited to, non-ionic surfactants, ionic surfactants, cationic surfactants, silicon surfactants, amphoteric surfactants, polyalkylene oxide surfactants, fluorosurfactants, colloidal crystals, polymers, hyper branched molecules, star-shaped molecules, macromolecules, dendrimers, and combinations thereof. Alternately, the surface directing agent can comprise or be a poloxamer, a triblock polymer, a tetraalkylammonium salt, a nonionic polyoxyethylene alkyl, a Gemini surfactant, or a mixture thereof. Examples of a tetraalkylammonium salt can include, but are not limited to, cetyltrimethylammonium halides, such as cetyltrimethylammonium chloride (CTAC), cetyltrimethylammonium bromide (CTAB), and octadecyltrimethylammonium chloride. Other exemplary surface directing agents can additionally or alternatively include hexadecyltrimethylammonium chloride and/or cetylpyridinium bromide.

Poloxamers are block copolymers of ethylene oxide and propylene oxide, more particularly nonionic triblock copolymers composed of a central hydrophobic chain of polyoxypropylene (poly(propylene oxide)) flanked by two hydrophilic chains of polyoxyethylene (poly(ethylene oxide)). Specifically, the term "poloxamer" refers to a polymer having the formula HO(C$_2$H$_4$)a(C$_3$H$_6$O)$_b$(C$_2$H$_4$O)$_a$H in which "a" and "b" denote the number of polyoxyethylene and polyoxypropylene units, respectively. Poloxamers are also known by the trade name Pluronic®, for example Pluronic® 123 and Pluronic® F127. An additional triblock polymer is B50-6600.

Nonionic polyoxyethylene alkyl ethers are known by the trade name Brij®, for example Brij® 56, Brij® 58, Brij® 76, Brij® 78. Gemini surfactants are compounds having at least two hydrophobic groups and at least one or optionally two hydrophilic groups per molecule have been introduced.

ii. Porogen

A porogen material is capable of forming domains, discrete regions, voids and/or pores in the organosilica material. An example of a porogen is a block copolymer (e.g., a di-block polymer). As used herein, porogen does not include water. Examples of polymer porogens can include, but are not limited to, polyvinyl aromatics, such as polystyrenes, polyvinylpyridines, hydrogenated polyvinyl aromatics, polyacrylonitriles, polyalkylene oxides, such as polyethylene oxides and polypropylene oxides, polyethylenes, polylactic acids, polysiloxanes, polycaprolactones, polycaprolactams, polyurethanes, polymethacrylates, such as polymethylmethacrylate or polymethacrylic acid, polyacrylates, such as polymethylacrylate and polyacrylic acid, polydienes such as polybutadienes and polyisoprenes, polyvinyl chlorides, polyacetals, and amine-capped alkylene oxides, as well as combinations thereof.

Alternately, porogens can be thermoplastic homopolymers and random (as opposed to block) copolymers. As used herein, "homopolymer" means compounds comprising repeating units from a single monomer. Suitable thermoplastic materials can include, but are not limited to, homopolymers or copolymers of polystyrenes, polyacrylates, polymethacrylates, polybutadienes, polyisoprenes, polyphenylene oxides, polypropylene oxides, polyethylene oxides, poly(dimethylsiloxanes), polytetrahydrofurans, polyethylenes, polycyclohexylethylenes, polyethyloxazolines, polyvinylpyridines, polycaprolactones, polylactic acids, copolymers of these materials and mixtures of these materials. Examples of polystyrene include, but are not limited to anionic polymerized polystyrene, syndiotactic polystyrene, unsubstituted and substituted polystyrenes (for example, poly(α-methyl styrene)). The thermoplastic materials may be linear, branched, hyperbranched, dendritic, or star like in nature.

Alternately, the porogen can be a solvent. Examples of solvents can include, but are not limited to, ketones (e.g., cyclohexanone, cyclopentanone, 2-heptanone, cycloheptanone, cyclooctanone, cyclohexylpyrrolidinone, methyl isobutyl ketone, methyl ethyl ketone, acetone), carbonate compounds (e.g., ethylene carbonate, propylene carbonate), heterocyclic compounds (e.g., 3-methyl-2-oxazolidinone, dimethylimidazolidinone, N-methylpyrrolidone, pyridine), cyclic ethers (e.g., dioxane, tetrahydrofuran), chain ethers (e.g., diethyl ether, ethylene glycol dimethyl ether, propylene glycol dimethyl ether, tetraethylene glycol dimethyl ether, polyethylene glycol dimethyl ether, ethylene glycol monomethyl ether, ethylene glycol monoethyl ether, propylene glycol monomethyl ether (PGME), triethylene glycol monobutyl ether, propylene glycol monopropyl ether, triethylene glycol monomethyl ether, diethylene glycol ethyl ether, diethylene glycol methyl ether, dipropylene glycol methyl ether, dipropylene glycol dimethyl ether, propylene glycol phenyl ether, tripropylene glycol methyl ether), alcohols (e.g., methanol, ethanol), polyhydric alcohols (e.g., ethylene glycol, propylene glycol, polyethylene glycol, polypropylene glycol, glycerin, dipropylene glycol), nitrile compounds (e.g., acetonitrile, glutarodinitrile, methoxyacetonitrile, propionitrile, benzonitrile), esters (e.g., ethyl acetate, butyl acetate, methyl lactate, ethyl lactate, methyl methoxypropionate, ethyl ethoxypropionate, methyl pyruvate, ethyl pyruvate, propyl pyruvate, 2-methoxyethyl acetate, ethylene glycol monoethyl ether acetate, propylene glycol monomethyl ether acetate (PGMEA), butyrolactone, phosphoric acid ester, phosphonic acid ester), aprotic polar substances (e.g., dimethyl sulfoxide, sulfolane, dimethylformamide, dimethylacetamide), nonpolar solvents (e.g., toluene, xylene, mesitylene), chlorine-based solvents (e.g., methylene dichloride, ethylene dichloride), benzene, dichlorobenzene, naphthalene, diphenyl ether, diisopropylbenzene, triethylamine, methyl benzoate, ethyl benzoate, butyl benzoate, monomethyl ether acetate hydroxy ethers such as dibenzylethers, diglyme, triglyme, and mixtures thereof.

iii. Base/Acid

In various embodiments, the aqueous mixture used in methods provided herein can comprise a base and/or an acid. In certain embodiments where the aqueous mixture comprises a base, the aqueous mixture can have a pH from about 8 to about 15, from about 8.5 to about 14.5, from about 9 to about 14, alternatively from about 8.5 to about 10. In a particular embodiment comprising a base, the pH can be from about 9 to about 15 or from about 9 to about 14. Exemplary bases can include, but are not limited to, sodium hydroxide, potassium hydroxide, lithium hydroxide, pyridine, pyrrole, piperazine, pyrrolidine, piperidine, picoline, monoethanolamine, diethanolamine, dimethylmonoethanolamine, monomethyldiethanolamine, triethanolamine, diazabicyclooctane, diazabicyclononane, diazabicycloundecene, tetramethylammonium hydroxide, tetraethylammonium hydroxide, tetrapropylammonium hydroxide, tetrabutylammonium hydroxide, ammonia, ammonium hydroxide, methylamine, ethylamine, propylamine, butylamine, pentylamine, hexylamine, octylamine, nonylamine, decylamine, N,N-dimethylamine, N,N-diethylamine, N,N-dipropylamine, N,N-dibutylamine, trimethylamine, triethylamine, tripropylamine, tributylamine, cyclohexylamine, trimethylimidine, 1-amino-3-methylbutane, dimethylglycine, 3-amino-3-methylamine, and the like. These bases may be used either singly or in combination. In a particular embodiment, the base can comprise or be sodium hydroxide and/or ammonium hydroxide. In certain embodiments where the aqueous mixture comprises an acid, the aqueous mixture can have a pH from about 0.01 to about 6.0, from about 0.1 to about 5.5, about 0.2 to about to about 4.8, about 0.5 to about 3.8, from about 0.8 to about to about 3.0. In a particular embodiment comprising an acid, the pH can be from about 0.01 to about 6.0, about 0.2 to about 6.0, about 0.2 to about 5.0 or about 0.2 to about 4.5. Exemplary acids can include, but are not limited to, inorganic acids such as hydrochloric acid, nitric acid, sulfuric acid, hydrofluoric acid, phosphoric acid, boric acid and oxalic acid; and organic acids such as acetic acid, propionic acid, butanoic acid, pentanoic acid, hexanoic acid, heptanoic acid, octanoic acid, nonanoic acid, decanoic acid, oxalic acid, maleic acid, methylmalonic acid, adipic acid, sebacic acid, gallic acid, butyric acid, mellitic acid, arachidonic acid, shikimic acid, 2-ethylhexanoic acid, oleic acid, stearic acid, linoleic acid, linolenic acid, salicylic acid, benzoic acid, p-amino-benzoic acid, p-toluenesulfonic acid, benzenesulfonic acid, monochloroacetic acid, dichloroacetic acid, trichloroacetic acid, trifluoroacetic acid, formic acid, malonic acid, sulfonic acid, phthalic acid, fumaric acid, citric acid, tartaric acid, succinic acid, itaconic acid, mesaconic acid, citraconic acid, malic acid, a hydrolysate of glutaric acid, a hydrolysate of maleic anhydride, a hydrolysate of phthalic anhydride, and the like. These acids may be used either singly or in combination. In a particular embodiment, the acid can comprise or be hydrochloric acid.

In various aspects, adjusting the pH of the aqueous mixture can affect the total surface area, microporous surface area and pore volume of the organosilica material made. Thus, the porosity of the organosilica material may be adjusted by adjusting the pH of the aqueous mixture. For example, when the aqueous mixture is basic and has a pH between about 8 to about 14, in particular about 9 to about 14, the organosilica material made may have one or more of the following characteristics: a) a total surface area of about 200 $m^2/g$ to about 1800 $m^2/g$, particularly about 300 $m^2/g$ to about 1700 $m^2/g$, and particularly about 400 $m^2/g$ to about 1700 $m^2/g$; b) a microporous surface area of about 0 $m^2/g$ to about 700 $m^2/g$, and particularly about 0 $m^2/g$ to about 700 $m^2/g$; c) a pore volume of about 0.2 $cm^3/g$ to about 3 $cm^3/g$, and particularly of about 0.8 $cm^3/g$ to about 1.4 $cm^3/g$.

Alternately, when the aqueous mixture is acidic and has a pH between about 0.1 to about 7, particularly about 0.1 to about 5, particularly about 0.1 to about 4.5, the organosilica material made may have one or more of the following characteristics: a) a total surface area of about 100 $m^2/g$ to about 1500 $m^2/g$, particularly about 100 $m^2/g$ to about 900 $m^2/g$, and particularly about 200 $m^2/g$ to about 900 $m^2/g$; b) a microporous surface area of about 100 $m^2/g$ to about 600 $m^2/g$, and particularly about 0 $m^2/g$ to about 500 $m^2/g$; c) a pore volume of about 0.1 $cm^3/g$ to about 1.2 $cm^3/g$, and particularly of about 0.1 $cm^3/g$ to about 0.6 $cm^3/g$.

Thus, the total surface area of an organosilica material made with a basic aqueous mixture may increase when compared to an organosilica material made with an acidic aqueous mixture. Further, the pore volume of an organosilica material made with a basic aqueous mixture may increase when compared to an organosilica material made with an acidic aqueous mixture. However, the microporous surface area of an organosilica material made with a basic aqueous mixture may decrease when compared to an organosilica material made with an acidic aqueous mixture.

iv. Compounds of Formula Ia

The methods provided herein comprise the step of adding at least one compound of Formula $[R^1R^2SiCH_2]_3$ (Ia) into the aqueous mixture to form a solution to obtain an organosilica material which is a homopolymer or copolymer comprising at least one unit of Formula (I), wherein $R^1$ can be a $C_1$-$C_4$ alkoxy group and $R^2$ can be a $C_1$-$C_4$ alkoxy group or a $C_1$-$C_4$ alkyl group.

In one embodiment, $R^1$ can comprise a $C_1$-$C_3$ alkoxy or methoxy or ethoxy. Alternately, $R^2$ can comprise a $C_1$-$C_4$ alkoxy, a $C_1$-$C_3$ alkoxy or methoxy or ethoxy. Alternately, $R^2$ can comprise methyl, ethyl or propyl, such as a methyl or ethyl. Alternately, $R^1$ can be a $C_1$-$C_2$ alkoxy group and $R^2$ can be a $C_1$-$C_2$ alkoxy group or a $C_1$-$C_2$ alkyl group. Alternately, $R^1$ can be methoxy or ethoxy and $R^2$ can be methyl or ethyl. In a particular embodiment, $R^1$ and $R^2$ can be ethoxy, such that the compound corresponding to Formula (Ia) can be 1,1,3,3,5,5-hexaethoxy-1,3,5-trisilacyclohexane, ($[(EtO)_2SiCH_2]_3$). In a particular embodiment, $R^1$ can be ethoxy and $R^2$ can be methyl, such that compound corresponding to Formula (Ia) can be 1,3,5-trimethyl-1,3,5-triethoxy-1,3,5-trisilacyclohexane, ($[EtOCH_3SiCH_2]_3$).

v. Compounds of Formula IIa

In additional embodiments, the methods provided herein can further comprise adding to the aqueous solution a compound of Formula $R^3OR^4R^5R^6Si$ (IIa) to obtain an organosilica material which is a copolymer comprising at least one unit of Formula (I), at least one unit of Formula (II) and optionally at least one unit of Formulas (III)-(VI) as described herein. $R^3$ of Formula (IIa) can be a $C_1$-$C_6$ alkyl group, and $R^4$, $R^5$ and $R^6$ each independently can be selected from the group consisting of a $C_1$-$C_6$ alkyl group, a $C_1$-$C_6$ alkoxy group, a nitrogen-containing $C_1$-$C_{10}$ alkyl group, a nitrogen-containing heteroaralkyl group, and a nitrogen-containing optionally substituted heterocycloalkyl group.

In one embodiment, $R^3$ can be a $C_1$-$C_5$ alkyl group, a $C_1$-$C_4$ alkyl group, a $C_1$-$C_3$ alkyl group, a $C_1$-$C_2$ alkyl group, or methyl. In particular, $R^3$ can be methyl or ethyl. Alternately, $R^4$, $R^5$ and $R^6$ can be each independently a $C_1$-$C_5$ alkyl group, a $C_1$-$C_4$ alkyl group, a $C_1$-$C_3$ alkyl group, a $C_1$-$C_2$ alkyl group, or methyl. Alternately, $R^3$ can be a $C_1$-$C_2$ alkyl group and $R^4$, $R^5$ and $R^6$ can be each independently a $C_1$-$C_2$ alkyl group.

Alternately, $R^4$, $R^5$ and $R^6$ can be each independently a $C_1$-$C_5$ alkoxy group, a $C_1$-$C_4$ alkoxy group, a $C_1$-$C_3$ alkoxy group, a $C_1$-$C_2$ alkoxy group, or methoxy.

Alternately, $R^3$ can be a $C_1$-$C_2$ alkyl group and $R^4$, $R^5$ and $R^6$ can be each independently a $C_1$-$C_2$ alkoxy group.

Alternately, $R^3$ can be a $C_1$-$C_2$ alkyl group and $R^4$, $R^5$ and $R^6$ can be each independently a $C_1$-$C_2$ alkyl group or a $C_1$-$C_2$ alkoxy group.

Alternately, $R^4$, $R^5$ and $R^6$ can be each independently a nitrogen-containing $C_1$-$C_9$ alkyl group, a nitrogen-containing $C_1$-$C_8$ alkyl group, a nitrogen-containing $C_1$-$C_7$ alkyl group, a nitrogen-containing $C_1$-$C_6$ alkyl group, a nitrogen-containing $C_1$-$C_5$ alkyl group, a nitrogen-containing $C_1$-$C_4$ alkyl group, a nitrogen-containing $C_1$-$C_3$ alkyl group, a nitrogen-containing $C_1$-$C_2$ alkyl group, or a methylamine. In particular, $R^4$, $R^5$ and $R^6$ can be each independently a nitrogen-containing $C_2$-$C_{10}$ alkyl group, a nitrogen-containing $C_3$-$C_{10}$ alkyl group, a nitrogen-containing $C_3$-$C_9$ alkyl group, or a nitrogen-containing $C_3$-$C_8$ alkyl group. The aforementioned nitrogen-containing alkyl groups may have one or more nitrogen atoms (e.g., 2, 3, etc.). Examples of nitrogen-containing $C_1$-$C_{10}$ alkyl groups include, but are not limited to,

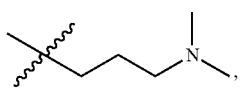

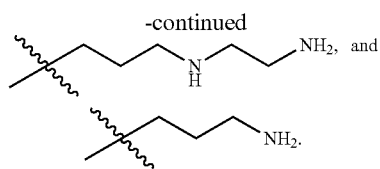

Alternately, $R^3$ can be a $C_1$-$C_2$ alkyl group and $R^4$, $R^5$ and $R^6$ can be each independently a nitrogen-containing $C_3$-$C_{10}$ alkyl group.

Alternately, $R^3$ can be a $C_1$-$C_2$ alkyl group and $R^4$, $R^5$ and $R^6$ can be each independently a $C_1$-$C_2$ alkyl group, a $C_1$-$C_2$ alkoxy group or a nitrogen-containing $C_3$-$C_8$ alkyl group.

Alternately, $R^4$, $R^5$ and $R^6$ can be each independently a nitrogen-containing heteroaralkyl group. The nitrogen-containing heteroaralkyl group can be a nitrogen-containing $C_4$-$C_{12}$ heteroaralkyl group, a nitrogen-containing $C_4$-$C_{10}$ heteroaralkyl group, or a nitrogen-containing $C_4$-$C_8$ heteroaralkyl group. Examples of nitrogen-containing heteroaralkyl groups include but are not limited to pyridinylethyl, pyridinylpropyl, pyridinylmethyl, indolylmethyl, pyrazinylethyl, and pyrazinylpropyl. The aforementioned nitrogen-containing heteroaralkyl groups may have one or more nitrogen atoms (e.g., 2, 3, etc.).

Alternately, $R^3$ can be a $C_1$-$C_2$ alkyl group and $R^4$, $R^5$ and $R^6$ can be each independently a nitrogen-containing heteroaralkyl group.

Alternately, $R^3$ can be a $C_1$-$C_2$ alkyl group and $R^4$, $R^5$ and $R^6$ can be each independently a $C_1$-$C_2$ alkyl group, a $C_1$-$C_2$ alkoxy group, a nitrogen-containing $C_3$-$C_8$ alkyl group or a nitrogen-containing heteroaralkyl group.

Alternately, $R^4$, $R^5$ and $R^6$ can be each independently a nitrogen-containing heterocycloalkyl group, wherein the heterocycloalkyl group may be optionally substituted with a $C_1$-$C_6$ alkyl group, particularly a $C_1$-$C_4$ alkyl group. The nitrogen-containing heterocycloalkyl group can be a nitrogen-containing $C_4$-$C_{12}$ heterocycloalkyl group, a nitrogen-containing $C_4$-$C_{10}$ heterocycloalkyl group, or a nitrogen-containing $C_4$-$C_8$ heterocycloalkyl group. Examples of nitrogen-containing heterocycloalkyl groups include but are not limited to piperazinylethyl, piperazinylpropyl, piperidinylethyl, piperidinylpropyl. The aforementioned nitrogen-containing heterocycloalkyl groups may have one or more nitrogen atoms (e.g., 2, 3, etc.).

Alternately, $R^3$ can be a $C_1$-$C_2$ alkyl group and $R^4$, $R^5$ and $R^6$ can be each independently a nitrogen-containing optionally substituted heterocycloalkyl group. Alternately, $R^3$ can be a $C_1$-$C_2$ alkyl group and $R^4$, $R^5$ and $R^6$ can be each independently a $C_1$-$C_2$ alkyl group, a $C_1$-$C_2$ alkoxy group, a nitrogen-containing $C_3$-$C_8$ alkyl group, a nitrogen-containing heteroaralkyl group, or a nitrogen-containing optionally substituted heterocycloalkyl group. Alternately, $R^3$ can be a $C_1$-$C_2$ alkyl group and $R^4$, $R^5$ and $R^6$ can be each independently a $C_1$-$C_2$ alkyl group, $C_1$-$C_2$ alkoxy group, a nitrogen-containing $C_3$-$C_{10}$ alkyl group, a nitrogen-containing $C_4$-$C_{10}$ heteroaralkyl group, or a nitrogen-containing optionally substituted $C_4$-$C_{10}$ heterocycloalkyl group. In a particular embodiment, $R^3$ can be ethyl and $R^4$, $R^5$ and $R^6$ can be ethoxy, such that the compound corresponding to Formula (IIa) can be tetraethyl orthosilicate (TEOS) (($EtO)_4Si$).

In another particular embodiment, Formula (Ia) can be 1,1,3,3,5,5-hexaethoxy-1,3,5-trisilacyclohexane ($[(EtO)_2SiCH_2]_3$), the Formula (IIa) can be tetraethyl orthosilicate (TEOS) (($EtO)_4Si$). In another particular embodiment, $R^3$ can be ethyl, $R^4$ can be methyl and $R^5$ and $R^6$ can be ethoxy, such that the compound corresponding to Formula (IIa) can be methyltriethoxysilane (MTES) ((EtO)$_3$CH$_3$Si). In another particular embodiment, Formula (Ia) can be 1,1,3,3,5,5-hexaethoxy-1,3,5-trisilacyclohexane ([(EtO)$_2$SiCH$_2$]$_3$ and Formula (IIa) can be methyltriethoxysilane (MTES) ((EtO)$_3$CH$_3$Si). In certain other embodiments, these monomers can be further combined with a trivalent metal oxide source that can be aluminum tri-sec-butoxide. In another particular embodiment, Formula (Ia) can be 1,3,5-trimethyl-1,3,5-triethoxy-1,3,5-trisilacyclohexane ([EtOCH$_3$SiCH$_2$]$_3$) and Formula (IIa) can be tetraethyl orthosilicate (TEOS) ((EtO)$_4$Si). In certain other embodiments, these compounds can be further combined with a trivalent metal oxide source that can be aluminum tri-sec-butoxide. In another particular embodiment, R$^3$ can be ethyl, R$^4$ and R$^5$ can be ethoxy and R$^6$ can be

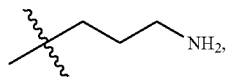 [SMILES: *CCCN]

such that the compound corresponding to Formula (Va) can be (3-aminopropyl)triethoxysilane (H$_2$N(CH$_2$)$_3$(EtO)$_3$Si).

In another particular embodiment, Formula (Ia) can be 1,3,5-trimethyl-1,3,5-triethoxy-1,3,5-trisilacyclohexane ([EtOCH$_3$SiCH$_2$]$_3$) and Formula (IIa) can be (3-aminopropyl)triethoxysilane (H$_2$N(CH$_2$)$_3$(EtO)$_3$Si). In certain other embodiments, these compounds can be further combined with a trivalent metal oxide source that can be aluminum tri-sec-butoxide.

In another particular embodiment, R$^3$ can be methyl, R$^4$ and R$^5$ can be methoxy and R$^4$ can be

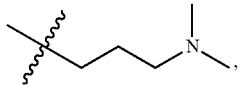 [SMILES: *CCCN(C)C]

such that the compound corresponding to Formula (IIa) can be (N,N-dimethylaminopropyl)trimethoxysilane (OCH$_3$)$_2$N(CH$_2$)$_3$)(MeO)$_3$Si). In another particular embodiment, Formula (Ia) can be 1,3,5-trimethyl-1,3,5-triethoxy-1,3,5-trisilacyclohexane ([EtOCH$_3$SiCH$_2$]$_3$) and Formula (IIa) can be (N,N-dimethylaminopropyl)trimethoxysilane (OCH$_3$)$_2$N(CH$_2$)$_3$)(MeO)$_3$Si). In certain other embodiments, these compounds can be further combined with a trivalent metal oxide source that can be aluminum tri-sec-butoxide. In another particular embodiment, R$^3$ can be ethyl, R$^4$ and R$^5$ can be ethoxy and R$^6$ can be

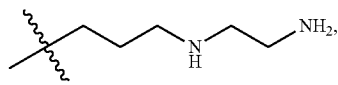 [SMILES: *CCCNCCN]

such that the compound corresponding to Formula (IIa) can be (N-(2-aminoethyl)-3-aminopropyltriethoxysilane ((H$_2$N(CH$_2$)$_2$NH (CH$_2$)$_3$)(EtO)$_2$Si). In another particular embodiment, Formula (Ia) can be 1,3,5-trimethyl-1,3,5-triethoxy-1,3,5-trisilacyclohexane ([EtOCH$_3$SiCH$_2$]$_3$) and Formula (IIa) can be (N-(2-aminoethyl)-3-aminopropyltriethoxysilane ((H$_2$N(CH$_2$)$_2$NH (CH$_2$)$_3$)(EtO)$_2$Si). In certain other embodiments, these compounds can be further combined with a trivalent metal oxide source that can be aluminum tri-sec-butoxide. In another particular embodiment, R$^3$ can be ethyl, R$^4$ and R$^5$ can be ethoxy and R$^6$ can be

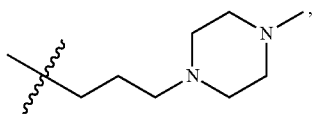 [SMILES: *CCCN1CCN(C)CC1]

such that the compound corresponding to Formula (IIa) can be 4-methyl-1-(3-triethoxysilylpropyl)-piperazine. In another particular embodiment, Formula (Ia) can be 1,3,5-trimethyl-1,3,5-triethoxy-1,3,5-trisilacyclohexane ([EtOCH$_3$SiCH$_2$]$_3$) and Formula (IIa) can be 4-methyl-1-(3-triethoxysilylpropyl)-piperazine. In certain other embodiments, these compounds can be further combined with a trivalent metal oxide source that can be aluminum tri-sec-butoxide. In another particular embodiment, R$^3$ can be ethyl, R$^4$ and R$^5$ can be ethoxy and R$^6$ can be

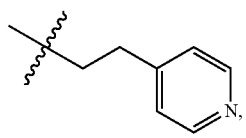

such that the compound corresponding to Formula (IIa) can be 4-(2-(triethoxysilyl)ethyl)pyridine. In another particular embodiment, Formula (Ia) can be 1,3,5-trimethyl-1,3,5-triethoxy-1,3,5-trisilacyclohexane ([EtOCH$_3$SiCH$_2$]$_3$), the trivalent metal oxide source can be aluminum tri-sec-butoxide, and Formula (IIa) can be 4-(2-(triethoxysilyl)ethyl)pyridine. In another particular embodiment, R$^3$ can be ethyl, R$^4$ and R$^5$ can be ethoxy and R$^5$ can be

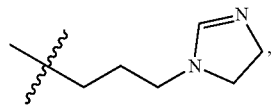 [SMILES: *CCCN1C=NCC1]

such that the compound corresponding to Formula (IIa) can be 1-(3-(triethoxysilyl)propyl)-4,5-dihydro-1H-imidazole. In another particular embodiment, Formula (Ia) can be 1,3,5-trimethyl-1,3,5-triethoxy-1,3,5-trisilacyclohexane ([EtOCH$_3$SiCH$_2$]$_3$) and Formula (IIa) can be 1-(3-(triethoxysilyl)propyl)-4,5-dihydro-1H-imidazole. In certain other embodiments, these compounds can be further combined with a trivalent metal oxide source that can be aluminum tri-sec-butoxide.

vi. Compounds of Formula IIIa

In additional embodiments, the methods provided herein can further comprise adding to the aqueous solution a compound of Formula Z$^{17}$Z$^{18}$Z$^{19}$Si—R$^7$—Si Z$^{17}$Z$^{18}$Z$^{19}$ (IIIa) to obtain an organosilica material which is a copolymer comprising at least one unit Formula (I) as described herein, at least one unit Formula (III) as described herein, and optionally at least one unit of Formulas (II) or (IV)-(VI) as described herein. In Formula (IIIa), each Z$^{17}$ can independently be a C$_1$-C$_4$ alkoxy group; each Z$^{18}$ and Z$^{19}$ independently can be a C$_1$-C$_4$ alkoxy group or a C$_1$-C$_4$ alkyl group; and R$^7$ can be selected from the group consisting a C$_1$-C$_8$ alkylene group, a C$_2$-C$_8$ alkenylene group, a C$_2$-C$_8$ alkynylene group, a nitrogen-containing $C_2$-$C_{10}$ alkylene group, an optionally substituted $C_6$-$C_{20}$ aralkyl group, and an optionally substituted $C_4$-$C_{20}$ heterocycloalkyl group.

In one embodiment, each $Z^{17}$ can be a $C_1$-$C_3$ alkoxy group, a $C_1$-$C_2$ alkoxy group, or methoxy. Each $Z^{17}$ and $Z^{18}$ independently can be a $C_1$-$C_3$ alkoxy group, a $C_1$-$C_2$ alkoxy group, or methoxy. Each $Z^{17}$ can be a $C_1$-$C_2$ alkoxy group and each $Z^{18}$ and $Z^{19}$ independently can be a $C_1$-$C_2$ alkoxy group. Each $Z^{18}$ and $Z^{19}$ independently can be a $C_1$-$C_3$ alkyl group, a $C_1$-$C_2$ alkyl group, or methyl. Each $Z^{17}$ can be a $C_1$-$C_2$ alkoxy group and each $Z^{18}$ and $Z^{19}$ independently can be a $C_1$-$C_2$ alkyl group. Each $Z^{17}$ can be a $C_1$-$C_2$ alkoxy group and each $Z^{18}$ and $Z^{19}$ independently can be a $C_1$-$C_2$ alkoxy group or a $C_1$-$C_2$ alkyl group. Alternately, $R^7$ can be a $C_1$-$C_7$ alkylene group, a $C_1$-$C_6$ alkylene group, a $C_1$-$C_5$ alkylene group, a $C_1$-$C_4$ alkylene group, a $C_1$-$C_3$ alkylene group, a $C_1$-$C_2$ alkylene group, or —$CH_2$—. Each $Z^{17}$ can be a $C_1$-$C_2$ alkoxy group; each $Z^{18}$ and $Z^{19}$ independently can be a $C_1$-$C_2$ alkoxy group or a $C_1$-$C_2$ alkyl group; and $R^7$ can be a $C_1$-$C_2$ alkylene group. Alternately, $R^7$ can be a $C_2$-$C_7$ alkenylene group, a $C_2$-$C_6$ alkenylene group, a $C_2$-$C_5$ alkenylene group, a $C_2$-$C_4$ a alkenylene group, a $C_2$-$C_3$ alkenylene group, or —CH=CH—. Each $Z^{17}$ can be a $C_1$-$C_2$ alkoxy group; each $Z^{18}$ and $Z^{19}$ independently can be a $C_1$-$C_2$ alkoxy group or a $C_1$-$C_2$ alkyl group; and $R^7$ can be a $C_1$-$C_2$ alkenylene group. Each $Z^{17}$ can be a $C_1$-$C_2$ alkoxy group; each $Z^{18}$ and $Z^{19}$ independently can be a $C_1$-$C_2$ alkoxy group or a $C_1$-$C_2$ alkyl group; and $R^7$ can be a $C_1$-$C_2$ alkylene group or a $C_1$-$C_2$ alkenylene group. Alternately, $R^7$ can be a $C_2$-$C_7$ alkynylene group, a $C_2$-$C_6$ alkynylene group, a $C_2$-$C_5$ alkynylene group, a $C_2$-$C_4$ a alkynylene group, a $C_2$-$C_3$ alkynylene group, or —C≡C—. Each $Z^{17}$ can be a $C_1$-$C_2$ alkoxy group each $Z^{18}$ and $Z^{19}$ independently can be a $C_1$-$C_2$ alkoxy group or a $C_1$-$C_2$ alkyl group; and $R^7$ can be a $C_2$-$C_4$ alkynylene group. Each $Z^{17}$ can be a $C_1$-$C_2$ alkoxy group; each $Z^{18}$ and $Z^{19}$ independently can be a $C_1$-$C_2$ alkoxy group or a $C_1$-$C_2$ alkyl group; and $R^7$ can be a $C_2$-$C_4$ alkylene group, a $C_2$-$C_4$ alkenylene group or a $C_2$-$C_4$ alkynylene group.

Alternately, $R^7$ can be a nitrogen-containing $C_2$-$C_{10}$ alkylene group, a nitrogen-containing $C_3$-$C_{10}$ alkylene group, a nitrogen-containing $C_4$-$C_{10}$ alkylene group, a nitrogen-containing $C_4$-$C_9$ alkylene group, a nitrogen-containing $C_4$-$C_{10}$ alkylene group, or nitrogen containing $C_3$-$C_8$ alkylene group. The aforementioned nitrogen-containing alkylene groups may have one or more nitrogen atoms (e.g., 2, 3, etc.). Examples of nitrogen-containing alkylene groups include, but are not limited to,

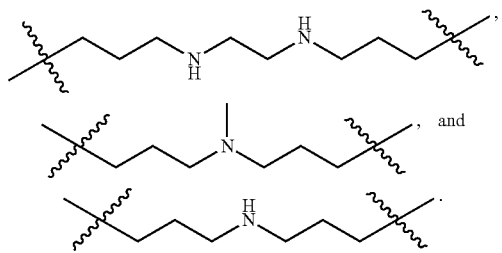

Each $Z^{17}$ can be a $C_1$-$C_2$ alkoxy group; each $Z^{18}$ and $Z^{19}$ independently can be a $C_1$-$C_2$ alkoxy group or a $C_1$-$C_2$ alkyl group; and $R^7$ can be a nitrogen-containing $C_4$-$C_{10}$ alkylene group. Each $Z^{17}$ can be a $C_1$-$C_2$ alkoxy group; each $Z^{18}$ and $Z^{19}$ independently can be a $C_1$-$C_2$ alkoxy group or a $C_1$-$C_2$ alkyl group; and $R^7$ can be a $C_2$-$C_4$ alkylene group, a $C_2$-$C_4$ alkenylene group, a $C_2$-$C_4$ alkynylene group or a nitrogen-containing $C_4$-$C_{10}$ alkylene group. Alternately, $R^7$ can be an optionally substituted $C_6$-$C_{20}$ aralkyl, an optionally substituted $C_6$-$C_{14}$ aralkyl, or an optionally substituted $C_6$-$C_{10}$ aralkyl. Examples of $C_6$-$C_{20}$ aralkyls include, but are not limited to, phenymethyl, phenylethyl, and naphthylmethyl. The aralkyl may be optionally substituted with a $C_1$-$C_6$ alkyl group, particularly a $C_1$-$C_4$ alkyl group. Each $Z^{17}$ can be a $C_1$-$C_2$ alkoxy group and each $Z^{18}$ and $Z^{19}$ independently can be a $C_1$-$C_2$ alkoxy group or a $C_1$-$C_2$ alkyl group; and R can be an optionally substituted $C_6$-$C_{10}$ aralkyl. Each $Z^{17}$ can be a $C_1$-$C_2$ alkoxy group; each $Z^{18}$ and $Z^{19}$ independently can be a $C_1$-$C_2$ alkoxy group or a $C_1$-$C_2$ alkyl group; and $R^7$ can be a $C_2$-$C_4$ alkylene group, a $C_2$-$C_4$ alkenylene group, a $C_2$-$C_4$ alkynylene group, or an optionally substituted $C_6$-$C_{10}$ aralkyl.

Alternately, $R^7$ can be an optionally substituted $C_4$-$C_{20}$ heterocycloalkyl group, an optionally substituted $C_4$-$C_{16}$ heterocycloalkyl group, an optionally substituted $C_4$-$C_{12}$ heterocycloalkyl group, or an optionally substituted $C_4$-$C_{10}$ heterocycloalkyl group. Examples of $C_4$-$C_{20}$ heterocycloalkyl groups include, but are not limited to, thienylmethyl, furylethyl, pyrrolylmethyl, piperazinylethyl, pyridylmethyl, benzoxazolylethyl, quinolinylpropyl, and imidazolylpropyl. The heterocycloalkyl may be optionally substituted with a $C_1$-$C_6$ alkyl group, particularly a $C_1$-$C_4$ alkyl group.

Each $Z^{17}$ can be a $C_1$-$C_2$ alkoxy group; each $Z^{18}$ and $Z^{19}$ independently can be a $C_1$-$C_2$ alkoxy group or a $C_1$-$C_2$ alkyl group; and $R^7$ can be an optionally substituted $C_4$-$C_{12}$ heterocycloalkyl group. Each $Z^{17}$ can be a $C_1$-$C_2$ alkoxy group. Each $Z^{18}$ and $Z^{19}$ independently can be a $C_1$-$C_2$ alkoxy group or a $C_1$-$C_2$ alkyl group; and $R^7$ can be a $C_2$-$C_4$ alkylene group, a $C_2$-$C_4$ alkenylene group, a $C_2$-$C_4$ alkynylene group, an optionally substituted $C_6$-$C_{10}$ aralkyl, or an optionally substituted $C_4$-$C_{12}$ heterocycloalkyl group. In a particular embodiment, each $Z^{17}$ and $Z^{18}$ can be ethoxy, each $Z^{19}$ can be methyl and $R^7$ can be —$CH_2CH_2$—, such that compound corresponding to Formula (IIIa) can be 1,2-bis(methyldiethoxysilyl)ethane ($CH_3(EtO)_2Si$—$CH_2CH_2$—$Si(EtO)_2CH_3$).

In certain other embodiments, these monomers can be further combined with a trivalent metal oxide source that can be aluminum tri-sec-butoxide.

In another particular embodiment, Formula (Ia) can be 1,1,3,3,5,5-hexaethoxy-1,3,5-trisilacyclohexane ($[(EtO)_2SiCH_2]_3$) and Formula (IIIa) can be 1,2-bis(methyldiethoxysilyl)ethane ($CH_3(EtO)_2Si$—$CH_2CH_2$—$Si(EtO)_2CH_3$). In another particular embodiment, each $Z^{17}$, $Z^{18}$ and $Z^{19}$ can be ethoxy and $R^7$ can be —$CH_2$—, such that compound corresponding to Formula (IIIa) can be bis(triethoxysilyl)methane (($EtO)_3Si$—$CH_2$—$Si(EtO)_3$).

In another particular embodiment, Formula (Ia) can be 1,1,3,3,5,5-hexaethoxy-1,3,5-trisilacyclohexane ($[(EtO)_2SiCH_2]_3$) and Formula (IIIa) can be bis(triethoxysilyl)methane (($EtO)_3Si$—$CH_2$—$Si(EtO)_3$). In certain other embodiments, these monomers can be further combined with a trivalent metal oxide source that can be aluminum tri-sec-butoxide. In another particular embodiment, each $Z^{17}$, $Z^{18}$ and $Z^{19}$ can be ethoxy and $R^7$ can be —HC=CH—, such that compound corresponding to Formula (IIIa) can be 1,2-bis(triethoxysilyl)ethylene (($EtO)_3Si$—HC=CH—$Si(EtO)_3$).

In another particular embodiment, Formula (Ia) can be 1,1,3,3,5,5-hexaethoxy-1,3,5-trisilacyclohexane ($[(EtO)_2SiCH_2]_3$)) and Formula (IIIa) can be 1,2-bis(triethoxysilyl)ethylene ((EtO)$_3$Si—HC=CH—Si(EtO)$_3$). In certain other embodiments, these monomers can be further combined with a trivalent metal oxide source that can be aluminum tri-sec-butoxide.

In another particular embodiment, Formula (IIIa) can be bis(triethoxysilyl)methane ((EtO)$_3$Si—CH$_2$—Si(EtO)$_3$)) and Formula (IIa) can be tetraethyl orthosilicate (TEOS) ((EtO)$_4$Si). In certain other embodiments, these monomers can be further combined with a trivalent metal oxide source that can be aluminum tri-sec-butoxide.

In a particular embodiment, each $Z^{17}$, $Z^{18}$ and $Z^{19}$ can be methoxy and $R^7$ can be

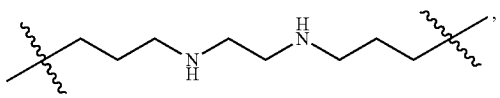 [SMILES: *CCCNCCNCCC*]

such that compound corresponding to Formula (IIIa) can be N,N'-bis[(3-trimethoxysilyl)propyl]ethylenediamine.

In another particular embodiment, Formula (Ia) can be 1,1,3,3,5,5-hexaethoxy-1,3,5-trisilacyclohexane ([(EtO)$_2$SiCH$_2$]$_3$) and Formula (IIIa) can be N,N'-bis[(3-trimethoxysilyl)propyl]ethylenediamine. In certain other embodiments, these monomers can be further combined with a trivalent metal oxide source that can be aluminum tri-sec-butoxide.

In another particular embodiment, each $Z^{17}$ and $Z^{18}$ can be ethoxy, $Z^{19}$ can be methyl and $R^7$ can be

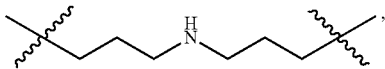 [SMILES: *CCCNCCC*]

such that compound corresponding to Formula (IIIa) can be bis[(methyldiethoxysilyl)propyl]amine.

In another particular embodiment, Formula (Ia) can be 1,1,3,3,5,5-hexaethoxy-1,3,5-trisilacyclohexane ([(EtO)$_2$SiCH$_2$]$_3$) and Formula (IIIa) can be bis[(methyldiethoxysilyl)propyl]amine. In certain other embodiments, these monomers can be further combined with a trivalent metal oxide source that can be aluminum tri-sec-butoxide.

In another particular embodiment, each $Z^{17}$ and $Z^{18}$ can be methoxy, each $Z^{19}$ can be methyl and $R^7$ can be

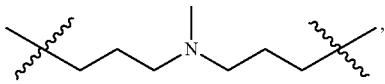 [SMILES: *CCCN(C)CCC*]

such that compound corresponding to Formula (IIIa) can be bis[(methyldimethoxysilyl)propyl]-N-methylamine.

In another particular embodiment, Formula (Ia) can be 1,1,3,3,5,5-hexaethoxy-1,3,5-trisilacyclohexane ([(EtO)$_2$SiCH$_2$]$_3$) and Formula (IIIa) can be bis[(methyldimethoxysilyl)propyl]-N-methylamine. In certain other embodiments, these monomers can be further combined with a trivalent metal oxide source that can be aluminum tri-sec-butoxide.

vii. Compounds of Formula IVa

In additional embodiments, the methods provided herein can comprise adding to the aqueous solution a source of a trivalent metal oxide to obtain an organosilica material which is a copolymer comprising at least one unit Formula (I) as described herein, at least one unit Formula (IV) as described herein, and optionally at least one unit of Formulas (II), (III), (V) or (VI) as described herein.

In various aspects, the source of trivalent metal oxide may be a compound of formula $M^3(OZ^{20})_3$ (IVa), wherein $M^3$ can be a Group 13 metal and $Z^{20}$ can be a $C_1$-$C_6$ alkyl group. In one embodiment, $M^3$ can be B, Al, Ga, In, Il, or Uut. In particular, $M^3$ can be Al or B. Alternately, $Z^{20}$ can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^{15}$ can be methyl, ethyl, propyl or butyl. Alternately, $M^3$ can be Al or B and $Z^{20}$ can be methyl, ethyl, propyl or butyl. In a particular embodiment, $M^3$ can be Al and $Z^{20}$ can be methyl, such that compound corresponding to Formula (IVa) can be aluminum trimethoxide.

In a particular embodiment, $M^3$ can be Al and $Z^{20}$ can be ethyl, such that compound corresponding to Formula (IVa) can be aluminum triethoxide. In a particular embodiment, $M^3$ can be Al and $Z^{20}$ can be propyl, such that compound corresponding to Formula (IVa) can be aluminum isopropoxide. In a particular embodiment, $M^3$ can be Al and $Z^{20}$ can be butyl, such that compound corresponding to Formula (IVa) can be aluminum tri-sec-butoxide. In another particular embodiment, Formula (Ia) can be 1,1,3,3,5,5-hexaethoxy-1,3,5-trisilacyclohexane, ([(EtO)$_2$SiCH$_2$]$_3$) and Formula (IVa) can be selected from the group consisting of aluminum trimethoxide, aluminum triethoxide, aluminum isopropoxide, and aluminum tri-sec-butoxide. In another particular embodiment, Formula (Ia) can be 1,1,3,3,5,5-hexaethoxy-1,3,5-trisilacyclohexane, ([(EtO)$_2$SiCH$_2$]$_3$) and Formula (IVa) can be aluminum tri-sec-butoxide.

Alternately, sources of trivalent metal oxides can include, but are not limited to, corresponding salts, alkoxides, oxides, and/or hydroxides of the trivalent metal, e.g., aluminum sulphate, aluminum nitrate, colloidal alumina, aluminum trihydroxide, hydroxylated alumina, Al$_2$O$_3$, aluminum halides (e.g., AlCl$_3$), NaAlO$_2$, boron nitride, B$_2$O$_3$ and/or H$_3$BO$_3$. Alternately, the source of a trivalent metal oxide may be a source of a compound of Formula (IV).

viii. Compounds of Formula Va

In yet other additional embodiments, the methods provided herein can comprise adding to the aqueous solution another source of a trivalent metal oxide to obtain an organosilica material which is a copolymer comprising at least one unit Formula (I) as described herein, at least one unit Formula (V) as described herein, and optionally at least one of Formulas (II), (III), (IV) or (VI) as described herein.

Alternately, the source of trivalent metal oxide may be a compound of Formula $(Z^{21}O)_2M^4$-O—Si(OZ$^{22}$)$_3$ (Va), wherein $M^4$ can be a Group 13 metal and $Z^{21}$ and $Z^{22}$ each independently can be a $C_1$-$C_6$ alkyl group. In one embodiment, $M^2$ can be B, Al, Ga, In, Il, or Uut. In particular, $M^4$ can be Al or B. Alternately, $Z^{21}$ and $Z^{22}$ each independently can be a $C_1$-$C_6$ alkyl group, a $C_1$-$C_5$ alkyl group, a $C_1$-$C_4$ alkyl group, a $C_1$-$C_3$ alkyl group, a $C_1$-$C_2$ alkyl group or methyl. In particular, $Z^{21}$ and $Z^{22}$ each independently can be methyl, ethyl, propyl or butyl.

Alternately, $M^4$ can be Al or B and $Z^{21}$ and $Z^{22}$ each independently can be methyl, ethyl, propyl or butyl.

As noted above, sources of trivalent metal oxides can include, but are not limited to, corresponding salts, alkoxides, oxides, and/or hydroxides of the trivalent metal, e.g., aluminum sulphate, aluminum nitrate, colloidal alumina, aluminum trihydroxide, hydroxylated alumina, Al$_2$O$_3$, aluminum halides (e.g., AlCl$_3$), NaAlO$_2$, boron nitride, B$_2$O$_3$ and/or $H_3BO_3$. Alternately, the source of a trivalent metal oxide may be a source of a compound of Formula (Va).

ix. Compounds of Formula VIa

The methods provided herein comprise the step of adding at least one cyclic compound of Formula

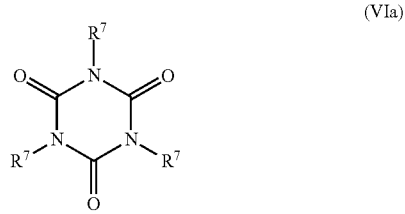

(VIa)

into the aqueous mixture to form a solution to obtain an organosilica material which is a copolymer comprising at least one unit Formula (I) as described herein, at least one unit Formula (VI) as described herein, and optionally at least one unit of Formulas (II)-(V) as described herein, wherein each $R^7$ independently can be a $X^1OX^2X^3SiX^4$ group, wherein each $X^1$ can independently be a $C_1$-$C_4$ alkyl group; each $X^2$ and $X^3$ independently can be a $C_1$-$C_4$ alkyl group or a $C_1$-$C_4$ alkoxy group; and each $X^4$ can be a $C_1$-$C_8$ alkylene group bonded to a nitrogen atom of the cyclic compound.

In various embodiments, each $X^1$ can independently be a $C_1$-$C_4$ alkyl, a $C_1$-$C_3$ alkyl, a $C_1$-$C_2$ alkyl or methyl. Each $X^2$ and $X^3$ independently can be a $C_1$-$C_4$ alkyl group, a $C_1$-$C_3$ alkyl group, a $C_1$-$C_2$ alkyl group or methyl. Each $X^2$ and $X^3$ independently can be a $C_1$-$C_4$ alkoxy group, a $C_1$-$C_3$ alkoxy group, a $C_1$-$C_2$ alkoxy group or methoxy. Each $X^2$ and $X^3$ independently can be a $C_1$-$C_2$ alkyl group or a $C_1$-$C_2$ alkoxy group. Each $X^1$ independently can be a $C_1$-$C_2$ alkyl group; and each $Z^2$ and $Z^3$ independently can be a $C_1$-$C_2$ alkyl group or a $C_1$-$C_2$ alkoxy group. Each $X^4$ can independently be a $C_1$-$C_7$ alkylene group bonded to a nitrogen atom of the cyclic compound, a $C_1$-$C_7$ alkylene group bonded to a nitrogen atom of the cyclic compound, a $C_1$-$C_6$ alkylene group bonded to a nitrogen atom of the cyclic compound, a $C_1$-$C_4$ alkylene group bonded to a nitrogen atom of the cyclic compound, a $C_1$-$C_3$ alkylene group bonded to a nitrogen atom of the cyclic compound, a $C_1$-$C_2$ alkylene group bonded to a nitrogen atom of the cyclic compound, or —$CH_2$— bonded to a nitrogen atom of the cyclic compound. Each $X^1$ independently can be a $C_1$-$C_2$ alkyl group; each $X^2$ and $X^3$ independently can be a $C_1$-$C_2$ alkyl group or a $C_1$-$C_2$ alkoxy group; and each $X^4$ independently can be a $C_1$-$C_4$ alkylene group bonded to a nitrogen atom of the cyclic compound. In a particular embodiment, each $X^1$ can be methyl; each $X^2$ and $X^3$ each independently can be methoxy; and each $X^4$ can be —$CH_2CH_2CH_2$—, such that the compound corresponding to Formula (VIa) can be tris(3-trimethoxysilylpropyl)isocyanurate.

In another particular embodiment, Formula (Ia) can be 1,1,3,3,5,5-hexaethoxy-1,3,5-trisilacyclohexane, ([(EtO)$_2$SiCH$_2$]$_3$) and Formula (VIa) can be aluminum tri-sec-butoxide. In another particular embodiment, Formula (IIa) can be tetraethyl orthosilicate (TEOS) ((EtO)$_4$Si) and Formula (VIa) can be aluminum tri-sec-butoxide.

x. Metal Chelate Sources

In additional embodiments, the methods provided herein can further comprise adding to the aqueous solution a source of metal chelate compounds. Examples of metal chelate compounds, are disclosed in U.S. Ser. No. 14/966,001 filed Dec. 11, 2015. Of these, the chelate compounds of titanium or aluminum can be of note, of which the chelate compounds of titanium can be particularly of note. These metal chelate compounds may be used either singly or in combination.

xi. Molar Ratio

In the methods described herein, in certain variations, where a plurality of monomers is selected to form the organosilica polymer, molar ratios of Formula (Ia): Formula (Ia), Formula (Ia): Formula (IIa), Formula (Ia): Formula (IIIa) Formula (Ia): Formula (IVa), Formula (Ia): Formula (Va), or Formula (Ia): Formula (VIa) may optionally be about 99:1 to about 1:99, about 75:1 to about 1:75, about 50:1 to about 1:50, about 25:1 to about 1:25, about 15:1 to about 1:15, or about 10:1 to about 1:10. For example, molar ratios of about 3:2, about 4:1, about 4:3, about 5:1, about 2:3, about 1:1 about 5:2 and about 15:1 may be used. For example, a molar ratio of Formula (Ia):Formula (Ia) can be about 3:2. A molar ratio of Formula (Ia):Formula (II) can be about 2:3, about 4:3, about 4:1 or about 3:2. A molar ratio of Formula (Ia):Formula (III) can be about 2:3, and about 4:1. A molar ratio of Formula (III):Formula (II) can be about 5:2, about 1:1, about 1:2 or about 2:3. A molar ratio of Formula (Ia):Formula (IV), Formula (Ia):Formula (V), or Formula (Ia):Formula (VI) can be about 15:1 or about 5:1.

xii. Aging the Solution

The solution formed in the methods described herein can be aged for at least about 4 hours. Alternately, the solution formed in the methods described herein can be aged for about 4 hours to about 144 hours (6 days), or about 96 hours (4 days) to about 120 hours (5 days), or about 120 hours (5 days) to about 144 hours (6 days).

Alternately, the solution formed in the method can be aged at temperature of about 10° C. to about 300° C., about 50° C. to about 300° C., about 100° C. to about 300° C., 130° C. to about 250° C., about 130° C. to about 200° C., about 130° C. to about 150° C., or about 130° C. to about 140° C.

In various aspects, adjusting the aging time and/or aging temperature of the solution formed in the methods described herein can affect the total surface area, microporous surface area, pore volume, pore radius and pore diameter of the organosilica material made. Thus, the porosity of the organosilica material may be adjusted by adjusting aging time and/or temperature.

For example, when the solution is aged for about 1 hour to about 7 hours (e.g., 1, 2, 3, 4, 5, 6 hours) at a temperature of about 80° C. to about 100° C. (e.g., 80° C., 85° C., 90° C., 95° C., etc.), the organosilica material may have one or more of the following:
i) a total surface area of about 200 m$^2$/g to about 1400 m$^2$/g, particularly about 400 m$^2$/g to about 1300 m$^2$/g, and particularly about 400 m$^2$/g to about 1200 m$^2$/g; ii) microporous surface area of about 200 m$^2$/g to about 600 m$^2$/g, particularly about 200 m$^2$/g to about 500 m$^2$/g; iii) a pore volume of about 0.2 cm$^3$/g to about 1.0 cm$^3$/g, particularly about 0.2 cm$^3$/g to about 0.8 cm$^3$/g; and iv) an average pore radius of about 0.5 nm to about 2.0 nm, particularly about 0.5 nm to about 2.0 nm, and particularly about 1.0 nm to about 1.5 nm.

Alternately, when the solution is aged for greater than about 7 hours to about 150 hours (e.g., 23, 48, 72, 144 hours) at a temperature of about 80° C. to about 100° C. (e.g., 80° C., 85° C., 90° C., 95° C., etc.), the organosilica material may have one or more of the following: i) a total surface area of about 600 m$^2$/g to about 1400 m$^2$/g, particularly about 800 m$^2$/g to about 1400 m$^2$/g, and particularly about 800 m$^2$/g to about 1200 m$^2$/g; ii) substantially no microporous surface area; iii) a pore volume of about 0.8 cm$^3$/g to about 1.4 cm$^3$/g, particularly about 0.9 cm$^3$/g to about 1.4 cm$^3$/g;

and iv) an average pore radius of about 1.0 nm to about 4.0 nm, particularly about 1.0 nm to about 4.0 nm.

Alternately, when the solution is aged for about 1 hour to about 7 hours (e.g., 1, 2, 3, 4, 5, 6 hours) at a temperature of about 110° C. to about 130° C. (e.g., 110° C., 115° C., 120° C., 125° C., etc.), the organosilica material may have one or more of the following: i) a pore volume of about 1.0 $cm^3/g$ to about 1.8 $cm^3/g$, particularly about 1.2 $cm^3/g$ to about 1.8 $cm^3/g$, particularly about 1.4 $cm^3/g$ to about 1.7 $cm^3/g$; ii) and an average pore diameter of about 2.0 nm to about 8.0 nm, particularly 4.0 nm to about 6.0 nm.

Alternately, when the solution is aged for greater than about 7 hours to about 150 hours (e.g., 23, 48, 72, 144 hours) at a temperature of about 110° C. to about 130° C. (e.g., 110° C., 115° C., 120° C., 125° C., etc.), the organosilica material may have one or more of the following: i) a pore volume of about 1.0 $cm^3/g$ to about 1.8 $cm^3/g$, particularly about 1.2 $cm^3/g$ to about 1.8 $cm^3/g$; and ii) an average pore diameter of about 8.0 nm to about 16.0 nm, particularly about 10.0 nm to about 16.0 nm, particularly about 10.0 nm to about 14.0 nm.

Thus, at shorter aging times (e.g., 7, 6, 5, 4 hours, etc.) the surface area of an organosilica material made is microporous and mesoporous, but as aging time increase, the surface area transitions to primarily mesoporous. Further, as aging time increases, pore volume, average pore radius and average pore diameter increases. Increasing aging temperature along with aging time, accelerates the above-described surface area transition and increase in pore volume, average pore radius and average pore diameter.

B. Drying the Pre-Product

The methods described herein comprise drying the pre-product to produce an organosilica material. In certain variations, the pre-product may be a gel.

In some embodiments, the pre-product (e.g., gel) formed in the method can be dried at a temperature of about 50° C. or more, about 100° C. or more, about 200° C. or more, about 350° C. or more, or 600° C. or more. Alternately, the pre-product (e.g., gel) formed in the method can be dried at temperature of about 50° C. to about 600° C., about 70° C. to about 550° C., about 80° C. to about 500° C., about 80° C. to about 250° C., or about 80° C. to about 100° C. In a particular embodiment, the pre-product (e.g., gel) formed in the method can be dried at temperature from about 70° C. to about 200° C.

Alternately, the pre-product (e.g., gel) formed in the method can be dried in a $N_2$ and/or air atmosphere.

C. Optional Further Steps

In some embodiments, as noted above, the method can further comprise calcining the organosilica material to obtain a silica material. The calcining can be performed in air or an inert gas, such as nitrogen or air enriched in nitrogen. Calcining can take place at a temperature of at least about 300° C., at least about 350° C., at least about 400° C., at least about 450° C., at least about 500° C., at least about 550° C., at least about 600° C., or at least about 650° C., for example at least about 400° C. Alternately, calcining can be performed at a temperature of about 300° C. to about 650° C., about 350° C. to about 600° C.

i. Additional Metals

In some embodiments, the organosilica material can further comprise at least one catalyst metal incorporated within the pores of the organosilica material. Exemplary catalyst metals can include, but are not limited to, a Group 6 element, a Group 8 element, a Group 9 element, a Group 10 element or a combination thereof. Exemplary Group 6 elements can include, but are not limited to, chromium, molybdenum, and/or tungsten, particularly including molybdenum and/or tungsten. Exemplary Group 8 elements can include, but are not limited to, iron, ruthenium, and/or osmium. Exemplary Group 9 elements can include, but are not limited to, cobalt, rhodium, and/or iridium, particularly including cobalt. Exemplary Group 10 elements can include, but are not limited to, nickel, palladium and/or platinum.

The catalyst metal can be incorporated into the organosilica material by any convenient method, such as by impregnation, by ion exchange, or by complexation to surface sites. The catalyst metal so incorporated may be employed to promote any one of a number of catalytic transformations commonly conducted in petroleum refining or petrochemicals production. Examples of such catalytic processes can include, but are not limited to, hydrogenation, dehydrogenation, aromatization, aromatic saturation, hydrodesulfurization, olefin oligomerization, polymerization, hydrodenitrogenation, hydrocracking, naphtha reforming, paraffin isomerization, aromatic transalkylation, saturation of double/triple bonds, and the like, as well as combinations thereof.

Thus, in another embodiment, a catalyst material comprising the organosilica material described herein is provided. The catalyst material may optionally comprise a binder. Suitable binders, include but are not limited to silica, alumina, zirconia, titania, silica-alumina, cerium oxide, magnesium oxide, or combinations thereof. Thus, in another embodiment, a catalyst material comprising the organosilica material described herein is provided.

In some embodiments, the organosilica material can further comprise cationic metal sites incorporated into the network structure. Such cationic metal sites may be incorporated by any convenient method, such as impregnation or complexation to the surface, through an organic precursor, or by some other method. This organometallic material may be employed in a number of hydrocarbon separations conducted in petroleum refining or petrochemicals production. Examples of such compounds to be desirably separated from petrochemicals/fuels can include olefins, paraffins, aromatics, and the like.

Alternately, the organosilica material can further comprise a surface metal incorporated within the pores of the organosilica material. The surface metal can be selected from a Group 1 element, a Group 2 element, a Group 13 element, and a combination thereof. When a Group 1 element is present, it can preferably comprise or be sodium and/or potassium. When a Group 2 element is present, it can include, but may not be limited to, magnesium and/or calcium. When a Group 13 element is present, it can include, but may not be limited to, boron and/or aluminum.

One or more of the Group 1, 2, 6, 8-10 and/or 13 elements may be present on an exterior and/or interior surface of the organosilica material. For example, one or more of the Group 1, 2 and/or 13 elements may be present in a first layer on the organosilica material and one or more of the Group 6, 8, 9 and/or 10 elements may be present in a second layer, e.g., at least partially atop the Group 1, 2 and/or 13 elements. Alternately, only one or more Group 6, 8, 9 and/or 10 elements may present on an exterior and/or interior surface of the organosilica material. The surface metal(s) can be incorporated into/onto the organosilica material by any convenient method, such as by impregnation, deposition, grafting, co-condensation, by ion exchange, and/or the like.

V. ORGANOSILICA MATERIAL PRODUCT-BY-PROCESS

Organosilica materials can be made from the methods described herein. In another particular embodiment, organosilica materials made from an aqueous mixture as described herein that contains essentially no structure directing agent or porogen as described herein, wherein the organosilica material may be a polymer comprising at least one unit of Formula (I) as described herein. In other aspects, organosilica materials made from an aqueous mixture as described herein that contains essentially no structure directing agent or porogen as described herein, wherein the organosilica material may be a polymer comprising at least Formula (VI) as described herein.

In yet another particular embodiment, organosilica materials made from an aqueous mixture as described herein that contains essentially no structure directing agent or porogen as described herein, wherein the organosilica material may be a copolymer of: (a) at least one unit of Formula (I) as described herein; (b) at least one unit of Formula (II) as described herein; (c) at least one unit of Formula (III) as described herein; (d) at least one unit of Formula (IV) as described herein; (e) at least one unit of Formula (V) as described herein; and/or (f) at least Formula (VI) as described herein.

The organosilica materials made from the methods described herein may exhibit an X Ray Diffraction (XRD) pattern as described herein, particularly with only one peak between about 1 and about 4 degrees 2θ. Alternately, the organosilica materials may have an average pore diameter as described herein, particularly, between about 1.5 nm and about 20.0 nm.

In another particular embodiment, an organosilica material made from aqueous mixture as described herein that contains essentially no structure directing agent or porogen as described herein i) has an X Ray Diffraction Spectrum exhibiting substantially no peaks above 4 degrees 2θ; and/or ii) is made using substantially no added structure directing agent or porogen. Alternately, the organosilica materials can exhibit substantially no peaks in the range of about 0.5 to about 10 degrees 2θ, about 0.5 to about 12 degrees 2θ range, about 0.5 to about 15 degrees 2θ, about 0.5 to about 20 degrees 2θ, about 0.5 to about 30 degrees 2θ, about 0.5 to about 40 degrees 2θ, about 0.5 to about 50 degrees 2θ, about 0.5 to about 60 degrees 2θ, about 0.5 to about 70 degrees 2θ, about 2 to about 10 degrees 2θ, about 2 to about 12 degrees 2θ range, about 2 to about 15 degrees 2θ, about 2 to about 20 degrees 2θ, about 2 to about 30 degrees 2θ, about 2 to about 40 degrees 2θ, about 2 to about 50 degrees 2θ, about 2 to about 60 degrees 2θ, about 2 to about 70 degrees 2θ, about 3 to about 10 degrees 2θ, about 3 to about 12 degrees 2θ range, about 3 to about 15 degrees 2θ, about 3 to about 20 degrees 2θ, about 3 to about 30 degrees 2θ, about 3 to about 40 degrees 2θ, about 3 to about 50 degrees 2θ, about 3 to about 60 degrees 2θ, or about 3 to about 70 degrees 2θ.

In yet another variation, the organosilica material made from aqueous mixture as described herein that contains essentially no structure directing agent or porogen as described herein may have (i) an average pore diameter between about 1.5 nm and about 25.0 nm; (ii) a pore volume about 0.1 cm$^3$/g to about 5.0 cm$^3$/g; and/or (ii) a surface area of about 200 m$^2$/g to about 2,500 m$^2$/g.

VI. USES OF THE ORGANOSILICA MATERIALS

The organosilica materials described herein find uses in several areas.

In certain embodiments, the organosilica material described herein can be used as adsorbents or support matrices for separation and/or catalysis processes.

In some cases, the organosilica materials can be used in a gas separation process as provided herein. The gas separation process can comprise contacting a gas mixture containing at least one contaminant with the organosilica material described herein as prepared according to the methods described herein.

In other aspects, the organosilica materials are used as adsorbents. Such adsorbents may remove oxygenates from a fluid stream by contacting the stream with an organosilica material to remove one or more contaminants present in the stream that adsorb to the organosilica material. Such adsorbents may remove oxygenates from a stream, such as a hydrocarbon stream, by contacting the hydrocarbon stream with an organosilica material to remove one or more oxygenates. While the adsorbents described herein, alone or in combination, preferably remove all organic oxygenates, the recycle streams of the present invention particularly comprise one or more of $C_9$ and $C_{18}$ oxygenates, or $C_{10}$ and $C_{19}$ oxygenates, before contact with the adsorbent bed. Desirably, the recycle stream has 50 (alternately 60, 65, 70, 80, 90, 95) wt % more $C_4$ to $C_{40}$ oxygenates (such as $C_9$ and $C_{18}$ oxygenates or $C_{10}$ and $C_{19}$ oxygenates), than the treated recycle stream. Stated another way, the recycle stream after contact with the adsorbent bed comprises 10 or 8 or 5 or 4 ppm or less $C_4$ to $C_{40}$ oxygenates, or $C_9$ and $C_{18}$ oxygenates or the $C_{10}$ and $C_{19}$ oxygenates.

In a particularly preferred aspect of the invention, when the recycle stream is in contact with the adsorbent bed, from 70 or 80 wt % to 95 or 99 wt % of the $C_{18}$ oxygenates or $C_{19}$ oxygenates are absorbed and from 10 or 15 or 20 wt % to 35 or 40 or 45 wt % of the non-conjugated dienes are absorbed by the at least two adsorbents after at a desirable residence time at 20° C., the residence time will be within the range from 0.1 or 1 or 5 or 10 kg diluent/hour to 30 or 40 or 50 kg/hour through the adsorbent bed. Also, preferably, from 80 or 85 or 90 wt % to 95 or 99 or 100 wt % of the $C_9$ oxygenates or $C_{10}$ oxygenates are adsorbed.

In preferred aspects of the invention, when the recycle stream is in contact with the adsorbent bed that contains at least two adsorbents, including the organosilica material, from 70 to 99 wt %, or from 80 to 95 wt %, of the $C_{18+m}$ oxygenates are absorbed and from 10 to 45 wt %, or from 15 to 40 wt %, or from 20 to 35 wt %, of the non-conjugated dienes are absorbed by the at least two adsorbents, where m is equal to the number of carbon atoms in the quenching agent. In some aspects of the invention, from 80 to 100 wt %, or from 85 to 99 wt %, or from 90 to 95 wt %, of the $C_{9+m}$ oxygenates are adsorbed, where m is equal to the number of carbon atoms in the quenching agent.

VII. EXPERIMENTAL

Further description and characterization of suitable organosilica materials for use as catalyst supports can be found in "CO-FILED CASES" which are defined to be: 1) U.S. Ser. No. 14/966,001; filed Dec. 11, 2015; 2) U.S. Ser. No. 14/965,992; filed Dec. 11, 2015; 3) U.S. Ser. No. 14/965,984; filed Dec. 11, 2015; 4) U.S. Ser. No. 14/966,383; filed Dec. 11, 2015; 5) U.S. Ser. No. 14/966,015; filed Dec. 11, 2015; 6) U.S. Ser. No. 14/966,284; filed Dec. 11, 2015, which are incorporated herein by reference in their entireties.

Gas Chromatography (GC).

A Perkin Elmer™ Clarus 500 gas chromatograph was used to evaluate the adsorption of selected oxygenates and monomers onto various adsorbents. The gas chromatograph method is shown below in Table 1.

TABLE 1

Gas Chromatograph Conditions

| | |
|---|---|
| Gas Chromatograph | PerkinElmer CLARUS ™ 500 |
| Column | Agilent Technologies Inc., Cat. No. 19091S-001 HP-PONA, 50 m × 0.200 mm, 0.50 um |
| Carrier gas | Nitrogen |
| Injector | 325° C., 1:50 split ratio |
| Injection Volume | 1-4 µL |
| Concentration | 0-8000 ppm ENB, 0-5000 pm C9 Oxygenates, 0-2000 ppm C18 Oxygenates, 0-6000 ppm n-hexadecane |
| Oven temperature | 60° C. for 4 min, 10° C./min up to 320° C. Total Time: 30 min |
| Detector | FID, 325° C., L/min Hydrogen, L/min Air |

A representative gas chromatogram of $C_9$ oxygenates and $C_{18}$ oxygenates with n-hexadecane as internal standard is shown in FIG. 1 of U.S. Ser. No. 14/311,171, filed on Jun. 20, 2014, where ENB is 5-ethylidene-2-norbornene and VNTC is 1-vinylnortricyclene (an ENB isomer).

Products were characterized by $^1$H NMR and $^{13}$C NMR as follows: A Bruker 400 MHz Advance III Spectrometer was used. Samples were dissolved in chloroform-d ($CDCl_3$) in a 5 mm NMR tube at concentrations between 10 to 15 wt % prior to being inserted into the spectrometer magnet.

$^{13}$C NMR.

$^{13}$C NMR data was collected at room temperature (20° C.). A 90 degree pulse, an acquisition time adjusted to give a digital resolution between 0.1 and 0.12 Hz, at least a 10 second pulse acquisition delay time with continuous broadband proton decoupling using swept square wave modulation without gating was employed during the entire acquisition period. The spectra were acquired with time averaging to provide a signal to noise level adequate to measure the signals of interest. Prior to data analysis, spectra were referenced by setting the chemical shift of the $CDCl_3$ solvent signal to 77.0 ppm.

$^1$H NMR.

$^1$H NMR data was collected at room temperature. Data was recorded using a maximum pulse width of 45 degree, 8 seconds between pulses and signal averaging 120 transients.

Preparation and Characterization of $C_9$ Oxygenates.

Figure 2:
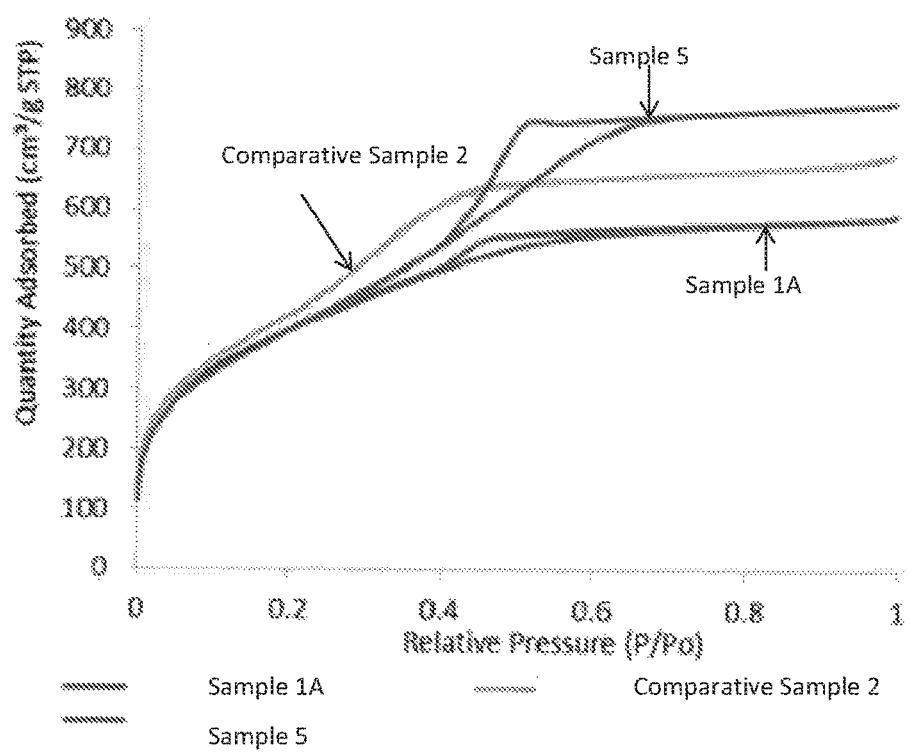
FIG. 2 illustrates an XRD spectrum for Sample 1A, Comparative Sample 2 and Sample 5.

A mixture of 44.6 g (50 mL) of ENB, 100 mL of deionized water and 2 mL of concentrated HCl was heated to 80° C. with stirring for 3 days. The HCl is present to mimic the acidic effects of a water-adsorbing molecular sieve and/or typical aluminum alkyl adducts that are difficult to characterize, but that have some acidic character. After cooling to room temperature, the organic layer was separated, washed with aq. sodium bicarbonate and then deionized water. The residual $C_9$ olefins (ENB and its isomers) were removed first from the mixture at room temperature under vacuum. The $C_9$ oxygenates were isolated by distillation using Kugelrohr (50° C./<1 mm). The $C_9$ oxygenates were characterized by $^1$H as shown in FIGS. 2a and $^{13}$C NMR as shown in FIG. 2b (C—H Correlation NMR), FIG. 2c (C-13 NMR), and FIG. 2d (C-13 NMR) of U.S. Ser. No. 14/311,171, filed on Jun. 20, 2014.

Preparation and Characterizations of $C_{18}$ Oxygenates.

Figure 3:
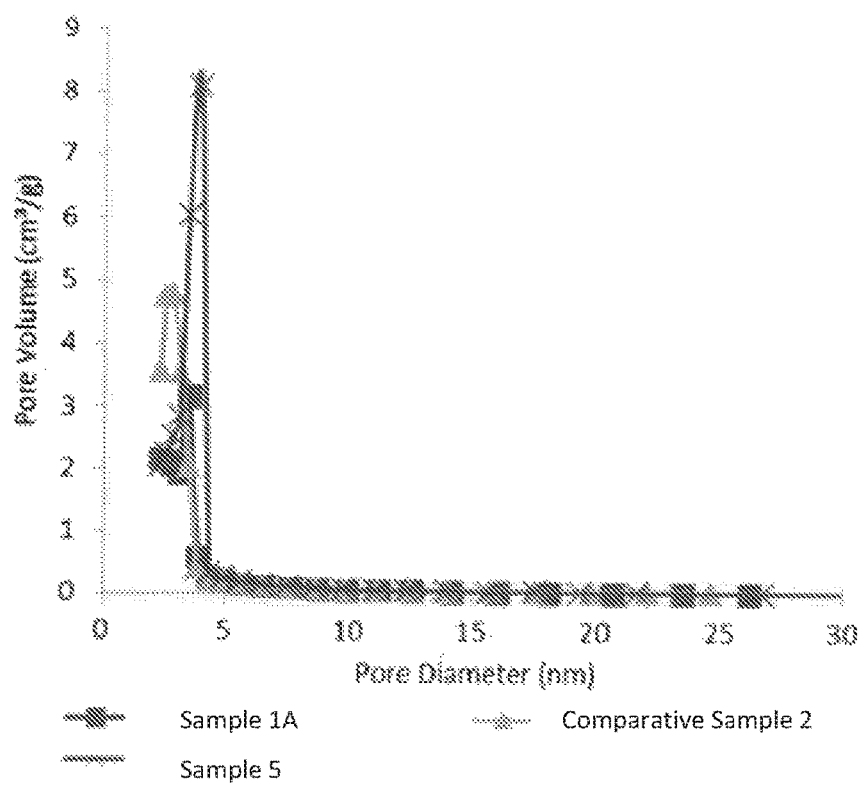
FIG. 3 illustrates a BET pore diameter distribution for Sample 1A, Comparative Sample 2 and Sample 5.

A mixture of 150 g ENB and 15 g of Y zeolite (Zeolyst CBV-712) was heated to 60° C. with stirring for 3 days. After cooling to room temperature, the mixture was diluted with hexane and filtered. Hexane and $C_9$ olefins (ENB and VNTC) were removed first from the mixture at room temperature under vacuum. The remaining mixture was separated using Kugelrohr to yield 27.1 g $C_{18}$ oxygenates (140° C./<1 mm). The $C_{18}$ oxygenates were characterized by $^1$H as shown in FIG. 3a and $^{13}$C NMR as shown in FIG. 3b (C—H Correlation NMR), FIG. 3c (C-13 NMR), and FIG. 3d (C-13 NMR) of U.S. Ser. No. 14/311,171, filed on Jun. 20, 2014.

EXAMPLES

The following examples are merely illustrative, and do not limit this disclosure in any way.

General Methods

Small Angle X-Ray Diffraction Analysis

X-ray powder diffraction (XRD) patterns were collected on a PANalytical X'pert diffractometer equipped with an accessory for low angle measurements. XRD analyses were recorded using the Cu Kα (=1.5405980 Å) line in the 2Θ range from 0.5 to 10° with a step size of 0.0167° and a counting time of 1.2 s.

Solid-State (SS) NMR Measurements $^{29}$Si MAS NMR, $^{13}$C CPMAS NMR and $^{27}$Al MAS NMR Spectra The $^{29}$Si MAS NMR spectra were recorded on a Varian InfinityPlus-400 spectrometer (operating at 9.4 T) and Varian InfinityPlus-500 (operating at 11.74 T), corresponding to $^{29}$Si Larmor frequencies of 79.4 MHz and 99.2 MHz, respectively, with a 7.5 mm MAS probe heads using 5 kHz spinning, 4.0 µs 90° pulses, and at least 60 s recycle delay, with proton decoupling during data acquisition. The $^{29}$Si chemical shifts are referenced with respect to an external tetramethyl silane ($\delta_{Si}$=0.0 ppm). The $^{13}$C CPMAS NMR spectra were recorded on a Varian InfinityPlus-500 spectrometer corresponding to $^{13}$C Larmor frequency of 125 MHz, with 1.6 mm MAS probe head using 40 kHz spinning, $^1$H-$^{13}$C cross-polarization (CP) contact time of 1 ms, a recycle delay of 1 s, with proton decoupling during data acquisition. The $^{13}$C chemical shifts are referenced with respect to an external tetramethyl silane ($\delta_c$=0.0 ppm). The $^{27}$Al MAS NMR spectra were recorded on a Varian InfinityPlus-500 corresponding to $^{27}$Al Larmor frequency of 130.1 MHz using a 4 mm MAS probe head using 12 kHz spinning, with a π/12 radian pulse length, with proton decoupling during data acquisition, and a recycle delay of 0.3 s. The chemical shifts are referenced with respect to an external solution of $Al(H_2O)_6^{3+}$ ($\delta_{Al}$=0.0 ppm). All NMR spectra were recorded at room temperature using air for spinning.

Thermal Gravimetric Analysis (TGA)

Thermal stability results were recorded on Q5000 TGA. Ramp rate was 5° C./min, temperature range was from 25° C. to 800° C. All the samples were tested in both air and nitrogen.

$CO_2$ Adsorption

The work was done with a Quantchrom autosorb iQ2. All the samples were pre-treated at 120° C. in vacuum for 3 hours before collecting the $CO_2$ isotherm at different temperatures.

Nitrogen Porosimetry

The nitrogen adsorption/desorption analyses was performed with different instruments, e.g. TriStar 3000, TriStar II 3020 and Autosorb-1. All the samples were pre-treated at 120° C. in vacuum for 4 hours before collecting the $N_2$ isotherm. The analysis program calculated the experimental data and report total surface area, microporous surface area (S), total pore volume, pore volume for micropores, average pore diameter (or radius), etc.

Example 1—Organosilica Material Syntheses Using Formula [R¹R²SiCH₂]₃ (IA) in Basic or Acidic Media 1A. Synthesis Using [(EtO)₂SiCH₂]₃ in Basic Aqueous Medium—without Surfactant A solution with 18.6 g of 30% $NH_4OH$ and 23.76 g deionized water (DI) water was made. The pH of the solution was 12.55. To the solution, 3.0 g of 1,1,3,3,5,5-hexaethoxy-1,3,5-trisilacyclohexane ([(EtO)₂SiCH₂]₃) was added, producing a mixture having the molar composition:

1.0 [(EtO)₂SiCH₂]₃:21 OH:270 $H_2O$ and stirred for 1 day at room temperature (20-25° C.). The solution was transferred to an autoclave and aged at 80° C.–90° C. for 1 day to produce a gel. The gel was dried at 80° C. in a vacuum to remove most of the water and then fully dried at 110° C. for three hours. This produced Sample 1A as a clear solid, which was converted to white powder after grinding. No surface directing agent or porogen were used in this preparation.

The procedure was repeated with the following molar composition:

4.0 [(EtO)₂SiCH₂]₃:21 OH:270 $H_2O$ to produce Sample 1B.

XRD Analysis

XRD was performed on Sample 1A. The XRD pattern of Sample 1A is shown in FIG. 1.

TGA Analysis

TGA weight loss studies were performed on Sample 1A in nitrogen and air and the data are reported in CO-FILED CASES.

Nitrogen Adsorption/Desorption Analysis

Nitrogen adsorption/desorption analysis was performed on Sample 1A, and the results are provided in CO-FILED CASES.

SS-NMR-Analysis

Figures 4, 5:
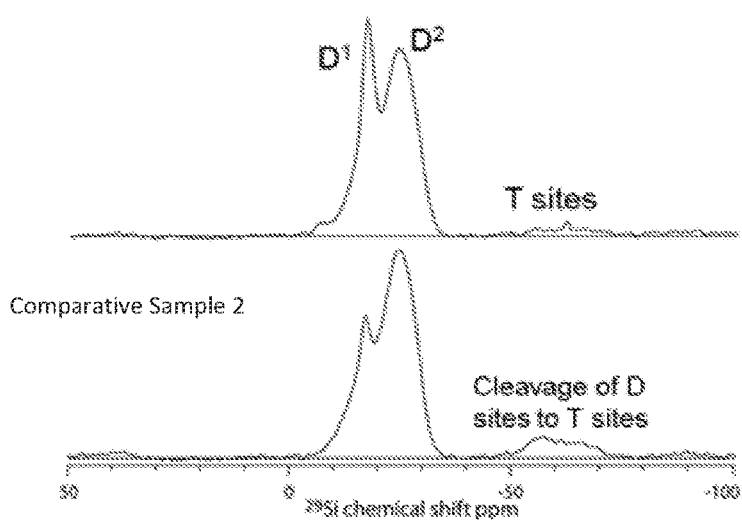
FIG. 4 illustrates a $^{29}Si$ MAS NMR spectrum for Sample 1A.
FIG. 5 illustrates a $^{29}Si$ MAS NMR spectrum for Comparative Sample 2.

Sample 1A was characterized with $^{29}Si$ MAS NMR with the results as shown in FIG. 4.

1B. Comparative—Synthesis Using [(EtO)₂SiCH₂]₃ in Basic Aqueous Medium—with Surfactant In this example, an organosilica material was prepared according to Landskron, K., et al., Science 302:266-269 (2003).

Cetyltrimethylammonium bromide (CTMABr, 0.9 mmol, 0.32 g, Aldrich) was dissolved in a mixture of 2.16 g $NH_4OH$ (35 wt %) and 3.96 g de-ionized water at 20° C. to form a solution.

[(EtO)₂SiCH₂]₃ (1.26 mmol, 0.5 g) was added to the solution, producing a solution having the molar composition:

1.0 [(EtO)₂SiCH₂]₃: 17 OH:236 $H_2O$:0.7 CTMABr which was stirred for 1 day at 20° C. and a white precipitate formed. Afterwards, the solution was aged for 1 day at 80° C. Then the precipitate was filtered off and washed with water. The sample was then stirred for 48 hours in a solution of 12 g HCl (36 wt %) and 80 g of methanol. The sample was then filtered off again and washed with MeOH, resulting in Comparative Sample 2.

XRD Analysis

XRD was performed Comparative Sample 2. A comparison of the XRD patterns for Sample A1 and Comparative Sample 2 is shown in FIG. 1. Compared to the XRD pattern of Sample 1A, the XRD pattern of Comparative Sample 2 exhibits a shoulder at about 3 degrees 2θ.

TGA Analysis

TGA weight loss studies were performed on Comparative Sample 2 in nitrogen and air and the data are reported in CO-FILED CASES.

Nitrogen Adsorption/Desorption Analysis

Nitrogen adsorption/desorption analysis was performed on Comparative Sample 2. The surface area, average pore diameter, and pore volume obtained by the nitrogen adsorption/desorption analysis for Sample 1A and Comparative Sample 2 are shown below in Table 1 and FIG. 3.

TABLE 1

| Material | BET ($m^2/g$) | Pore Diameter (nm) | Pore Volume (cc/g) |
|---|---|---|---|
| Comparative Sample 2 | 1520 | 3.02 | 1.07 |
| Sample 1A | 1410 | 3.18 | 0.92 |

SS-NMR-Analysis

Comparative Sample 2 was characterized with $^{29}Si$ MAS NMR as shown in FIG. 5. As shown below in Table 2, Sample 1A had a higher silanol content (i.e., 47%) compared to Comparative Sample 2 (i.e., 41%).

TABLE 2

| | $D_1$ | $D_2$ | T sites | Si(OH)/Si |
|---|---|---|---|---|
| Sample 1A (%) | 96 | | 4 | 47 |
| Comparative Sample 2 (%) | 45.6 / 34.7 | 50.4 / 54.3 | 11 | 41 |

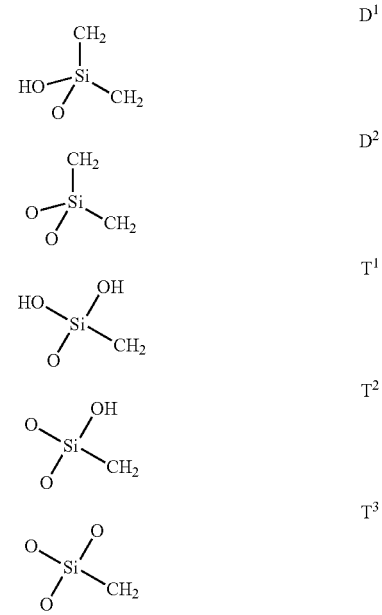

1C. Synthesis Using [(EtO)₂SiCH₂]₃ in Acidic Aqueous Medium—without Surfactant

A 14 g HCl solution with a pH of 2 was made by adding 0.778 mol water and 0.14 mmol HCl. To the solution, 1.0 g (2.52 mmol) of [(EtO)$_2$SiCH$_2$]$_3$ was added producing a solution having the molar composition: 18 [(EtO)$_2$SiCH$_2$]$_3$:1 HCl:5556 H$_2$O which was stirred for 1 day at room temperature (20-25° C.). The solution was transferred to an autoclave and aged at 94° C. for 1 day to produce a gel. The gel was dried in a vacuum at 120° C. overnight (16-24 hours) to produce Sample 3. No surface directing agent or porogen were used.

XRD Analysis

XRD was performed on Sample 3. A comparison of XRD patterns for Sample 1A and Sample 3 is reported in CO-FILED CASES.

Nitrogen Adsorption/Desorption Analysis

Nitrogen adsorption/desorption analysis was performed on Sample 3. The surface area, microporous surface area, average pore diameter, and pore volume obtained by the nitrogen adsorption/desorption analysis for Sample 3 is reported in CO-FILED CASES.

1D. Synthesis Using [(EtO)$_2$SiCH$_2$]$_3$ and [CH$_3$EtOSiCH$_2$]$_3$

A solution with 6.21 g of 30% NH$_4$OH and 7.92 g DI water was made. To the solution, 0.6 g of [(EtO)$_2$SiCH$_2$]$_3$ and 0.306 g of 1,3,5-trimethyl-1,3,5-triethoxy-1,3,5-trisilacyclohexane ([CH$_3$EtO$_2$SiCH$_2$]$_3$) was added producing a solution having the molar composition:

1.5 [(EtO)$_2$SiCH$_2$]$_3$: 1.0 [CH$_3$EtOSiCH$_2$]$_3$:53 OH:682 H$_2$O which was stirred for 1 day at room temperature (20-25° C.). The solution was transferred to an autoclave and aged at 90° C. for 1 day to produce a gel. The gel was dried in a vacuum at 120° C. overnight (16-24 hours) and Sample 4A was obtained. No structure directing agent or porogen were used.

Nitrogen Adsorption/Desorption Analysis

This above preparation method was repeated, except the relative ratio of [(EtO)$_2$SiCH$_2$]$_3$ (Reagent 1) to [CH$_3$EtO$_2$SiCH$_2$]$_3$ (Reagent 2) was varied. Nitrogen adsorption/desorption analysis was performed on each material and the results for each material is given below in Table 3.

TABLE 3

| Material | Reagent1: Reagent 2 | BET (m$^2$/g) | V (cc/g) | Pore Diameter (nm) |
|---|---|---|---|---|
| Sample 1A | 5:0 | 1410 | 0.915 | 3.18 |
| Sample 4A | 3:2 | 819 | 1.52 | 7.39 |
| Sample 4B | 4:1 | 1100 | 1.14 | 4.17 |
| Sample 4C | 2:3 | 460 | 1.09 | 13.9 |
| Sample 4D | 0:5 | — | 1.81 | 7.73E−03 | 68.8 |

As Reagent 2 increased, the average pore diameter was observed to increase, which without being bound by theory may be due to Reagent 2 containing less reactive —OR groups compared to Reagent 1. The porosity of the material decreased as Reagent 2 was greater than 60% (mol ratio).

SS-NMR-Analysis

The materials in Table 3 were characterized with $^{29}$Si MAS NMR, and the data are reported in CO-FILED CASES.

Example 2—Organosilica Material Syntheses Using Formula [R$^1$R$^2$SiCH$_2$]$_3$ (Ia) and Formula R$^3$OR$^4$R$^5$R$^6$Si (IIa) in Basic or Acidic Media 2A. Synthesis Using [(EtO)$_2$SiCH$_2$]$_3$ and tetraethylorthosilicate (TEOS) ((EtO)$_4$Si) in Basic Aqueous Medium A solution with 6.21 g of 30% NH$_4$OH (53 mmol NH$_4$OH) and 7.92 g DI water was made. To the solution, 0.8 g (2 mmol) of [(EtO)$_2$SiCH$_2$]$_3$ and 0.625 g (3 mmol) of TEOS was added to produce a solution having the molar composition:

2.0 [(EtO)$_2$SiCH$_2$]$_3$:3.0 TEOS:53 OH:682 H$_2$O which was stirred for three days at room temperature (20-25° C.). The solution was transferred to an autoclave and aged at 80° C.-90° C. for 2 days to produce a gel. The gel was dried in a vacuum at 110° C. overnight (16-24 hours) and Sample 5 was obtained. No structure directing agent or porogen was used.

A solution with 6.21 g of 30% NH$_4$OH (53 mmol NH$_4$OH) and 7.92 g DI water was made. To the solution, 3.2 g (8 mmol) of [(EtO)$_2$SiCH$_2$]$_3$ and 2.5 g (12 mmol) of TEOS was added to produce a solution having the molar composition:

8.0 [(EtO)$_2$SiCH$_2$]$_3$:12.0 TEOS:53 OH:682 H$_2$O which was stirred for three days at room temperature (20-25° C.). The solution was transferred to an autoclave and aged at 80° C.-90° C. for 2 days to produce a gel. The gel was dried in a vacuum at 110° C. overnight (16-24 hours) and Sample 5A was obtained. No structure directing agent or porogen was used.

XRD, SS-MAS NMR, and TGA weight loss studies were performed on Sample 5 and the results are reported in one or more of CO-FILED CASES. Sample 5 had a silanol content of 44%.

Nitrogen Adsorption/Desorption Analysis

Nitrogen adsorption/desorption analysis was performed on Sample 5, and the results are provided below in Table 4 and FIGS. 5 and 6.

TABLE 4

| Material | BET (m$^2$/g) | Pore Diameter (nm) | Pore Volume (cc/g) |
|---|---|---|---|
| Sample 5 | 1430 | 3.42 | 1.21 |
| Sample 5A | 1027 | 4.84 | 1.20 |

2B. Synthesis Using [(EtO)$_2$SiCH$_2$]$_3$ and TEOS in Acidic Aqueous Medium

A 14 g HCl solution with a pH of 2 was made by adding 0.778 mol water and 0.14 mmol HCl. To the solution, 0.8 g (2 mmol) of [(EtO)$_2$SiCH$_2$]$_3$ and 0.625 g (3 mmol) TEOS was added to produce a solution having the molar composition:

2.0 [(EtO)$_2$SiCH$_2$]$_3$:3.0 TEOS:0.14 H:778 H$_2$O which was stirred for 1 day at room temperature (20-25° C.). The solution was transferred to an autoclave and aged at 94° C. for 1 day to produce a gel. The gel was dried in a vacuum at 120° C. overnight (16-24 hours) to produce Sample 6. No structure directing agent or porogen were used.

XRD Analysis

XRD was performed on Sample 6. The XRD pattern of Sample 6 is shown in one or more CO-FILED CASES.

Nitrogen Adsorption/Desorption Analysis

Nitrogen adsorption/desorption analysis was performed on Sample 6, and the results are provided in one or more CO-FILED CASES.

2C. Synthesis Using [CH$_3$EtOSiCH$_2$]$_3$ and TEOS

A solution with 6.21 g of 30% NH$_4$OH (53 mmol NH$_4$OH) and 7.92 g DI water was made. To the solution, 0.612 g (2 mmol) of 1,3,5-trimethyl-1,3,5-triethoxy-1,3,5- trisilacyclohexane ([CH$_3$EtOSiCH$_2$]$_3$) and 0.625 g (3 mmoles) of TEOS was added to produce a solution having the molar composition:

2.0 [CH$_3$EtOSiCH$_2$]$_3$:3.0 TEOS:53 OH:682 H$_2$O which was stirred for 1 day at room temperature (20-25° C.). The solution was transferred to an autoclave and aged at 90° C. for 1 day to produce a gel. The gel was dried in a vacuum at 120° C. overnight (16-24 hours) and Sample 7A was obtained. No structure directing agent or porogen were used.

Nitrogen Adsorption/Desorption Analysis

This above preparation method was repeated, except the relative ratio of TEOS (Reagent 3) to [CH$_3$EtOSiCH$_2$]$_3$ (Reagent 2) was varied. Table 5 below is a summary of the N$_2$ adsorption analysis for the materials obtained with varied reagent ratios.

TABLE 5

| Material | (Reagent 3: Reagent 2) | BET (m$^2$/g) | Pore Volume (cc/g) | Pore Diameter (nm) |
|---|---|---|---|---|
| Sample 7A | 3:2 | 471 | 1.9 | 18.6 |
| Sample 7B | 3:4 | 493 | 2.16 | 23.1 |

SS-NMR-Analysis

The materials made by this method were characterized with by $^{29}$Si MAS NMR, as reported in one or more CO-FILED CASES.

2D. Synthesis Using [(EtO)$_2$SiCH$_2$]$_3$ and methyltriethoxysilane (MTES) ((EtO)$_3$CH$_3$Si)

A solution with 6.21 g of 30% NH$_4$OH (53 mmol NH$_4$OH) and 7.92 g DI water was made. To the solution, 0.4 g (1 mmol) of [(EtO)$_2$SiCH$_2$]$_3$ and 0.267 g (1.5 mmol) of MTES was added to produce a solution having the molar composition:

1.0 [(EtO)$_2$SiCH$_2$]$_3$:1.5 MTES:53 OH:682 H$_2$O which was stirred for 1 day at room temperature (20-25° C.). The solution was transferred to an autoclave and aged at 90° C. for 1 day to produce a gel. The gel was dried in a vacuum at 120° C. overnight (16-24 hours) and Sample 8A was obtained. No structure directing agent or porogen were used.

Nitrogen Adsorption/Desorption Analysis

This above preparation method was repeated, except the relative ratio of [(EtO)$_2$SiCH$_2$]$_3$ (Reagent 1) and of MTES (Reagent 2) was varied. Table 6 below is a summary of the N$_2$ adsorption analysis for the materials obtained with varied reagent ratios.

TABLE 6

| Material | Reagent 1: Reagent 2 | BET (m$^2$/g) | Pore Volume (cc/g) | Pore Diameter (nm) |
|---|---|---|---|---|
| Sample 1A | 5:0 | 1410 | 0.915 | 3.18 |
| Sample 8A | 2:3 | 821 | 1.06 | 4.5 |
| Sample 8B | 4:1 | 1130 | 1.0 | 3.59 |
| Sample 8C | 3:2 | 1040 | 1.05 | 3.89 |

Example 3—Organosilica Material Syntheses Using Formula [R$^1$R$^2$SiCH$_2$]$_3$ (Ia), Formula R$^3$OR$^4$R$^5$R$^6$Si (IIa), and/or Formula Z$^{17}$Z$^{18}$Z$^{19}$Si—R$^7$—SiZ$^{17}$Z$^{18}$Z$^{19}$ (IIIa)

3A. Synthesis Using [(EtO)$_2$SiCH$_2$]$_3$ and CH$_3$(EtO)$_2$Si—CH$_2$CH$_2$—Si(EtO)$_2$CH$_3$ A solution with 6.21 g of 30% NH$_4$OH (53 mmol NH$_4$OH) and 7.9 g DI water was made. To the solution, 0.8 g (2 mmol) of [(EtO)$_2$SiCH$_2$]$_3$ and 0.88 g (3 mmol) 1,2-bis(methyldiethyoxysilyl)ethane (CH$_3$(EtO)$_2$Si—CH$_2$CH$_2$—Si(EtO)$_2$CH$_3$) was added to produce a solution having the molar composition:

2.0 [(EtO)$_2$SiCH$_2$]$_3$:3.0 CH$_3$(EtO)$_2$Si—CH$_2$CH$_2$—Si(EtO)$_2$CH$_3$:53 OH:682 H$_2$O which was stirred for 1 day at room temperature (20-25° C.). The solution was transferred to an autoclave and aged at 80° C.-90° C. for 1 day to produce a gel. The gel was dried in a vacuum at 110° C. overnight (16-24 hours) and Sample 9 was obtained. No structure directing agent or porogen were used.

XRD Analysis

XRD was performed on Sample 9. The XRD pattern of Sample 9 is reported in one or more CO-FILED CASES.

Nitrogen Adsorption/Desorption Analysis

Nitrogen adsorption/desorption analysis was performed on Sample 9, and the results are provided in Table 7.

3B. Synthesis Using [(EtO)$_2$SiCH$_2$]$_3$ and (EtO)$_3$Si—CH$_2$—Si(EtO)$_3$

A solution with 6.21 g of 30% NH$_4$OH (53 mmol NH$_4$OH) and 7.9 g DI water was made. To the solution, 0.8 g (2 mmol) of [(EtO)$_2$SiCH$_2$]$_3$ and 1.02 g (3 mmol) of bis(triethoxysilyl)methane ((EtO)$_3$Si—CH$_2$—Si(EtO)$_3$) was added to produce a solution having the molar composition:

2.0 [(EtO)$_2$SiCH$_2$]$_3$:3.0 (EtO)$_3$Si—CH$_2$—Si(EtO)$_3$:53 OH:682 H$_2$O which was stirred for 1 day at room temperature (20-25° C.). The solution was transferred to an autoclave and aged at 80° C.-90° C. for 1 day to produce a gel. The gel was dried in a vacuum at 110° C. overnight (16-24 hours) and Sample 10 was obtained. No structure directing agent or porogen were used.

XRD Analysis

XRD was performed on Sample 10. The XRD pattern of Sample 10 is reported in one or more CO-FILED CASES.

Nitrogen Adsorption/Desorption Analysis

Nitrogen adsorption/desorption analysis was performed on Sample 10, and the results are provided in Table 7.

3C. Synthesis Using TEOS and (EtO)$_3$Si—CH$_2$—Si(EtO)$_3$

A solution with 6.21 g of 30% NH$_4$OH (53 mmoles NH$_4$OH) and 7.92 g DI water was made. To the solution, 1.7 g (5 mmol) of bis(triethoxysilyl)methane ((EtO)$_3$Si—CH$_2$—Si(EtO)$_3$) and 0.416 g (2 mmol) of TEOS were added to produce a solution having the molar composition:

5.0 (EtO)$_3$Si—CH$_2$—Si(EtO)$_3$:2.0 TEOS:53 OH:682 H$_2$O which was stirred for 1 day at room temperature (20-25° C.). The solution was transferred to an autoclave and aged at 80° C.-90° C. for 1 day to produce a gel. The gel was dried in a vacuum at 110° C. overnight (8-16 hours) and Sample 11A was obtained. No structure directing agent or porogen were used.

Two more preparations with different ratios of reagents were also made, one with a $(EtO)_3Si\text{—}CH_2\text{—}Si(EtO)_3$: TEOS molar ratio of 4:4 to obtain Sample 11B and another with a $(EtO)_3Si\text{—}CH_2\text{—}Si(EtO)_3$:TEOS molar ratio of 3:6 to obtain Sample 11C.

XRD Analysis

XRD was performed on Sample 11A. The XRD pattern of Sample 11A is reported in one or more CO-FILED CASES.

Nitrogen Adsorption/Desorption Analysis

Nitrogen adsorption/desorption analysis was performed on Sample 11A, and the results are provided in Table 7.

3D. Synthesis Using $[(EtO)_2SiCH_2]_3$ and $(EtO)_3Si\text{—}CH\text{=}CH\text{—}Si(EtO)_3$ A solution with 12.42 g of 30% $NH_4OH$ (106 mmol $NH_4OH$) and 15.8 g DI water was made. To the solution, 1.6 g (4 mmol) of $[(EtO)_2SiCH_2]_3$ and 0.352 g (1 mmol) 1,2-bis(triethoxysilyl)ethylene ($(EtO)_3Si\text{—}CH\text{=}CH\text{—}Si(EtO)_3$) was added to produce a solution having the molar composition:

4.0 $[(EtO)_2SiCH_2]_3$:1.0 $(EtO)_3Si\text{—}CH\text{=}CH\text{—}Si(EtO)_3$: 106 OH:1364 $H_2O$ which was stirred for 1 day at room temperature (20-25° C.). The solution was transferred to an autoclave and aged at 80° C.–90° C. for 1 day to produce a gel. The gel was dried in a vacuum at 110° C. overnight (8-16 hours) and Sample 12 was obtained. No structure directing agent or porogen were used.

XRD Analysis

XRD was performed on Sample 12. The XRD pattern of Sample 12 is reported in one or more CO-FILED CASES.

Nitrogen Adsorption/Desorption Analysis

Nitrogen adsorption/desorption analysis was performed on Sample 12, and the results are provided in Table 7.

TABLE 7

| Material | BET (m²/g) | S (m²/g, micro) | Pore Diameter (nm) | Pore Volume (cc/g) |
|---|---|---|---|---|
| Sample 9 | 551 | 233 | 8.4 | 0.76 |
| Sample 10 | 1270 | 512 | 3.35 | 0.96 |
| Sample 11A | 870 | 0 | 3.83 | 0.84 |
| Sample 12 | 1030 | 0 | 3.69 | 1.02 |

Example 4—Organosilica Material Syntheses Using Formula $[R^1R^2SiCH_2]_3$ (Ia) and Nitrogen-Containing Monomers Synthesis:
1. Made a solution with 6.21 g 30% $NH_4OH$ and 7.9 g DI water (53 mmol $NH_4OH$; 682 mmol $H_2O$);
2. Added 0.8 g (2 mmol) of $[(EtO)_2SiCH_2]_3$ (Reagent 1) to Reagent 2 into the above solution, kept stirring for 1 day at room temperature;
3. Transferred the solution to an autoclave, aging at 80-90° C. for 1 day;
4. Dried the gel at 110° C. in vacuum overnight.

The above synthesis was performed with the following reagents in Table 8 to obtain Samples 13, 14, 15 and 21.

The above synthesis was performed with the following reagents in Table 8 to obtain Samples 16, 17, 18 and 19 except 1.6 g of Reagent 1, 12.4 g 30% $NH_4OH$ and 15.8 g DI water were used for the preparation.

The above synthesis was performed with the following reagents in Table 8 to obtain Sample 21 except 3.2 g of Reagent 1, 24.8 g 30% $NH_4OH$ and 31.6 g of DI water were used for the preparation.

TABLE 8

| Material | Reagent 2 | Reagent 2 Amount (g) | Reagent 1: Reagent 2 Molar ratio |
|---|---|---|---|
| Sample 13 | N,N'-bis[(3-trimethoxy-silyl)propyl]ethylenediamine | 0.192 | 2:0.5 |
| Sample 14 | bis[(methyldiethoxy-silyl)propyl]amine | 0.183 | 2:0.5 |
| Sample 15 | bis[(methyldimethoxy-silyl)propyl]-N-methylamine | 0.162 | 2:0.5 |
| Sample 16 | (N,N-dimethylamino-propyl)trimethoxysilane | 1.24 | 2:3 |
| Sample 17 | N-(2-aminoethyl)-3-amino-propyltriethoxysilane | 1.58 | 2:3 |
| Sample 18 | 4-methyl-1-(3-triethoxy-silylpropyl)-piperazine | 1.83 | 2:3 |
| Sample 19 | 4-(2-(triethoxysily)ethyl)pyridine | 0.271 | 2:0.5 |
| Sample 20 | 1-(3-(triethoxysilyl)propyl)-4,5-dihydro-1H-imidazole | 0.553 | 2:0.5 |
| Sample 21 | (3-aminopropyl)triethoxysilane | 0.22 | 2:0.5 |

XRD Analysis

XRD was performed on Samples 13 and 21. The XRD patterns of Samples 13 and 21 are reported in one or more CO-FILED CASES.

Nitrogen Adsorption/Desorption Analysis

Nitrogen adsorption/desorption analysis was performed on Samples 13, 14 and 15, and the results are provided in Table 9 and are also reported in one or more CO-FILED CASES.

TABLE 9

| Material | BET (m²/g) | Pore Diameter (nm) | Pore Volume (cc/g) |
|---|---|---|---|
| Sample 13 | 1127 | 4.11 | 1.26 |
| Sample 14 | 691 | 5 | 0.96 |
| Sample 15 | 787 | 4.56 | 0.97 |

Example 5—Organosilica Material Syntheses Using Formula $[R^1R^2SiCH_2]_3$ (Ia) and Trivalent Metal Oxides (Formula $M^3(OZ^{20})_3$ (IVa))

5A. Synthesis Using $[(EtO)_2SiCH_2]_3$ and Aluminum-Tri-Sec-Butoxide

A solution with 39.6 g DI water (3410 mmol $H_2O$) and 31.15 g 30 wt % $NH_4OH$ (265 mmol $NH_4OH$) was made. To the solution, 10 g (25 mmol) of $[(EtO)_2SiCH_2]_3$ (Reagent 1) and 0.37 g (1.5 mmol) aluminum-tri-sec-butoxide (Reagent 2) was added to produce a solution having the molar composition:

25.0 $[(EtO)_2SiCH_2]_3$: 1.5 aluminum-tri-sec-butoxide:265 OH:3410 $H_2O$ which was stirred at 23-25° C. for 1 day. The Si/Al ratio between Reagent 1 and Reagent 2 was 50:1. The solution was transferred to an autoclave and aged at 90° C. for 1 day to produce a gel. The gel was dried in a vacuum at 120° C. for 1 day and Sample 22A was obtained. No surface directing agent or porogen were used.

The procedure was repeated except 1.845 g (7.5 mmol) aluminum-tri-sec-butoxide was added instead of 0.37 g (1.5 mmol) aluminum-tri-sec-butoxide to obtain Sample 22B. The Si/Al ratio between Reagent 1 and Reagent 2 was 10:1.

XRD Analysis

XRD was performed on Samples 22A and 22B. The XRD pattern of Samples 22A and 22B is shown in FIG. 19.

Nitrogen Adsorption/Desorption Analysis

Nitrogen adsorption/desorption analysis was performed on Samples 22A and 22B, and the results are provided in Table 10.

TABLE 10

| Material | Si/Al for Reagent 1: Reagent 2 | BET ($m^2/g$) | SA (micro, $m^2/g$) | V (cc/g) | Pore diameter (nm) |
|---|---|---|---|---|---|
| Sample 22A | 50 | 1273 | 646 | 0.679 | 2.13 |
| Sample 22B | 10 | 578 | 489 | 0.265 | 1.83 |

A highly porous material with more mesoporous structure was achieved when Si/Al ratio increases from 10 to 50.

SS-NMR-Analysis

Samples 22A and 22B were characterized with $^{29}$Si MAS NMR and $^{27}$Al MAS NRM, and are reported in CO-FILED cases.

Example 6—Organosilica Material Syntheses Using Formula (VIa), Formula [$R^1R^2SiCH_2$]$_3$ (Ia) and/or Formula $R^3OR^4R^5R^6Si$ (IIa)

6A. Synthesis Using tris(3-trimethoxysilylpropyl)isocyanurate

A solution with 6.23 g 30 wt. % $NH_4OH$ and 7.92 g DI water (53 mmol $NH_4OH$; 682 mmol $H_2O$) was made. To the solution 1.53 g of tris(3-trimethoxysilylpropyl) isocyanurate (2.5 mmol) was added to produce a solution having the molar composition:

2.5 tris(3-trimethoxysilylpropyl) isocyanurate:53 $NH_4OH$:682 $H_2O$ which was stirred at 22-25° C. for 1 day. The solution was transferred to an oven and kept at 70-75° C. for 1 day to produce a gel. The gel was dried in a vacuum at 120° C. overnight (16-24 hours) and Sample 23 was obtained. No surface directing agent or porogen were used.

XRD Analysis

XRD was performed on Sample 23. The XRD pattern of Sample 23 is shown in FIG. 37.

Nitrogen Adsorption/Desorption Analysis

Nitrogen adsorption/desorption analysis was performed on Sample 1, and the results are provided in Table 11 below.

6B. Synthesis Using tris(3-trimethoxysilylpropyl)isocyanurate and tetraethylorthosilicate (TEOS) (($EtO_4$)Si)

A solution with 6.23 g 30 wt. % $NH_4OH$ and 7.92 g DI water (53 mmol $NH_4OH$; 682 mmol $H_2O$) was made. To the solution 0.61 g of tris(3-trimethoxysilylpropyl)isocyanurate (1 mmol) and 0.312 g TEOS (1.5 mmol) was added to produce a solution having the molar composition:

1 tris(3-trimethoxysilylpropyl) isocyanurate:1.5 TEOS:53 $NH_4OH$:682 $H_2O$ which was stirred at 22-25° C. for 1 day. The solution was transferred to an oven and kept at 70-75° C. for 1 day to produce a gel. The gel was dried in a vacuum at 120° C. overnight (16-24 hours) and Sample 24 was obtained. No surface directing agent or porogen were used.

XRD Analysis

XRD was performed on Sample 24. The XRD pattern of Sample 24 is shown in FIG. 38.

Nitrogen Adsorption/Desorption Analysis

Nitrogen adsorption/desorption analysis was performed on Sample 24, and the results are provided in Table 11 below.

1C. Synthesis Using tris(3-trimethoxysilylpropyl) isocyanurate and [$(EtO)_2SiCH_2$]$_3$ A solution with 31.15 g 30 wt. % $NH_4OH$ and 39.9 g DI water (265 mmol $NH_4OH$; 3.410 mol $H_2O$) was made. To the solution 12.2 g of tris(3-trimethoxysilylpropyl)isocyanurate (20 mmol) and 12 g of [$(EtO)_2SiCH_2$]$_3$ (30 mmol) was added to produce a solution having the molar composition:

4 tris(3-trimethoxysilylpropyl)isocyanurate:6 [$(EtO)_2SiCH_2$]$_3$:53 $NH_4OH$:682 $H_2O$ which was stirred at 22-25° C. for 1 day. The solution was transferred to an oven and kept at 70-75° C. for 1 day to produce a gel. The gel was dried in a vacuum at 120° C. overnight (16-24 hours) and Sample 25 was obtained. No surface directing agent or porogen were used.

Nitrogen Adsorption/Desorption Analysis

Nitrogen adsorption/desorption analysis was performed on Sample 3, and the results are provided in Table 11 below.

TABLE 11

| Material | BET ($m^2/g$) | S ($m^2/g$, micro) | Pore diameter (nm) | Pore Volume (cc/g) |
|---|---|---|---|---|
| Sample 23 | 659 | 220 | 2.79 | 0.459 |
| Sample 24 | 733 | 0 | 3.84 | 0.64 |
| Sample 25 | 769 | 0 | 3.88 | 0.734 |

Example 7—pH, Gelation Time and Gelation Temperature Studies

Example 7A. Synthesis in Basic Solution (pH=8 to 13.4)

The effect of pH of the aqueous mixture during preparation of organosilica material was studied. Various organosilica materials were made with varying basic aqueous mixtures as follows:

1. Made a $NH_4OH$ solution (about 14 g) with DI water with different pHs as shown in Table 12 below;
2. Added 1 g (2.5 mmol) reagent 1 [$(EtO)_2SiCH_2$]$_3$ into the above solution, kept stirring at 22° C. to 25° C. for 1 day;
3. Transferred the solution to an autoclave and aged at about 90° C. for 1 day; and
4. Dried the final product in an oven at about 120° C. under vacuum for 1 day.

TABLE 12

| Material | NH$_4$OH Amount (g) | NH$_4$OH Mol | DI water Amount (g) | DI water (mol) | pH |
|---|---|---|---|---|---|
| Sample A | 3.72 | 0.106 | 10.4 | 0.578 | 13.41 |
| Sample B | 1.86 | 0.053 | 12.3 | 0.682 | 12.55 |
| Sample C | 0.93 | 0.027 | 13.2 | 0.734 | 12.11 |
| Sample D | 0.3 | 0.0086 | 13.8 | 0.767 | 11.52 |
| Sample E | 0.09 | 0.0026 | 14.1 | 0.783 | 11.18 |
| Sample F | About 0.006 | About 0.0002 | 14.3 | 0.794 | 10.64 |
| Sample G | About 0.0004 | About 0.00001 | 14.3 | 0.794 | 10.17 |
| Sample H | About 0.00004 | About 0.000001 | 14.3 | 0.794 | 9.61 |
| Sample H1 | About 0.000004 | About 0.0000001 | 14.2 | 0.789 | 8.0 |

Nitrogen Adsorption/Desorption Analysis

Nitrogen adsorption/desorption analysis was performed on Samples A-H1. The total surface area, microporous surface area, average pore diameter, and pore volume obtained by the nitrogen adsorption/desorption analysis for Samples A-H1 are shown below in Table 13 and are also reported in one or more of CO-FILED CASES.

TABLE 13

| Material | BET (m$^2$/g) | SA (micro, m$^2$/g) | V (cc/g) | Pore diameter (nm) |
|---|---|---|---|---|
| Sample A | 1266 | 27 | 1.011 | 3.32 |
| Sample B | 1263 | 14 | 0.971 | 3.2 |
| Sample C | 1270 | 56 | 0.946 | 3.1 |
| Sample D | 1285 | 99.7 | 0.928 | 3.04 |
| Sample E | 1308 | 107 | 0.988 | 3.2 |
| Sample F | 1325 | 205 | 1.03 | 3.12 |
| Sample G | 458 | 101 | 1.35 | 11.8 |
| Sample H | 1595 | 472 | 1.38 | 3.46 |
| Sample H1 | 52 | 56 | 0.021 | 1.65 |

Example 7B. Synthesis in Acidic Solution (pH=1.04 to 6.2)

Various organosilica materials were made with varying acidic aqueous mixtures as follows:
1. Make a HCl solution (about 14 g) with DI water with different pHs as shown in Table 14 below;
2. Added 1 g (2.5 mmol) reagent 1 (3-ring reagent) into the above solution, kept stirring at 22 to 25° C. for 1 day;
3. Transferred the solution to an autoclave and aged it at about 90° C. for 1 day; and
4. Dried the final product in an oven at about 120° C. under vacuum for 1 day.

TABLE 14

| Material | HCl Amount (g) | HCl Mol | DI water Amount (g) | DI water (mol) | pH |
|---|---|---|---|---|---|
| Sample H2 | About 0.00000397 | About 0.00000011 | 14.2 | 0.789 | 6.2 |
| Sample I | 0.0000397 | 0.0000011 | 14 | 0.778 | 4.12 |
| Sample J | 0.000397 | 0.000011 | 14 | 0.778 | 3.07 |
| Sample K | 0.00397 | 0.00011 | 14 | 0.778 | 2.11 |
| Sample L | 0.019 | 0.00052 | 14 | 0.778 | 1.43 |
| Sample M | 0.0466 | 0.00128 | 14 | 0.778 | 1.04 |

Nitrogen Adsorption/Desorption Analysis

Nitrogen adsorption/desorption analysis was performed on Samples H2-M. The total surface area, microporous surface area average pore diameter, and pore volume obtained by the nitrogen adsorption/desorption analysis for Samples H2-M are shown below in Table 15 and are also reported in one or more of CO-FILED CASES.

TABLE 15

| Material | BET (m$^2$/g) | SA (micro, m$^2$/g) | V (cc/g) | Pore diameter (nm) |
|---|---|---|---|---|
| Sample H2 | 28.4 | 33.8 | 0.014 | 2.03 |
| Sample I | 254 | 155 | 0.144 | 2.58 |
| Sample J | 642 | 389 | 0.325 | 2.44 |
| Sample K | 829 | 352 | 0.502 | 2.72 |
| Sample L | 770 | 388 | 0.436 | 2.58 |
| Sample M | 821 | 275 | 0.517 | 2.82 |

Adjusting the pH of the aqueous mixture can affect the total surface area, microporous surface area and pore volume of the organosilica material made. The total surface area generally increases with increased pH (i.e., as the aqueous mixture becomes more basic), while the microporous surface area generally decreases with increasing pH of the aqueous mixture (i.e., as the aqueous mixture becomes more basic). Thus, there may be a higher fraction of the total surface area being microporous at lower pH of the aqueous mixture (i.e. an acidic aqueous mixture).

Example 7C. Synthesis with Varying Aging Times at 90° C.

The effect of aging time during preparation of organosilica material was studied. Various organosilica materials were made with varying aging times as follows:
1. Made a NH$_4$OH solution (62.1 g, 30% wt) with 79.2 g DI water, pH=12.5;
2. Added 10 g (25 mmol) reagent 1 [(EtO)$_2$SiCH$_2$]$_3$ into the above solution, kept stirring at 22° C. to 25° C. for 1 day;
3. Transferred the solution to an autoclave and aged at about 90° C. for different times (0 to 144 hours) as shown in Table 15 below; and
4. Dried the final product in an oven at about 120° C. under vacuum for 1 day.

Nitrogen Adsorption/Desorption Analysis

Nitrogen adsorption/desorption analysis was performed on Samples N-T. The total surface area, microporous surface area, average pore radius, and pore volume obtained by the nitrogen adsorption/desorption analysis for Samples N-T are shown below in Table 16 and are also reported in one or more of CO-FILED CASES.

TABLE 16

| Material | Aging Time (hr) | BET (m$^2$/g) | SA (micro, m$^2$/g) | V (cc/g) | Pore diameter (nm) |
|---|---|---|---|---|---|
| Sample N | 0 | 485 | 398 | 0.227 | 2.48 |
| Sample O | 4 | 1191 | 500 | 0.639 | 2.6 |
| Sample P | 7 | 1247 | 276 | 0.772 | 2.98 |
| Sample Q | 23 | 1105 | 0 | 0.934 | 3.96 |
| Sample R | 48 | 1077 | 0 | 1.205 | 4.94 |
| Sample S | 72 | 929 | 0 | 1.262 | 6.12 |
| Sample T | 144 | 878 | 0 | 1.341 | 7.14 |

The organosilica material obtainable by the methods described herein may be advantageously obtainable at variable aging times and temperatures as discussed above. At early aging times, the nitrogen adsorption isotherm may exhibit complete reversibility whereby the adsorption and desorption legs of the isotherm are on top of each other. At some intermediate aging time a hysteresis may appears as an offset in the adsorption and desorption legs. The size of this offset may increase with increasing aging time to a point, after which it remains constant with increasing aging time. $N_2$ adsorption uptake capacity increases as aging time increases and the onset of an adsorption/desorption hysteresis loop was observed at 23 hours. Further, surface area was generally more microporous at shorter aging times but transitioned to primarily mesoporous as aging times increased. Additionally, average pore radius and pore volume generally increases as aging times increased.

Example 7D. Synthesis with Varying Aging Times at 120° C.

The effect of aging time with an increased aging temperature during preparation of organosilica material was studied. Various organosilica materials were made with varying aging times at an increased temperature of 120° C. as follows:
1. Made a $NH_4OH$ solution (31.05 g, 30% wt) with 39.6 g DI water, pH=12.5;
2. Added 5 g (12.5 mmol) reagent 1 $[(EtO)_2SiCH_2]_3$ into the above solution, kept stirring at 22° C. to 25° C. for 1 day;
3. Transferred the solution to an autoclave and aged at about 120° C. for different time (4 to 144 hours);
4. Dried the final product in an oven at about 120° C. under vacuum for 1 day.

Nitrogen Adsorption/Desorption Analysis

Nitrogen adsorption/desorption analysis was performed on Samples VIII-XII. The total surface area, average pore diameter, and pore volume obtained by the nitrogen adsorption/desorption analysis for Samples U-Y are shown below in Table 17 and are also reported in one or more of CO-FILED CASES.

TABLE 17

| Material | Aging Time (hr) | BET ($m^2/g$) | SA (micro, $m^2/g$) | V (cc/g) | Pore diameter (nm) |
| --- | --- | --- | --- | --- | --- |
| Sample U | 4 | 1344 | 0 | 1.33 | 3.97 |
| Sample V | 7 | 1093 | 0 | 1.61 | 5.9 |
| Sample W | 24 | 509 | 0 | 1.29 | 10 |
| Sample X | 48 | 529 | 0 | 1.67 | 12.6 |
| Sample Y | 144 | 395 | 0 | 1.35 | 13.7 |

Increasing the aging temperature along with increased aging times accelerated in the changes in total surface area, average pore diameter and pore volume observed when only the aging time was increased in Example 7C above.

SS-NMR-Analysis

The materials in Table 16 and 17 were characterized with $^{29}Si$ MAS NMR and $^{13}C$ CPMAS, and the data are reported in one or more of CO-FILED CASES. The NMR data in FIG. 26 shows the generation of different types of Si species (designated as Type 1, Type 2 and Type 3). Depending on the pH, aging temperature and/or aging time, different proportions of these species were observed. The data indicates that there were changes in the structure, especially in the higher pH preparations. The Type 1 species are typically from Si species bonded to two carbon atoms and two oxygen atoms, which in turn are bonded to other Si or H atoms. Speciation within the Type 1 species is a result of microstructure. On the other hand, Type 2 species are typically from Si species bonded to three oxygen atoms and one carbon atom, which in turn are connected to other Si or H. Type 3 species arise from Si species bonded to four oxygen atoms, in turn bonded to other Si or H atoms.

Type 1 Si species are present initially and are joined by Types 2 and 3 at longer aging times (≥23 hrs at 90° C., and >4 hrs at 120° C.). The transition from microporous to mesoporous at pH=12.5 and 90° C., is almost entirely complete at 23 hrs. aging, before the appearance of Types 2 and Type 3 Si species. The molecular changes observed in the NMR reflect changes in the Si environment under extended gelation times at pH=12.5 (data are reported in one or more of CO-FILED CASES).

In sum, the surface are and porosity of the organosilica material may be adjusted by adjusting the pH of the aqueous mixture, the aging time and/or the aging temperature during the preparation process of the organosilica material.

Example 8—Hydrothermal Stability

Hydrothermal stability was tested for Sample 1A, Comparative Sample 2, and Sample 5. All the samples were treated in DI water at 140° C. for 7 days in an autoclave. The materials demonstrated significant hydrothermal stability and mesoporosity of the samples remained after the testing. A summary of the hydrothermal stability testing results and comparison to conventional mesoporous silicas is shown below in Table 18.

TABLE 18

| | BET ($m^2/g$) | V ($cm^3/g$) | Pore diameter (nm) |
| --- | --- | --- | --- |
| Comparative Sample 2 | 1256 | 0.88 | 3.02 |
| 140° C./$H_2O$/Comparative Sample 2 | 1358 | 1.02 | 3.06 |
| Sample 1A | 1409 | 0.91 | 3.18 |
| 140° C./$H_2O$/Sample 1A | 1547 | 1.11 | 3.26 |
| Sample 5 | 1027 | 1.19 | 4.84 |
| 140° C./$H_2O$/Sample 5 | 812 | 1.5 | 6.5 |

Example 9—$CO_2$ Isotherms $CO_2$ adsorption isotherms were measured for Sample 1A, Comparative Sample 2, and Sample 5, as shown in FIG. 28. Sample 1A has similar $CO_2$ uptake compared to the Comparative Sample 2.

Example 10—Calcining Study

Sample 1A was calcined at temperatures of 300° C., 400° C., 500° C., and 600° C. in air to obtain Samples 1A(i), 1A(ii), 1A(iii) and 1A(iv), respectively. A comparison of the XRD patterns, the carbon content change, the total surface area change, and the pore volume and average pore diameter change for Sample 1A and Samples 1A(i), 1A(ii), 1A(iii) and 1A(iv), the data are reported in one or more of CO-FILED CASES. After calcining at 500° C. Sample 1A(iii) still exhibited good mesoporosity (e.g., 3 nm pore diameter and over 600 $m^2/g$ surface area).

Preparation of Adsorbent.

All materials to be tested as adsorbents were dried at 250° C. overnight in a muffle furnace equipped with nitrogen purge. The dried adsorbents were removed from the furnace while hot and allowed to cool under vacuum and then stored inside a nitrogen filled box.

Example 11: Adsorption of $C_9$ Oxygenates and $C_{18}$ Oxygenates at Room Temperature for 30 Minutes The oxygenate solution was prepared by adding known amounts of ENB (ethylidene norbornene), $C_9$ oxygenates, $C_{18}$ oxygenates, and n-hexadecane to anhydrous isohexane. The ENB used in the examples was purchased from Aldrich Chemical Company or obtained from JX Nippon Chemical Texas Inc. The anhydrous isohexane was purchased from Aldrich and further dried over 3A molecular sieves. The solution was analyzed by GC to give a pre-adsorption chromatogram.

To a dried glass vial containing 1 g adsorbent prepared according to any of Examples 1-7 or 10 above (e.g., Samples 1A or 1A(i) or 1A(ii) or 1A(iii) or 1A(iv) or 1B or 3 or 4A or 4B or 4C or 4D or 5 or 6 or 7A or 7B or 8A or 8B or 8C or 9 or 10 or 11A or 11B or 11C or 12 or 13 or 14 or 15 or 16 or 17 of 18 or 19 or 20 or 21 or 22A or 22B or 23 or 24 or 25 or A or B or C or D or E or F or G or H1 or H2 or I or J or K or L or M or N or O or P or Q or R or S or T or U or V or W or X or Y), 10 mL of oxygenate solution containing 910 ppm of $C_9$ oxygenates, 910 ppm of $C_{18}$ oxygenates, and 760 ppm of hexadecane in dried isohexane is added. The vial is capped under nitrogen and the mixture is stirred at room temperature for 30 minutes. The solution is analyzed by GC to generate a post-adsorption chromatogram. The pre-adsorption chromatograph and post adsorption chromatograph are compared, and the % of $C_9$ and $C_{18}$ oxygenates adsorbed is calculated for each adsorbent tested.

Example 12: Adsorption of Larger Amounts of Oxygenates at Room Temperature for 4 Hours The oxygenate solution is prepared by adding known amounts of ENB, $C_9$ oxygenates, $C_{18}$ oxygenates and n-hexadecane to anhydrous isohexane. The anhydrous isohexane is purchased from Aldrich and further dried over 3A molecular sieves. The solution is analyzed by GC to give a pre-adsorption chromatogram.

To a dried glass vial containing 1 g of the adsorbent prepared according to any of Examples 1-7 or 10 above (e.g., Samples 1A or 1A(i) or 1A(ii) or 1A(iii) or 1A(iv) or 1B or 3 or 4A or 4B or 4C or 4D or 5 or 6 or 7A or 7B or 8A or 8B or 8C or 9 or 10 or 11A or 11B or 11C or 12 or 13 or 14 or 15 or 16 or 17 of 18 or 19 or 20 or 21 or 22A or 22B or 23 or 24 or 25 or A or B or C or D or E or F or G or H1 or H2 or I or J or K or L or M or N or O or P or Q or R or S or T or U or V or W or X or Y), 30 mL of the oxygenate solution containing 910 ppm of $C_9$ oxygenates, 910 ppm of $C_{18}$ oxygenates and 760 ppm of hexadecane in dried isohexane is added. The vial is capped under nitrogen and the mixture is stirred at room temperature for 4 hours. The solution is analyzed by GC to generate a post-adsorption chromatogram. The pre-adsorption chromatograph and post adsorption chromatograph are compared, and the % of $C_9$ and $C_{18}$ oxygenates adsorbed is calculated for each adsorbent tested.

Example 13: Adsorption of $C_9$ Oxygenates and $C_{18}$ Oxygenates in the Presence of ENB at Room Temperature for 24 Hours The oxygenate solution is prepared by adding known amounts of ENB, $C_9$ oxygenates, $C_{18}$ oxygenates, and n-hexadecane to anhydrous isohexane. The anhydrous isohexane is purchased from Aldrich and further dried over 3A molecular sieves. The solution is analyzed by GC to give a pre-adsorption chromatogram.

To a dried glass vial containing 1 g of adsorbent prepared according to any of Examples 1-7 or 10 above (e.g., Samples 1A or 1A(i) or 1A(ii) or 1A(iii) or 1A(iv) or 1B or 3 or 4A or 4B or 4C or 4D or 5 or 6 or 7A or 7B or 8A or 8B or 8C or 9 or 10 or 11A or 11B or 11C or 12 or 13 or 14 or 15 or 16 or 17 of 18 or 19 or 20 or 21 or 22A or 22B or 23 or 24 or 25 or A or B or C or D or E or F or G or H1 or H2 or I or J or K or L or M or N or O or P or Q or R or S or T or U or V or W or X or Y), 10 ml of the oxygenate solution containing 5369 ppm of ENB, 4394 ppm of $C_9$ oxygenates, 1744 ppm of $C_{18}$ oxygenates, and 5270 ppm of hexadecane in dried isohexane is added. The vial is capped under nitrogen and the mixture is stirred at room temperature for 24 hours. The solution is analyzed by GC to generate a post-adsorption chromatogram. The pre-adsorption chromatograph and post adsorption chromatograph are compared, and the % of $C_9$ and $C_{18}$ oxygenates adsorbed is calculated for each adsorbent tested.

Example 14: Adsorption of $C_9$ Oxygenates and $C_{18}$ Oxygenates in the Presence of ENB at Room Temperature for 24 Hours The oxygenate solution is prepared by adding known amounts of ENB, $C_9$ oxygenates, $C_{18}$ oxygenates, and n-hexadecane to anhydrous isohexane. The anhydrous isohexane is purchased from Aldrich and further dried over 3A molecular sieves. The solution is analyzed by GC to give a pre-adsorption chromatogram.

To a dried glass vial containing 1 g of adsorbent prepared according to any of Examples 1-7 or 10 above (e.g., Samples 1A or 1A(i) or 1A(ii) or 1A(iii) or 1A(iv) or 1B or 3 or 4A or 4B or 4C or 4D or 5 or 6 or 7A or 7B or 8A or 8B or 8C or 9 or 10 or 11A or 11B or 11C or 12 or 13 or 14 or 15 or 16 or 17 of 18 or 19 or 20 or 21 or 22A or 22B or 23 or 24 or 25 or A or B or C or D or E or F or G or H1 or H2 or I or J or K or L or M or N or O or P or Q or R or S or T or U or V or W or X or Y), 10 mL of oxygenate solution containing 3468 ppm of ENB, 1592 ppm of $C_9$ oxygenates, 851 ppm of $C_{18}$ oxygenates, and 1586 ppm of hexadecane in dried isohexane is added. The vial is capped under nitrogen and the mixture is stirred at room temperature for 24 hours. The solution is analyzed by GC to generate a post-adsorption chromatogram. The pre-adsorption chromatograph and post adsorption chromatograph are compared, and the % of ENB, $C_9$ and $C_{18}$ oxygenates adsorbed is calculated for each adsorbent tested.

Example 15: Adsorption of $C_3$ Oxygenates and $C_8$ Oxygenates at Room Temperature for 24 Hours The oxygenate solution is prepared by adding known amounts, isopropanol and 1-octanol and n-hexadecane to anhydrous isohexane. The anhydrous isohexane is purchased from Aldrich and further dried over 3A molecular sieves. The solution is analyzed by GC to give a pre-adsorption chromatogram.

To a dried glass vial containing 1 g of adsorbent prepared according to any of Examples 1-7 or 10 above (e.g., Samples 1A or 1B or 3 or 4A or 4B or 4C or 4D or 5 or 6 or 7A or 7B or 8A or 8B or 8C or 9 or 10 or 11A or 11B or 11C or 12 or 13 or 14 or 15 or 16 or 17 of 18 or 19 or 20 or 21 or 22A or 22B or 23 or 24 or 25 or A or B or C or D or E or F or G or H1 or H2 or I or J or K or L or M or N or O or P or Q or R or S or T or U or V or W or X or Y), 10 mL of oxygenate solution containing 1000 ppm of isopropanol, 1000 ppm of 1-octanol, and 1000 ppm of hexadecane in dried isohexane is added. The vial is capped under nitrogen and the mixture is stirred at room temperature for 24 hours. The solution is analyzed by GC to generate a post-adsorption chromatogram. The pre-adsorption chromatograph and post adsorption chromatograph are compared, and the % of isopropanol and 1-octanol adsorbed is calculated for each adsorbent tested.

All documents described herein are incorporated by reference herein, including any priority documents and/or testing procedures to the extent they are not inconsistent with this text.

What is claimed is:

1. A process to remove oxygenates from a hydrocarbon stream comprising contacting the hydrocarbon stream with an organosilica material that is a polymer of at least one monomer of Formula $[Z^1OZ^2SiCH_2]_3$ (I), wherein $Z^1$ represents a hydrogen atom, a $C_1$-$C_4$ alkyl group, or a bond to a silicon atom of another monomer and $Z^2$ represents a hydroxyl group, a $C_1$-$C_4$ alkoxy group, a $C_1$-$C_6$ alkyl group, or an oxygen atom bonded to a silicon atom of another monomer.

2. The process of claim 1 further comprising:
   (i) providing hydrocarbon stream comprising a polyolefin product stream, wherein the polyolefin product stream comprises polyolefin product and unreacted monomer;
   (ii) quenching the polyolefin product stream with a quenching agent selected from water, a $C_1$-$C_8$ alcohol, and combinations thereof, to produce a quenched polyolefin stream;
   (iii) separating the quenched polyolefin stream into polyolefin product and a recycle stream; and
   (iv) contacting at least a portion of the recycle stream with an adsorbent bed comprising the organosilica material to produce a treated recycle stream, wherein the recycle stream comprises quenching agent, one or more $C_1$-$C_{40}$ oxygenates, and, optionally, one or more $C_6$-$C_{12}$ conjugated or non-conjugated diene monomers, to remove the quenching agent and/or the $C_1$-$C_{40}$ oxygenates.

3. The process of claim 1, wherein $Z^2$ represents a hydroxyl group, a $C_1$-$C_4$ alkoxy group, or an oxygen atom bonded to a silicon atom of another monomer.

4. The process of claim 1, wherein $Z^1$ represents a hydrogen atom, methyl, ethyl or a bond to a silicon atom of another monomer and $Z^2$ represents a hydroxyl group, methyl, ethyl, ethoxy, methoxy, or an oxygen bonded to a silicon atom of another monomer.

5. The process of claim 1, wherein the polymer further comprises a second distinct monomer of Formula $[Z^1OZ^2SiCH_2]_3$ (I).

6. The process of claim 1, wherein the organosilica material further comprises at least one monomer selected from the group consisting of:
   (i) a monomer of Formula $Z^3OZ^4Z^5Z^6Si$ (II), wherein $Z^3$ represents a hydrogen atom or a $C_1$-$C_4$ alkyl group, or a bond to a silicon atom of another monomer; and $Z^4$, $Z^5$ and $Z^6$ are each independently selected from the group consisting of a hydroxyl group, a $C_1$-$C_4$ alkyl group, a $C_1$-$C_4$ alkoxy group, a nitrogen-containing $C_1$-$C_{10}$ alkyl group, a nitrogen-containing heteroaralkyl group, and a nitrogen-containing optionally substituted heterocycloalkyl group, and an oxygen atom bonded to a silicon atom of another monomer;
   (ii) a monomer of Formula $Z^7Z^8Z^9Si$—R—$SiZ^7Z^8Z^9$ (III), wherein $Z^7$ represents a hydroxyl group, a $C_1$-$C_4$ alkoxy group, or an oxygen atom bonded to a silicon atom of another comonomer; $Z^8$ and $Z^9$ each independently represent a hydroxyl group, a $C_1$-$C_4$ alkoxy group, a $C_1$-$C_4$ alkyl group, or an oxygen bonded to a silicon atom of another monomer; and R is selected from the group consisting of a $C_1$-$C_8$ alkylene group, a $C_2$-$C_8$ alkenylene group, a $C_2$-$C_8$ alkynylene group, a nitrogen-containing $C_2$-$C_{10}$ alkylene group, an optionally substituted $C_6$-$C_{20}$ aralkyl and an optionally substituted $C_4$-$C_{20}$ heterocycloalkyl group;
   (iii) a trivalent metal oxide monomer of Formula $M^1(OZ^{10})_3$ (IV), wherein $M^1$ represents a Group 13 metal and $Z^{10}$ represents a hydrogen atom, a $C_1$-$C_6$ alkyl or a bond to a silicon atom of another monomer;
   (iv) a trivalent metal oxide monomer of Formula $(Z^{11}O)_2M^2$-O—$Si(OZ^{12})_3$ (V), wherein $M^2$ represents a Group 13 metal and $Z^{11}$ and $Z^{12}$ each independently represent a hydrogen atom, a $C_1$-$C_6$ alkyl group, or a bond to a silicon atom of another monomer;
   (v) a cyclic polyurea monomer of Formula

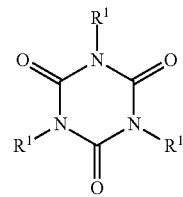

(VI)

wherein each $R^1$ is a $Z^{13}OZ^{14}Z^{15}SiZ^{16}$ group, wherein $Z^{13}$ represents a hydrogen atom, a $C_1$-$C_4$ alkyl group, or a bond to a silicon atom of another monomer unit; $Z^{14}$ and $Z^{15}$ each independently represent a hydroxyl group, a $C_1$-$C_4$ alkyl group, a $C_1$-$C_4$ alkoxy group, or an oxygen atom bonded to a silicon atom of another monomer unit; and $Z^{16}$ represents a $C_1$-$C_8$ alkylene group bonded to a nitrogen atom of the cyclic polyurea; and (vi) any combinations thereof.

7. The process of claim 2 wherein the polyolefin product stream comprises a polymer comprising ethylene, propylene and, optionally, diene.

8. The process of claim 1 wherein the organosilica material further comprises at least one cyclic polyurea monomer of Formula:

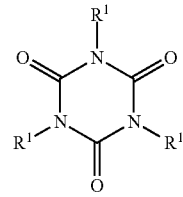

(VI)

where each $R^1$ is a $Z^{13}OZ^{14}Z^{15}SiZ^{16}$ group, and $Z^{13}$ represents a hydrogen atom, a $C_1$-$C_4$ alkyl group, or a bond to a silicon atom of another monomer unit; $Z^{14}$ and $Z^{15}$ each independently represent a hydroxyl group, a $C_1$-$C_4$ alkyl group, a $C_1$-$C_4$ alkoxy group, or an oxygen atom bonded to a silicon atom of another monomer unit; and $Z^{16}$ represents a $C_1$-$C_8$ alkylene group bonded to a nitrogen atom of the cyclic polyurea.

9. The process of claim 2, where the recycle stream has 50 wt % more $C_4$-$C_{40}$ oxygenates than the treated recycle stream.

10. The process of claim 2, where the adsorbent bed further comprises a zeolitic molecular sieve comprising a material selected from the group consisting of zeolite X, zeolite Y, zeolite A, faujasite, mordenite, ferrierite, and combinations thereof and is, optionally, binderless.

11. The process of claim 2, where the adsorbent bed further comprises an alumina adsorbent and/or a silica adsorbent.

12. The process of claim 1, wherein the organosilica material has:
  (i) an average pore diameter between about 1.5 nm and about 25.0 nm;
  (ii) a pore volume about 0.1 cm$^3$/g to about 5.0 cm$^3$/g; and/or
  (iii) a surface area of about 200 m$^2$/g to about 2,500 m$^2$/g.

13. The process of claim 1, wherein the organosilica material:
  (i) has an X-Ray diffraction spectrum exhibiting substantially no peaks above 4 degrees 2θ; and/or
  (ii) is made using substantially no added structure directing agent or porogen.

14. The process of claim 1, where the hydrocarbon stream comprises one or more of ethylene, propylene, butene, pentene, hexene, heptene, octene, nonene, decene, undecene, dodecene, butadiene, pentadiene, hexadiene, heptadiene, octadiene, nonadiene, decadiene, an isomer thereof or a polymer thereof.

15. The process of claim 2, where the hydrocarbon stream comprises the effluent of a polymerization reactor.

16. The process of claim 2, wherein the adsorbent bed comprises at least two adsorbents, wherein one adsorbent of the at least two adsorbents is the organosilica material.

17. The process of claim 2, wherein the organosilica material adsorbent removes the one or more $C_1$-$C_{40}$ oxygenates and, optionally at least one other adsorbent in the bed removes the quenching agent.

18. The process of claim 2, wherein the organosilica material:
  (i) has an X-Ray diffraction spectrum exhibiting substantially no peaks above 4 degrees 2θ; and/or
  (ii) is made using substantially no added structure directing agent or porogen.

19. The process of claim 2, wherein the one or more $C_6$-$C_{12}$ non-conjugated diene monomers is present and selected from the group consisting of: pentadiene, methylpentadiene, hexadiene, methyl-hexadiene octadiene, heptadiene, norbornadiene, 5-vinyl-2-norbornene, 5-ethylidene-2-norbornene, and combinations thereof.

20. The process of claim 2, wherein the treated recycle stream, after contact with the adsorbent bed, comprises 10 ppm or less $C_4$-$C_{40}$ oxygenates.

21. The process of claim 2, further comprising regenerating the adsorbent bed by heating the adsorbent bed to a temperature in the range of from about 150 to about 400° C.

22. The process of claim 21, further comprising subjecting the adsorbent bed to a hot diluent wash prior to and/or after regeneration.

23. The process of claim 21, further comprising sparging the adsorbent bed with hot nitrogen prior to and/or after regeneration.

24. The process of claim 2, wherein when the recycle stream is in contact with the adsorbent bed, from about 70 wt % to about 99 wt % of $C_{18}$ oxygenates are absorbed and from about 10 wt % to about 45 wt % of non-conjugated dienes are absorbed by the adsorbent bed.

25. The process of claim 2, wherein the residence time of the recycle stream with the adsorbent is within the range of from about 5 to about 20 minutes.

* * * * *